US005495070A

United States Patent [19]
John

[11] Patent Number: 5,495,070
[45] Date of Patent: Feb. 27, 1996

[54] GENETICALLY ENGINEERING COTTON PLANTS FOR ALTERED FIBER

[75] Inventor: Maliyakal John, Middleton, Wis.

[73] Assignee: Agracetus, Inc., Middleton, Wis.

[21] Appl. No.: 885,970

[22] Filed: May 18, 1992

Related U.S. Application Data

[63] Continuation-in-part of Ser. No. 617,239, Nov. 21, 1990, abandoned, which is a continuation-in-part of Ser. No. 253,243, Oct. 4, 1988, abandoned.

[51] Int. Cl.$^6$ .................. C07H 21/04; C12N 15/82; A01H 5/00
[52] U.S. Cl. .................. 800/205; 435/172.3; 435/240.4; 435/252.3; 536/24.1; 935/35; 935/36
[58] Field of Search .................. 536/24.1; 435/172.3, 435/252.3, 240.4; 800/205; 935/35, 36

[56] References Cited

U.S. PATENT DOCUMENTS

| | | | |
|---|---|---|---|
| 4,771,002 | 9/1988 | Gelvin | 435/172.3 |
| 4,943,674 | 7/1990 | Houck et al. | 800/205 |
| 5,004,863 | 4/1991 | Umbech | 800/205 |

FOREIGN PATENT DOCUMENTS

| | | |
|---|---|---|
| 0270355 | 6/1988 | European Pat. Off. . |
| 0218571 | 4/1992 | European Pat. Off. . |
| WO8504899 | 11/1985 | WIPO . |

OTHER PUBLICATIONS

Sanders et al. 1987 Nucleic Acids Research 15:1543–1558.
Willmitzer 1988 Trends in Genetics 4(1):13–18.
Beasley, C. A. and I. P. Ting, "The Effects of Plant Growth Substances on In–Vitro Fiber Development from Fertilized Cotton Ovules," Amer. J. Bot. 60:2:130–139 (1973).
Firoozabady, E. et al., "Transformation of Cotton (*Gossypium hirsetum* L.) by Agrobacterium Tumefaciens and Regeneration of Transgenic Plants," Plant Molecular Bio. 10:105–116. (1987).
Umbeck, P. et al., "Genetically Transformed Cotton (*Gossypium hirsutum* L.) Plants," Bio/Technology 5:3:263–266 (Mar. 1987).
Peterson, M. W. et al., "Study of Fiber Synthesis Related Genes in Fiber Producing and Non–Fiber Producing Species of the Genus Gossypium," Agronomy Abstract (Oct. 1988).
Anderson, M. A., et al., "Cloning of cDNA for Stylar Glycoprotein Associated with Expression of Self–Incompatibility in Nicotiana alata," Nature 321:38–44 (May, 1, 1986).
Meinert, M. C. and D. P. Delmer, "Changes in Biochemical Composition of the Cell Wall of the Cotton Fiber During Development," Plant Physiol. 59:1088–1097 (1977).
Klausner, A., "Researchers Cotton to New Fiber Findings," Bio/Tech. 3:1049–1051 (1985).
Zhou, G–Y., et al., "Introduction of Exogenous DNA into Cotton Embryos," Methods in Enzymology 10:433–481 (1983).
John, M. E., et al., "Identification and Characterization of cDNA Clones Specific for Cholesterol Side–Chain Cleavage Cytochrome p–450," Proc. Natl. Acad. Sci. 81:5628–5632 (Sep. 1984).
Ausubel, F., et al., Current Protocols in Molecular Biology, Wiley (1987).
Rangan, T. S., et al., "Somatic Embryogenesis in Tissue Cultures of *Gossypium hirsutum*" L., In Vitro 20:256 (1984).
Shoemaker, et al., "Characterization of Somatic Embryogenesis and Plant Regeneration in Cotton" (*Gossypium hirsutum* L.), Plant Cell Reports 5:3:178–181 (1986).
Gebhart, F., "C algene Expresses Recombinant Gene for Herbicide Tolerance," Genetic Engineering News (Apr. 1985).
McCormick, S., et al., "Leaf Disc Transformation of Cultivated Tomato (L. Esculentum) Using Agrobacterium tumefaciens," Plant Cell Reports 5:81–84 (1986).
Trulson, A. J. et al., "Transformation of Cucumber (*Cucumis sativus* L.) Plants with Agrobacterium rhizogenes," Theor. Appl. Genet. 73:11–15 (1986).
Velten, J. and J. Schell, "Selection Expression Plasmid Vectors for Use in Genetic Transformation of Higher Plants," Nucleic Acids Research 13:19:6981–6998 (1985).
John, M. E. and Crow, L. J., "Gene Expression in Cotton (*Gossypium hirsutum* L.) Fiber: Cloning of the mRNAs," Proc. Natl. Acad. Sci. 89:5769–5773, (1992).
John. M. E. and Stewart, J. McD., "Genes for Jeans: Biotechnological Advances in Cotton," Trends in Biotechnology, 10[5] 165–170, May 1992.
John, M. E., "An Efficient Method for Isolation of RNA and DNA From Plants Containing Polyphenolics," Nucleic Acids Research 20:2381 (1992).
Turley, R. B., et al., "Characterization of a cDNA Clone Encoding the Complete Amino Acid Sequence of Cotton Isocitrate Lyase," Biochimica et Biophysica Acta 1049:223–226 (1990).
McHenry, L. and Fritz, P. J., "Comparison of the Structure and Nucleotide Sequences of Vicilin Genes of Cocoa and Cotton Raise Questions About Vicilin Evolution," Plant Molecular Biology 18:1173–1176, (1992).
Sagliocco, F., et al., "Sequence of an rbcS Gene From Cotton," Plant Molecular Biology 17:1725–1726, (1991).
Brown, S. M. and Crouch, M. L. "Characterization of a Gene Family Abundantly Expressed in Oenothera organensis Pollen That Shows Sequence Similarity to Polygalacturonase," The Plant Cell 2:263–274 (1990).

(List continued on next page.)

Primary Examiner—Patricia R. Moody
Attorney, Agent, or Firm—Quarles & Brady

[57] ABSTRACT

A method of genetically engineering a fiber-producing plant is disclosed. This method first comprises the step of constructing a plant expression vector that comprises a protein coding sequence and a DNA sequence capable of promoting gene expression in fiber cells, wherein the DNA sequence is homologous to a sequence selected from the group consisting of 12 different genomic sequences. The method next involves introducing the expression vector into a fiber-producing plant wherein the protein coding sequence is expressed in the fiber cells of the fiber producing plant. A method of obtaining a DNA sequence capable of promoting gene expression in fiber cells is also disclosed.

5 Claims, 9 Drawing Sheets

OTHER PUBLICATIONS

Bird, C. R., et al., "The Tomato Polygalacturonase Gene and Ripening-Specific Expression in Transgenic Plants," *Plant Molecular Biology* 11:651–662 (1988).

Giovannoni, J. J., et al., "Expression of a Chimeric Polygalacturonase Gene in Transgenic rin (Ripening Inhibitor) Tomato Fruit Results in Polyuronide Degradation but not Fruit Softening," *The Plant Cell*, 1:53–63 (1989).

SIB6-1A Gene Promoter Fragment
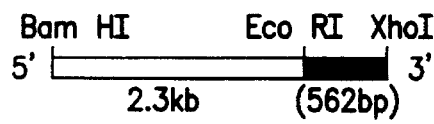
51-E9 Gene Promoter Fragment
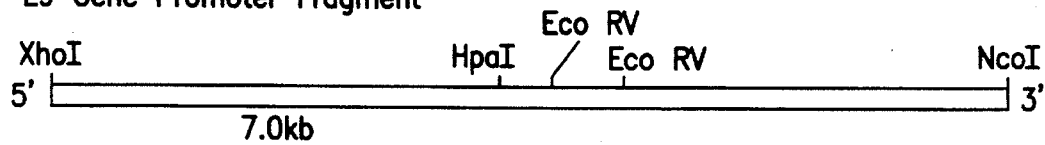
SIA-11-B Gene Promoter Fragment
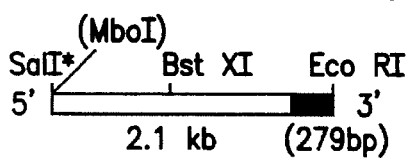
SIB8 Gene Promoter Fragment
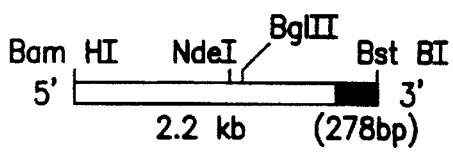
SIB12 Gene Promoter Fragment
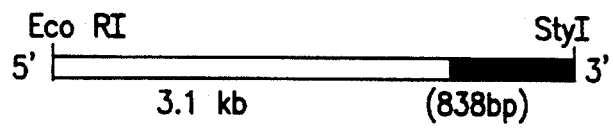
SIH6 Gene Promoter Fragment
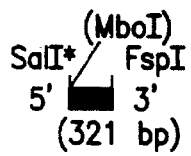
FIG. 1A
SIB6-1A Gene Promoter Fragment
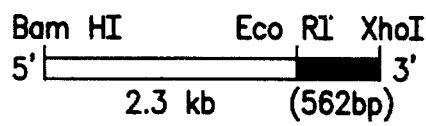
Notes:
  * = Restriction site from vector
  ■ = Sequenced region Notes:
  * = Restriction site from vector
  ■ = Sequenced region Plasmid CPE6-GUS-1

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: YES ( i v ) ANTI-SENSE: NO ( x i ) SEQUENCE DESCRIPTION: SEQ ID NO:1:

ATGCTGGTAC CTTTTTTTTT TTTTTT 26

( 2 ) INFORMATION FOR SEQ ID NO:2:

( i ) SEQUENCE CHARACTERISTICS:
        ( A ) LENGTH: 1067 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Gossypium hirsutum
        ( B ) STRAIN: Coker 312
        ( D ) DEVELOPMENTAL STAGE: 15 day old fiber cells
        ( F ) TISSUE TYPE: fiber cells ( v i i ) IMMEDIATE SOURCE:
        ( A ) LIBRARY: CKFB15A1
        ( B ) CLONE: E6

( x i ) SEQUENCE DESCRIPTION: SEQ ID NO:2:

-continued

| | | | | | |
|---|---|---|---|---|---|
| ACACACACAA | GTAAAGCATT | AGCAACCATA | GCCATGGCTT | CCTCACCAAA | ACTCTTCTCT | 60 |
| ATGTCTATCC | TCTTCCTTTT | TGCCCTCTTC | TCCATGCAAA | TCCATGCTAG | AGAGTACTTC | 120 |
| AGCAAATTCC | CAAGAGTTAA | CATCAATGAG | AAAGAGACAA | CAACCAGAGA | GCAAAAGCAC | 180 |
| GAGACCTTCG | TTCCCCAGAC | CACCCAAAAG | CCAGAAGAAC | AAGAGCCAAG | GTTCATTCCT | 240 |
| GAAACCCAAA | ATGGTTATGG | CCTTTACGGC | CACGAGTCAG | GCTCAAGCCG | GCCCAGTTTC | 300 |
| ACCACCAAAG | AAACCTATGA | ACCCTATGTC | ACCCCTGTTA | GATTCCACCC | TGATGAGCCC | 360 |
| TATAACAGCA | TCCCCGAATC | CTCCAACAAT | AAAGACACTT | ACTACTACAA | CAAGAATGCC | 420 |
| TACGAGTCCA | CTAAGCAGCA | AAACTTGGGC | GAGGCCATTT | TCACCGAGAA | AGGATGGAGC | 480 |
| ACCAAGGAAA | ACCAGAACAA | CAACTACTAC | AACGGCAACA | ATGGTTACAA | CAATGGCGAG | 540 |
| AAGCAAGGCA | TGAGCGATAC | TAGGTACTTG | GAGAATGGAA | AGTACTACTA | TGACGTCAAG | 600 |
| AGTGAGAACA | ACTATTATCC | AAACCGGTTC | GACAACTCAA | GAGGAGTTGC | TTCGAGGAAC | 660 |
| GAGTTCAATG | AGAATCGTTA | CAACAACATG | GGAAGGTACC | ACCAGAACCA | AGAGGAGTTC | 720 |
| GAGGAAAGCG | AGGAAGAGTT | CGAACCCTGA | TCACCTGTCG | TACAGTATTT | CTACATTTGA | 780 |
| TGTGTGATTT | GTGAAGAACA | TCAAACAAAA | CAAGCACTGG | CTTTAATATG | ATGATAAGTA | 840 |
| TTATGGTAAT | TAATTAATTG | GCAAAAACAA | CAATGAAGCT | AAAATTTTAT | TTATTGAGCC | 900 |
| TTGCGGTTAA | TTTCTTGTGA | TGATCTTTTT | TTTTATTTTC | TAATTATATA | TAGTTTCCTT | 960 |
| TGCTTGAAA | TGCTAAAGGT | TTGAGAGAGT | TATGTTCTTT | TTCTCTTCCT | CTTTCTTTTT | 1020 |
| TAACTTTATC | AAACAATTTT | TGAATAAAAA | TGTGAGTATA | TTGTAAC | | 1067 |

( 2 ) INFORMATION FOR SEQ ID NO:3:

( i ) SEQUENCE CHARACTERISTICS:
        ( A ) LENGTH: 913 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Gossypium hirsutum
        ( B ) STRAIN: Coker 312
        ( D ) DEVELOPMENTAL STAGE: 15 day old fiber cells
        ( F ) TISSUE TYPE: fiber cells ( v i i ) IMMEDIATE SOURCE:
        ( A ) LIBRARY: CKFB15Al
        ( B ) CLONE: H6

( x i ) SEQUENCE DESCRIPTION: SEQ ID NO:3:

| | | | | |
|---|---|---|---|---|
| TTTCACACGG | GTTGTGGCGT | AGTTTAAGCA | GAGAGGGTGC | GCAGGATAAA | 50 |
| GCTATTCACC | ATTGTTTCAA | CATGAAGGTT | TGTAATAAAA | ATTTGTTTCT | 100 |
| ATCAGCATTG | CTTTGCATTG | CTGTTGCAGG | AGTTTTGGGT | CAAGCTCCTA | 150 |
| GTAATCCTCC | TACGTCTACG | CCGGCGACAC | CCACACCACC | GGCTTCTACT | 200 |
| CCTCCTCCGA | CGACTCAAGC | ACCGCCTACA | CCAACCGCCA | CTCCGCCACC | 250 |
| GGTTTCTACT | CCTCCTCCCA | CTTCATCACC | GCCCCAGTG | ACAGCTTCTC | 300 |
| CACCCCCAGT | TTCAACTCCT | CCACCCAGTT | CTCCTCCTCC | TGCAACTCCA | 350 |
| CCACCTGCTT | CTCCTCCTCC | TGCAACTCCA | CCTCCAGCTT | CTCCACCTCC | 400 |
| TGCCACTCCT | CCACCAGCTT | CTCCACCTCC | CGCCACTCCA | CCACCTGCAA | 450 |

| | | | | |
|---|---|---|---|---|
| CCCCACCGCC | AGCAACTCCT | CCTCCTGCTA | CCCCACCACC | AGCTCCATTG 500 |
| GCTTCTCCTC | CAGCCACAGT | CCCAGCTATC | TCTCCAGTAC | AAACACCATT 550 |
| GACCTCGCCA | CCAGCTCCGC | CGACCGAGGC | CCCAGCACCT | ACCCTCGGGG 600 |
| CTGCTACGCC | AGGTCCAGCT | GGAACAGACA | CGAGCGGAGC | AAATCAAATG 650 |
| TGGACCGTAC | AAAAGATGAT | GGGAAGCTTA | GCCATGGGAT | GGGCTCTGCT 700 |
| CAATCTGATG | GTTTAAAACA | ACCGTGTGCC | TCACATTTGA | TGCCATAGCT 750 |
| GTGTAATGTT | TCATTCAATT | GCTTATTTCG | GCCTTGTTTT | TCTCGTATTT 800 |
| TATGGGCTGA | TGTCTCATAT | GGGACTTTTC | TACTATACGT | ATATGAGAGC 850 |
| CTACATTACT | TTACCATTAT | ATTGTATTCT | TTGAGACATT | ATTATTATTT 900 |
| TTTTACCTTT | TGA | | | 913 |

( 2 ) INFORMATION FOR SEQ ID NO:4:

( i ) SEQUENCE CHARACTERISTICS:
        ( A ) LENGTH: 659 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Gossypium hirsutum
        ( B ) STRAIN: Coker 312
        ( D ) DEVELOPMENTAL STAGE: 15 day old fiber cells
        ( F ) TISSUE TYPE: fiber cells ( v i i ) IMMEDIATE SOURCE:
        ( A ) LIBRARY: CKFB15A1
        ( B ) CLONE: C12

( x i ) SEQUENCE DESCRIPTION: SEQ ID NO:4:

| | | | | |
|---|---|---|---|---|
| CAACAATCAG | CAATACTCCA | AGCAACCATT | TTCCTTACAA | GTTTGTTTTT 50 |
| CTTGTGATTA | ATCCATATGG | CTAGCTCAAT | GTCCCTTAAG | CTTGCATGTC 100 |
| TGTTGGTGTT | GTGCATGGTG | GTGGGTGCAC | CCCTGGCTCA | AGGGGCCATA 150 |
| ACCCGTGCTG | ATGGCTTAGT | CGGCCTCCCA | CGCTGCCTTC | CTTTTTTGTC 200 |
| AGGGAATGGT | GATGGTGCTG | ATGCCACAGG | TTGCTGTGCC | ATCGTCATGA 250 |
| ATGCCTTGGG | ATCGCTCTGT | GGTGATACAT | AGGAACCGAT | CTAGCTTGAA 300 |
| ATCGGGTTCG | GATTTGGGTG | GAATTTCAAA | TTGGTGTGTT | ATGGAATCCC 350 |
| AACTTAATCG | TGTTTAAGGG | TGGGATCCAA | TTGTGTGATA | CATTACAGAG 400 |
| CATGGTTGTG | GATTGTTTTC | TCATATGTTT | TGATTGACTT | GCTTGCTACA 450 |
| TTGGATGATT | TGATAAGGTG | ACCAGTTTAC | CTGGGTATCC | AACCATCATC 500 |
| GGATTACTTT | TTAATAATTT | TTTGTTTCTT | GTTTATGTTG | TCTGCCTTTT 550 |
| TGTTTCTTGA | TCTATAATAT | TATATTTGGC | CAAATTTCTC | ATTTTCCAGA 600 |
| TGTAGCTTAT | ATATATATAT | TCAATAAAGT | ATATTGGTTT | AAAAAAAAA 650 |
| AAAAAAAA | | 659 | | |

( 2 ) INFORMATION FOR SEQ ID NO:5:

( i ) SEQUENCE CHARACTERISTICS:

5,495,070

(A) LENGTH: 690 base pairs
(B) TYPE: nucleic acid
(C) STRANDEDNESS: double
(D) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
(A) ORGANISM: Gossypium hirsutum
(B) STRAIN: Coker 312
(D) DEVELOPMENTAL STAGE: 15 day old fiber cells
(F) TISSUE TYPE: fiber cells ( v i i ) IMMEDIATE SOURCE:
(A) LIBRARY: CKFB15A1
(B) CLONE: B8

( x i ) SEQUENCE DESCRIPTION: SEQ ID NO:5:

```
CACCAACGGA CAATGCTTTC TCCAGCCTTA AATCGGGCAC ATTGAATTCA CTCACCGATG    60
AACAAAAAGT GGAGCTGGTG CAATTCCACA TCGTCCCAAC ATACCTCACC TCGTCTCAGT   120
TCCAAACCAT TAGCAATCCT TTGAGAACCC AAGCTGGTGA TAGTGGCGAT GGCAAGTTCC   180
CTCTCAATAT CACCACTTCG GGGAACTCCG TGAATATAAC AACAGGGTTG ACAAACACCA   240
GTGTTTCCGG CACTATTTAC ACTGATGGTC AGCTTGCTGT TTATCAAATC GATCAAGTTC   300
TTCAACCATT GCAAATATTT GCACCTAGGC CTCCAGCTCC AGCACCGGCA CCGGCAAAGT   360
CGAAGAATAA GAAGGCTACC ACCGTTGCTG ATAGCCCCGA TGTTACCCCA GCTGATAACT   420
CCAAAGCGGC CACCTTGCAA AATGTTGGTT TGTTTGGAGT TGCTGCTCTA GTTATTGCAC   480
TTTCTTTGTG ACCATGAAAA TGGAGAAAAG AAGAAGACAG TGATTTTGAT GGTGATCAAG   540
ATGGCGAGTG TTTTTTATTT TTTCAATAAT TATCATTTAA AAAATTTATG TTCTGTATGA   600
ANGATTGAAT TTGAGTTTG TCTTGTTGAT TTCATTTATT TTTGTTTTGA AATTTTCTTT   660
GTTATCTCTT ATTTCTCAAT TGTAATTGTG                                   690
```

( 2 ) INFORMATION FOR SEQ ID NO:6:

( i ) SEQUENCE CHARACTERISTICS:
(A) LENGTH: 727 base pairs
(B) TYPE: nucleic acid
(C) STRANDEDNESS: double
(D) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
(A) ORGANISM: Gossypium hirsutum
(B) STRAIN: Coker 312
(D) DEVELOPMENTAL STAGE: 10 day old fiber cells
(F) TISSUE TYPE: fiber cells ( v i i ) IMMEDIATE SOURCE:
(A) LIBRARY: CKFB10
(B) CLONE: B12

( x i ) SEQUENCE DESCRIPTION: SEQ ID NO:6:

```
ATAACCGTGA CAGCCACCAA CTTTTGTCCA CCTAACTATG CTTTATCTAG    50
TGACAATGGC GGGTGGTGCA ATCCCCACG AGAACACTTT GATTTGGCCG   100
AACCGGCATT CTTGCGGATA GCAGAATATC GAGCTGGAAT CGTCCCTGTT   150
```

```
ATGTTCAGAA  GGGTGTCATG  TGTGAAGAAA  GGAGGCATCA  GGTACACCAT   200

GAATGGACAT  TCGTACTTCA  ACATGGTGTT  GATAACGAAC  GTGGGAGGGG   250

CAGGGGATAT  AACGTCAGTG  TCCATCAAGG  GTTCCAGAAC  AGGATGGCTA   300

CCTATGTCCA  GAAATTGGGG  CCAAAACTGG  CAGAGCAATG  CTTACCTTAA   350

CGGACAAAGC  CTCTCTTTTA  AAGTGACTGC  CAGCGATGGC  AGGACTATCA   400

CAGCCTACAA  TGTAGTGCCT  GCTGGTTGGC  AATTCGGACA  AACTTTTGAA   450

GGAGGCCAGT  TTTAAGACAA  TATTATAGTG  TCTGTCTAAT  ATAAAACTGG   500

AATTGACATA  TTACTTATAT  AAGGCACATG  AGCGTTTTAT  GCCGAGGTAG   550

CAAAATGGCG  CCCGCTGGCT  TTATGTGTGA  AATAGGCGAG  CAAGTGCCAT   600

TAGCCTATAA  TCTATACATT  TCTTATAGTG  AACCAAACTA  TTAAGTTTGA   650

ACTCTAGAGG  ATATATCCAT  AATGTCTGAA  ATTTGTTTGT  TGATGATTGA   700

CCATGATATT  TATGCTTTTC  ATTATTG                              727
```

( 2 ) INFORMATION FOR SEQ ID NO:7:

( i ) SEQUENCE CHARACTERISTICS:
    ( A ) LENGTH: 989 base pairs
    ( B ) TYPE: nucleic acid
    ( C ) STRANDEDNESS: double
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Gossypium hirsutum
    ( B ) STRAIN: Coker 312
    ( D ) DEVELOPMENTAL STAGE: 10 day old fiber cells
    ( F ) TISSUE TYPE: fiber cells ( v i i ) IMMEDIATE SOURCE:
    ( A ) LIBRARY: CKFB10
    ( B ) CLONE: A11

( x i ) SEQUENCE DESCRIPTION: SEQ ID NO:7:

```
TAAAAGGATA  GCATCTGCCC  TTACAAAGAT  GAAAATACAA  GCAAAATCGA    50

AGACTTCAGA  GATCATCCTT  AAAAGTTGAA  CACAAAGTTA  ACTTGAAATA   100

CCAGCTAAAG  TGATAATAAA  ACTCGACCAT  AGAATTTCGG  AAACTTCGAA   150

ACATTCACCA  AATAAAACCG  TCCCTCGAAT  TTCAACTATC  AAACAGTAAG   200

GCTCAACTCA  CAAAAGCCTT  GGAAAGAGGT  ACACAAATGT  TTATCCTAC    250

TTATTCATTC  AATCAATAAA  ATAAATGGAA  CATGAACTCC  ATCCTCCTTG   300

GTTTGACAAT  ACCAGCTTTC  ACAATTAAGA  TTCTATACCA  GATTCATGAG   350

CTTGAACGGA  ATCACTCTGA  AACAATTACT  ACATGTAACA  ATGGAAACGA   400

AATGGAAAAA  CAAAAAAAAG  TTGGTTTAAT  TAATTATTAG  TTACCCTTGA   450

AGACCTTGGC  ATTGGTGGAG  TAACTCTTGG  CATGAAAGTC  TGAGAACAAG   500

TAGAGAAGAG  AGACGTTGAA  GGCTCCATTG  AAACACCAAC  TCAGAATCCC   550

AGAGCAGCCA  GAAGCAGTGA  AGTGGTAGAA  CACAAGCATG  GCCATGATCA   600

AAAAGCTTAA  CCGGAACTGC  ACCAGTTGAA  AATCCGTCAC  CATTTTCTTC   650

CACTTGGGGT  GCATCCCCAG  GGTGCACAAC  AGGTAATAGG  AGTACATTAC   700

GACATGCACC  ACGCAGTTGG  TGATCAGCAC  CATGGGTACG  GAGGACTGAG   750
```

| CACTGTCTAA | GCAAATATAA | CACATGATGA | CCACCATGGA | GTGATGGTAG | 800 |
| ACGTGAAGGA | AGGATAGCCT | CTTCATGGAT | CCGCTGAGGA | TGATCAAAAG | 850 |
| GGTGTCCATG | AATTCAACAA | TCTTGGAGAG | GTAGAAGATG | TATGCCCAGA | 900 |
| AAAAGAGAGG | GCCCGATGGG | GATGTACCCC | TAGGGAAGCA | AACGAGGGTG | 950 |
| TTGAAGTTAG | GCACCTGGGA | GAAGATGGAA | ACGAGGCAA | | 989 |

( 2 ) INFORMATION FOR SEQ ID NO:8:

( i ) SEQUENCE CHARACTERISTICS:
        ( A ) LENGTH: 498 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Gossypium hirsutum
        ( B ) STRAIN: Coker 312
        ( D ) DEVELOPMENTAL STAGE: 10 day old fiber cells
        ( F ) TISSUE TYPE: fiber cells ( v i i ) IMMEDIATE SOURCE:
        ( A ) LIBRARY: CKFB10
        ( B ) CLONE: D7

( x i ) SEQUENCE DESCRIPTION: SEQ ID NO:8:

| CAATATTTGC | TGTGGCCATG | TTTGTTGTGT | CCGGGACCAT | GGCACAGGAT | ATTGCTCCTT | 60 |
| CTCCTGCAAT | GGCTACCGGA | GCAGGCTCTG | CTTTGCCGGT | TTCCGCTGTC | TTCTTATGCT | 120 |
| CTTCCATGTT | GGTCTCTTTA | ATTGCTCTCT | TGGTGCATTG | AATTCAAAGC | TTTTCAAGAC | 180 |
| TTTATGACAT | TGGCTACCCT | TAATTTCACT | CTCACTGGTG | ATGAGGGAG | TAGCCTCTAA | 240 |
| TCTTCTCCGA | GATAATATTT | GGGTGTTATC | AATTTTCAAT | TTCTCTAAAG | TTTTAAATAT | 300 |
| CTCTATATAT | ATCATGTTAC | ATTAGTGACA | TAAATTTGAT | TTTGTAATGT | AATTGGTGTG | 360 |
| ATTTTCTTAT | ATATCATAGA | TATATAAGGG | TATTGATCCT | ATTTCTTTTG | TATTCATATT | 420 |
| ATGCAGTTTG | CTTTGCTTTG | CCTTTTGTAA | TAATAATTTT | TTTTGGGTG | GTTGAAAAAA | 480 |
| AAAAAAAAAA | AAAAAAA | | | | | 498 |

( 2 ) INFORMATION FOR SEQ ID NO:9:

( i ) SEQUENCE CHARACTERISTICS:
        ( A ) LENGTH: 668 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Gossypium hirsutum
        ( B ) STRAIN: Coker 312
        ( D ) DEVELOPMENTAL STAGE: 10 day old fiber cells
        ( F ) TISSUE TYPE: fiber cells ( v i i ) IMMEDIATE SOURCE:
        ( A ) LIBRARY: CKFB10
        ( B ) CLONE: C2

( x i ) SEQUENCE DESCRIPTION: SEQ ID NO:9:

| | | | | | |
|---|---|---|---|---|---|
| TTTTTTAAAC | AAAAGCATAG | TAGTTTTTAT | ACCCCACTGG | TGAAGAATGA | 50 |
| CAAACACAGT | TTCCAAATTC | AAATGCATCA | TCTAAACAAA | TATGCCCCTT | 100 |
| TCTTAGTCTT | ATCTGCATGG | TTTTGCTTGC | TGGAAATGAA | AAAGCAAAAA | 150 |
| TGAAAGAAAA | AGAAAAAAGG | TGAAAACAAC | CTTCAAGGTT | TAAGAGATGA | 200 |
| TATGTAATTT | TTCACTTTTT | TCAACGCATT | GCAGCAAGAG | GGTTCCTTTT | 250 |
| CCATTGCAGA | GGCTGATATG | TCTTCTCTGT | TTCCTCTATT | TTAGTCCATG | 300 |
| GTAATTTGTG | TTTAGCCACC | TTTCGCTTCC | TAGCTGATAC | TCCCAGATAG | 350 |
| TCTCCAGCGT | TCTTGAGGCA | GAGTCCTTCT | TGGACATCAC | AAATGGGGTA | 400 |
| ATCACTAGGG | CAGCAGTATT | CAGTTCCAGT | ACAGCAAACA | GCATTTTCAT | 450 |
| ATTCACAGCA | GCCGTATATT | AGGCAATAAT | CATAGAATTC | AAAAAGGCAA | 500 |
| CAGCATGTCT | CATCACTTGA | ACAATAGGAA | AAGTCTCCAC | AATCACTTGG | 550 |
| TGAAGGAGAT | GGAGGTGGTG | GTGGTGGTGG | AGTTGAAGGA | GGTGGCGGTG | 600 |
| GAGGAACACT | TGGCGATGGA | TAAGGGGATG | GTGAAGAGGA | TTGTTTAGTT | 650 |
| GGATAAGAAG | CCATGGCA | | | | 668 |

( 2 ) INFORMATION FOR SEQ ID NO:10:

( i ) SEQUENCE CHARACTERISTICS:
        ( A ) LENGTH: 570 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Gossypium hirsutum
        ( B ) STRAIN: Coker 312
        ( D ) DEVELOPMENTAL STAGE: 10 day old fiber cells
        ( F ) TISSUE TYPE: fiber cells ( v i i ) IMMEDIATE SOURCE:
        ( A ) LIBRARY: CKFB10
        ( B ) CLONE: C12

( x i ) SEQUENCE DESCRIPTION: SEQ ID NO:10:

| | | | | | |
|---|---|---|---|---|---|
| TATCAACTAC | CAACCACCCA | CTGTTGTCCC | TGGTGGTGAT | CTCGCCAAGG | TCCAGAGAGC | 60 |
| TGTTTGCATG | ATTTCTAACT | CCACCAGTGT | TGCTGAAGTC | TTCTCTCGCA | TTGACCATAA | 120 |
| GTTTGATCTT | ATGTACGCCA | AACGTGCCTT | CGTTCACTGG | TATGTTGGTG | AGGGTATGGA | 180 |
| AGAAGGAGAA | TTCTCAGAGG | CTCGTGAGGA | TCTTGCTGCA | TTGGAGAAGG | ATTATGAAGA | 240 |
| AGTTGGTGCT | GAGTCAGCTG | AGGGTGATGA | GGGTGAAGAT | GATGAGTACT | AAGAAGTACG | 300 |
| TGTGATTGAG | TGTGCTTACG | ATGTCTTTTA | TTACCTGTTG | CTTCCGTGTT | ATGCAAGCTT | 360 |
| CTATTCTTTG | AAGCTTGTTA | AAGACTTGAA | ATGGTTTACT | GTATGTTATG | CTGTTTTATG | 420 |
| TTTTATTTGT | GTTTGGGTTG | AAACTTGATA | TTTTTGTTGG | GTGTATTTGA | AAGTAAATTG | 480 |
| TTAAGGGAAC | TTGTGAATGC | TCAACAGGTA | TAAAAAAAAA | AAAAAAAAA | AAAAAAAAA | 540 |
| AAAAAAAAA | AAAAAAAAA | AAAAAAAAA | | | | 570 |

( 2 ) INFORMATION FOR SEQ ID NO:11:

(i) SEQUENCE CHARACTERISTICS:
  (A) LENGTH: 432 base pairs
  (B) TYPE: nucleic acid
  (C) STRANDEDNESS: double
  (D) TOPOLOGY: linear (ii) MOLECULE TYPE: cDNA (iii) HYPOTHETICAL: NO (iv) ANTI-SENSE: NO (vi) ORIGINAL SOURCE:
  (A) ORGANISM: Gossypium hirsutum
  (B) STRAIN: Coker 312
  (D) DEVELOPMENTAL STAGE: 10 day old fiber cells
  (F) TISSUE TYPE: fiber cells (vii) IMMEDIATE SOURCE:
  (A) LIBRARY: CKFB10
  (B) CLONE: C1

(xi) SEQUENCE DESCRIPTION: SEQ ID NO:11:

```
TTTCATTTCA  CTATATACAC  ACACACATAC  ACAAACCAAG  CAACCATGGA   50
TACAAGAAGC  AAAACACCTA  ATGAACCATA  GCTGCTTTAT  TCTAATAGTA  100
AAAACCCAAA  TACATCATAT  ATTATTTAGA  TCAGCTTCCA  TAATATGCTT  150
AGCTTTTTTT  TCTCATTTAC  AATTGCAAGG  GTTGCAAGTG  CAGTTATCTC  200
CACATTTGCA  GCCATTTTCA  GCCCCAGTTT  CCATTTCAGC  TCCATCAAAG  250
TGCACTTTCC  GGGGTGCCAC  GCCAAGAACA  AGTGTCCCGG  TTGTGGTTTG  300
CTCAGCAAAG  TTCATCTCAG  GGTACATCTT  GCAACCGCCG  CAGCCGCTGC  350
CGCACTTGCA  ACCGGAGCCG  CAACCGCAGT  TTCCACCACA  GCAAGACATT  400
TTTCTTCACC  TCACTGATCA  CTAAAGGGCG  AT                      432
```

(2) INFORMATION FOR SEQ ID NO:12:

(i) SEQUENCE CHARACTERISTICS:
  (A) LENGTH: 320 base pairs
  (B) TYPE: nucleic acid
  (C) STRANDEDNESS: double
  (D) TOPOLOGY: linear (ii) MOLECULE TYPE: cDNA (iii) HYPOTHETICAL: NO (iv) ANTI-SENSE: NO (vi) ORIGINAL SOURCE:
  (A) ORGANISM: Gossypium hirsutum
  (B) STRAIN: Coker 312
  (D) DEVELOPMENTAL STAGE: 10 day old fiber cells
  (F) TISSUE TYPE: fiber cells (vii) IMMEDIATE SOURCE:
  (A) LIBRARY: CKFB10
  (B) CLONE: A8

(xi) SEQUENCE DESCRIPTION: SEQ ID NO:12:

```
CAATCAAATT  AACTTAAAAG  AAGTGATATT  CAGGATACAA  GGCCAATGCC  AAACAGATTC   60
AACACAAACA  TAAGCTGCAT  ACATATAGGC  AACTTGAAGT  TATTGAATAG  ACGGGATTCA  120
GAGAACAAAG  CTGGTTAAAA  CATGAGGTAC  GATACAGATA  TTACATTGGC  ATGTTCTTCA  180
GAAGATTTTT  TTGGATGGCT  AAGTGGAACC  ACCAATTTTG  GGATGATCTG  GAGGTGAGGG  240
TTTTGGGATG  TAGGGAATAA  GAGGAGTACC  ATGCTCAATA  GGACCAGGTT  TTATGGATGC  300
```

```
TTTGGAGCTT GGAACTGGAT                                                              320
```

( 2 ) INFORMATION FOR SEQ ID NO:13:

( i ) SEQUENCE CHARACTERISTICS:
        ( A ) LENGTH: 399 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Gossypium hirsutum
        ( B ) STRAIN: Coker 312
        ( D ) DEVELOPMENTAL STAGE: 10 day old fiber cells
        ( F ) TISSUE TYPE: fiber cells ( v i i ) IMMEDIATE SOURCE:
        ( A ) LIBRARY: CKFB10
        ( B ) CLONE: A9

( x i ) SEQUENCE DESCRIPTION: SEQ ID NO:13:

```
TCAACTCCGC CGCCCAAACA ACACCAGACC GGCAAGCAGC TTGCAAATGC ATCAAAAGTG    60
CGGCCGCCGG CATTTCTGGC ATCAACTATG GTATTGCAAG CGGACTCCCA GGCAAGTGCG   120
GTGTCAACAT CCCTTACAAG ATCAGCCCTA GCACTGACTG CAACAGCGTC AAGTGAAGTT   180
TTGGCATGGA AAGTTCACCA GCTAGTGGAA GCCAAAATAA CGATAGCTAC AGAATAAATA   240
TGGATGTTAA AATTCCAGAG TTGTGGGTTG TGTACTATGC CGCTTTATGC GACTACGTAA   300
TATTAACTTT ATCTACAAAT TAATATCACT CGTCTCCATT TCCCATTTTA AAAAAAAAA    360
AAAAAAAAAA AAAAAAAAAA AAAAAAAAA  AAAAAAAA                          399
```

( 2 ) INFORMATION FOR SEQ ID NO:14:

( i ) SEQUENCE CHARACTERISTICS:
        ( A ) LENGTH: 455 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Gossypium hirsutum
        ( B ) STRAIN: Coker 312
        ( D ) DEVELOPMENTAL STAGE: 10 day old fiber cells
        ( F ) TISSUE TYPE: fiber cells ( v i i ) IMMEDIATE SOURCE:
        ( A ) LIBRARY: CKFB10
        ( B ) CLONE: D4

( x i ) SEQUENCE DESCRIPTION: SEQ ID NO:14:

```
AGCAGCTGTG CCTAGTCCTT CTACTATGCC TAGAGCTTGG ACTTTCTTCC    50
TACTCGATCA GATTCTAACA TACGTAATCT TGGGAGCTGC TGCTGTTTCA   100
ACCGAGGTGC TTTACTTAGC AAACAAAGGA GACTCAGCCA TCACTTGGAG   150
TGCAGCTTGT GGGACATTTG CTGGTTTCTG TCATAAAGCC ACAATAGCCG   200
TGGTGATCAC GTTTGTTGCA GTCATTTGTT ATGCGGTGCT ATCACTGGTC   250
```

```
TCTTCTTATA GACTTTTCAC CAAGTTTGAT GCCCCAGTGA ACTACCCCAG    300

TAAGACCATA GAAGCTACTG TTTTCCATGG TTGATTTATG TTATTACTGA    350

AATTAATTTA CCTTATATTT TCATGTTCTG CTTGTAATAA TAATAAAAAA    400

GGTTGCTTAC AGTGTGTTTA TGTTATATGA TTAAATAGAG GTGTTGTCTT    450

TGGTG                                                    455
```

( 2 ) INFORMATION FOR SEQ ID NO:15:

( i ) SEQUENCE CHARACTERISTICS:
        ( A ) LENGTH: 1080 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Gossypium hirsutum
        ( B ) STRAIN: Coker 312
        ( D ) DEVELOPMENTAL STAGE: 10 day old fiber cells
        ( F ) TISSUE TYPE: fiber cells ( v i i ) IMMEDIATE SOURCE:
        ( A ) LIBRARY: CKFB10
        ( B ) CLONE: B6

( x i ) SEQUENCE DESCRIPTION: SEQ ID NO:15:

```
ACTACTCAAC TTTCTCTCTG AATTCCTCCA AGTTAGGAGT TTGGAGAGTG     50

GTCACCGCTG AAGCAAAACA AATTTCTTGG GGGAAAAGAA AATGGAGTTT    100

TCCATGATTT TTATGATTAG CTTCTCTGTA TTGATTTTGT GCTCCTCACT    150

GGCATATGGT CAAGTTGCAA TGAGCACAAA CCCGACACCG TCACCCTCAC    200

CAGCACCGGC ACCGACACCG GCATACACAA ATATCAAAGA CTTACTCTCT    250

GTGGCAGGTC CATATCACAA GTTCCTGGGC TACCTCGAGT CGACTAAATT    300

AATCGACACG TTCCAAATCC AAGCCAACAA CACGGTTGAA GGCATTACGA    350

TTTTCGTACC GAAAGACAGC GCATTCAAGG CTCTTACGAA GCCTTCATTG    400

TCAAATCTAA CTGATGATCA GTTCAAATCA GTGCTCCTTT ACCATGCCTT    450

GCCACGATAC TATGCCCTTG CGGACTTCAA TGACCTAAGT GAGAAAGGCC    500

CTATTAGTAC ACTTGCTGGT GGCCAATACA CTTTGCAATT CAACGATGAG    550

TCTGGTACCG TCCGCCTCGA TTCCGGATGG AGCAAAACAA AAGTCACTAG    600

CGCAGTACAT ACGTCCAAGC CAGTCGCAGT CTATCAAATC GATAAGGTCC    650

TTCTTCCGGA GGCCATTTTC GGGACCGACA TACCTCCGAC ACCTGCACCT    700

GCCCCGGCTC TTGGTATTGG CCCATCAGCT GACACTCCAT CAGCAGCAAA    750

ATCCGAAGAA ACTGGTTCCT CATCAAAGCC TTCGTTTTCG GGTTCATCAT    800

CTCCTAGGAT CATGATGAAC TCGGGCATTT GGACTCAGCT GGTTTTGGCA    850

TTCTTAGGTG GATGGCTGGT TCTCTTTTTC TGAGACGTTA TAATTTTATG    900

TTGAAAGGGG GGCACATATG GGGTTCTCAA TTTTCTGTGA TTTTTAGACC    950

CCATTTTCTT TCATATATAT GTTACTGTGT GTTATTATAA AAAGAATGTT   1000

ATTGTGTGTT AAGAATATGG TTGTGTTATA ATTACCATTT CAATTTTAAT   1050

GGAGTTTTGC CTTAAAAAAA AAAAAAAAA                          1080
```

(2) INFORMATION FOR SEQ ID NO:16:

(i) SEQUENCE CHARACTERISTICS:
        (A) LENGTH: 868 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Gossypium hirsutum
        (B) STRAIN: Coker 312
        (D) DEVELOPMENTAL STAGE: 10 day old fiber cells
        (F) TISSUE TYPE: fiber cells (vii) IMMEDIATE SOURCE:
        (A) LIBRARY: CKFB10
        (B) CLONE: A12

(xi) SEQUENCE DESCRIPTION: SEQ ID NO:16:

```
CAACGATACT  TCAAATACTA  ATACATTTAT  CACCAAACCA  TTGTGATACA   50
GAAAGTAATA  TCATTTTATC  CATTACCAAG  AACATGATTC  ATGGATAGAT  100
TTCACATAAC  TAAACTCGTG  GGTATATTAT  TATAGAACAA  ACTGGATATT  150
GCTTTAAGCT  GTTTAATGC   ACACTATGAT  GAAACTTATA  GTGTATGAAT  200
CTACTCTTCA  GGATTTTTAC  TTAGGGACCC  AAACAATGTG  ATCCCGAGGA  250
AGGAAATGGC  AGACAGGAAT  GGTTCCTGGT  TCAACTTTTA  GGACTTGAAA  300
AGCCAAATGC  TTAGGGTTCC  ATGCTGATGT  ATCTGTGTGG  CAGACTGCTA  350
CTGCTTTGGC  TTTTGTTCCG  TCAGCACCCT  CTAAAGGAAC  CATGTAAGCC  400
CTTGTTGTTT  CTGATTTATG  GCAATAGAAG  ACAGCATATG  CATAATTCTG  450
CTTGTGGCAC  ACTACGGCTT  TGTCATCTGT  CATCTTCTGC  ACTCCAGCTG  500
CTATTGTATA  CTTTTGCATT  GGGGTTTGTT  TTTCCACTTC  TGTTGAGACT  550
GCCTGATCAA  CTTTCCCTAG  TTTGGAAATG  CTATAGTCAA  TCATTGACTC  600
CAGTGAGGTT  GCACAATATT  TTTCCTCTCC  TTCAATCGCT  GGCTGTTCGC  650
ACTCCTTAAT  TGTGTTCTTC  ATCATCTCTG  CCTTCAGTGA  TCCAGGTTTC  700
ACTGAAAACT  TGTTGAAAAT  TTCTGGCAAC  TTGTCAGATG  AAAACGGTAT  750
TTTTTGGGCA  GTTTGATAAG  GTAAGAAAGC  TGATTTCTCT  GTATTTTCAG  800
TGAAATGCAG  GCTCATTGTT  GCCCCGGGGT  GCATATCCTT  TTCCAGAAAG  850
AAAAGAGCCA  CATTCGGG                                        868
```

(2) INFORMATION FOR SEQ ID NO:17:

(i) SEQUENCE CHARACTERISTICS:
        (A) LENGTH: 1283 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:

(A) ORGANISM: Gossypium hirsutum
(B) STRAIN: Coker 312
(D) DEVELOPMENTAL STAGE: 15 day old fiber cells
(F) TISSUE TYPE: fiber cells (vii) IMMEDIATE SOURCE:
(A) LIBRARY: CKFB15
(B) CLONE: E9

(xi) SEQUENCE DESCRIPTION: SEQ ID NO:17:

| | | | | | |
|---|---|---|---|---|---|
| ACACACAAAT | ACACTAAAAA | TTCTTTGCTT | TCTATTTTGT | AAACCATGGC | 50 |
| TCATAACTTT | TGTCATCCTT | TCTTCCTTTT | CCAACTTTTA | CTCATTACTG | 100 |
| TCTCACTAAT | AATCGGTAGT | CACACCGTCT | CGTCAGCGGC | TCGACATTTA | 150 |
| TTCCAGACAC | AAACAACCTC | ATCAGAGCTG | CCACAATTGG | CTTCAAAATA | 200 |
| CGAAAAGCAC | AAAGAGTCTG | AATACAAACA | ACCAAAATAT | CACGAAAAGT | 250 |
| ACCCAAAACA | TGAGAAGCCT | AAAATGCACA | AGGAGGAAAA | ACAAAAACCC | 300 |
| TGCAAACATC | ATGAAGAGTA | CCACGAGTCA | CGCGAATCGA | AGGAGCACGA | 350 |
| AGAGTACGAT | AAAGAAAAAC | CCGATTTCCC | CAAATGGGAA | AAGCCTAAAG | 400 |
| AGCACAAGAA | ACACGAAGTT | GAATATCCGA | AAATACCCGA | GTACAAGGAC | 450 |
| AAACAAGATG | AGGATAAGGA | ACATAAAAAT | GAAGAGTACC | ATGAATCACG | 500 |
| CGAATCGAAG | GAGCACGAAG | AATACGAGAA | AGAAAAACCC | GAGTTCCCCA | 550 |
| AATGGGAAAA | GCCTAAAGAG | CACGAGAAAC | ACGAAGTCGA | ATATCCGAAA | 600 |
| ATACCCGAGT | ACAAGGAAAA | GCAAGATAAG | AGTAAGGAAC | ATAAAGATGA | 650 |
| AGAGTGCCAC | GAGTCACACG | AATCGAAAGA | TCACGAAGAG | TACGAGAAAG | 700 |
| AAAAACCCAA | TTTCTTCAAA | TGGGAAAAGC | CTAAAGAGCA | CGAGAAACAT | 750 |
| AAAGCCGAAT | ATCCAAAAAT | ACCCGAGTGC | AAGGAAAAAC | AAGATGAGGA | 800 |
| TAAGGAAGAT | AAACATGAGT | TCCCAAAGCA | TGAAAAAGAA | GAGGAGAAGA | 850 |
| AACCTGAGAA | AGGCAGAGTA | CCCTGAGTGG | GTTAAAATGC | CTGAATGGCC | 900 |
| GAAGTCCATG | TTTACTCAGT | CTGGCTCGAG | CATTAAGCCT | TAAGCCATAT | 950 |
| GACACTGGTG | CATGTGCCAT | CATCATGCAG | TAATTTCATG | GGATATCGTA | 1000 |
| ATTATATTGT | TAATAAAAAA | GATGGTGAGT | GGGAAATGTG | TGTGTGCATT | 1050 |
| CATCCATGTA | GCAATGCTGA | ATCTCTTTGC | ATGCATAGAG | ATTCTGAATG | 1100 |
| GTTATAGTTT | ATGTTATATC | GTTTGTTCTA | GTGAAATTAA | TTTTGAATGT | 1150 |
| TGTATCTAAT | GTTAACATCA | CTTGGCTTGA | TTTATGTTTT | AATGAAGTTT | 1200 |
| ATGTTGTGTA | TTTTACTTTA | ATGATATTCC | ATGTATTGTT | AATTTAAAAA | 1250 |
| AAAAAAAAA | AAAAAAAAA | GGCCGAATTG | GCA | | 1283 |

(2) INFORMATION FOR SEQ ID NO:18:

(i) SEQUENCE CHARACTERISTICS:
(A) LENGTH: 878 base pairs
(B) TYPE: nucleic acid
(C) STRANDEDNESS: double
(D) TOPOLOGY: linear (ii) MOLECULE TYPE: cDNA (iii) HYPOTHETICAL: NO (iv) ANTI-SENSE: NO (vi) ORIGINAL SOURCE:
(A) ORGANISM: Gossypium barbadense (B) STRAIN: Sea Island (vii) IMMEDIATE SOURCE:
(A) LIBRARY: SIFB10
(B) CLONE: H8

(xi) SEQUENCE DESCRIPTION: SEQ ID NO:18:

| | | | | | | |
|---|---|---|---|---|---|---|
| AAAAAGGGGA | AGAGCTAATG | GAAAAAAGTG | AAAAGGGTAA | TGGTTTTGCT | CCTGCTACAA | 60 |
| GGTCTCCAAT | GGCTTTAATG | GGGTCATCTA | GAAATGAAAA | CCAAGAAGTG | AATACCAGCA | 120 |
| TGAGAACTGC | CGAGACCATG | CTGCGGTTGG | TGCCTATGGC | TTTAGGGGTT | GCTGCACTTG | 180 |
| TTGTCATGCT | CAAAAACTCA | CAGTCCAATG | ACTTTGGCTC | CGTTTCATAC | TCAGATCTTG | 240 |
| GTGCTTTCAG | GTACTTGGTG | CATGCTAATG | GTATTTGTGC | AGGCTATTCC | CTTCTTTCAG | 300 |
| CTATTATAGC | AGCTGTGCCT | CGTCCTTCTA | CTATGCCTAG | AGCTTGGACT | TTCTTCCTAC | 360 |
| TCGATCAGAT | TCTAACATAC | GTAATCTTGG | GAGCTGCTGC | TGTTTCAACC | GAGGTGCTTT | 420 |
| ACTTAGCAAA | CAAGGAGAC | TCAGCCATCA | CTTGGAGTGC | AGCTTGTGGG | ACATTTGCTG | 480 |
| GTTTCTGTCA | TAAAGCCACA | ATAGCCGTGG | TGATCACGTT | TGTTGCAGTC | ATTTGTTATG | 540 |
| CGGTGCTATC | ACTGGTCTCT | TCTTATAGAC | TTTTCACCAA | GTTGATGCC | CCAGTGAACT | 600 |
| ACCACAGTAA | GACCATAGAA | GCTACTGTTT | TCCATGGTTG | ATTTATGTTA | TTACTGAAAT | 660 |
| TAATTTACCT | TATATTTTCA | CGTTCTGCTT | GTAATAATAA | TAAAAAAGGT | TGCTTACAGT | 720 |
| GTGTTTATGT | TATATGATTA | AATAGAGGTG | TTGTCTTTGG | TGCTTCTTTT | GTAATCTTCA | 780 |
| GACTGCTTAC | TAGAATCCCT | TTTAGGTTGC | ATCATTGGTA | TCATGTAATG | TCAAAAATGA | 840 |
| AAAAGATTT | ATAAGTGACA | GCACAAAATG | CAAAAAA | | | 878 |

(2) INFORMATION FOR SEQ ID NO:19:

(i) SEQUENCE CHARACTERISTICS:
(A) LENGTH: 1603 base pairs
(B) TYPE: nucleic acid
(C) STRANDEDNESS: double
(D) TOPOLOGY: linear (ii) MOLECULE TYPE: cDNA (iii) HYPOTHETICAL: NO (iv) ANTI-SENSE: NO (vi) ORIGINAL SOURCE:
(A) ORGANISM: Gossypium barbadense
(B) STRAIN: Sea Island (vii) IMMEDIATE SOURCE:
(A) LIBRARY: SIFB10
(B) CLONE: H4

(xi) SEQUENCE DESCRIPTION: SEQ ID NO:19:

| | | | | | | |
|---|---|---|---|---|---|---|
| ATCTCATATT | CCGGAAGGCG | TCTTGATACA | CGCCCTCATT | TATTTTATTT | TTCAAACAAA | 60 |
| TTTTCCCTTC | AGTTTTCGTA | TAATTTCCTA | GGAAAAGAAA | AATGAGAGAG | TGCATTTCAG | 120 |
| TTCACATTGG | TCAGGCCGGT | ATTCAGGTCG | GAAATGCTTG | CTGGGAACTT | AGTGTCTCGA | 180 |
| GCATGGCATT | CAGCCTGATG | CCAAATGCC | AAGTGATAAG | ACTGTTGGTG | GAGGAGACGA | 240 |
| TGCTTTCAAC | ACCTTTTTCA | GCGAAACTGG | TGCCGGGAAG | CACGTCCCTC | GCGCCATCTT | 300 |
| TGTTGATCTG | GAGCCTACTG | TTATCGATGA | AGTGAGGACT | GGTACGTACC | GCCAGTTGTT | 360 |
| CCACCCTGAG | CAACTCATCA | GTGGCAAAGA | AGATGCTGCC | AACAATTTCG | CTCGTGGCCA | 420 |
| TTATACAATT | GGCAAAGAGA | TTGTTGATCT | CTGCTTGGAT | CGTATCCGAA | AACTTGCTGA | 480 |
| TAACTGTACT | GGGCTCCAAG | GCTTCTTGGT | TTTCAATGCT | GTTGGTGGTG | GTACTGGTTC | 540 |

| TGGTCTTGGA | TCTCTTCTCT | TGGAGCGTCT | CTCTGTTGAC | TATGGAAAGA | AGTCGAAGCT | 600 |
| TGGTTTCACT | GTCTATCCTT | CACCTCAGGT | TTCTACATCA | GTTGTAGAGC | CTTACAACAG | 660 |
| TGTGCTGTCC | ACTCATTCGC | TCCTTGAGCA | CACTGATGTC | GCTGTTCTTC | TGGATAACGA | 720 |
| AGCAATATAT | GACATCTGCA | GCTGCAGGCG | TTCTTTGGAC | ATTGAACGAC | CCACTTATAC | 780 |
| CAATCTTAAC | CGCCTTGTCT | CTCAGGTTAT | CTCATCTCTT | ACCGCATCTT | TGAGGTTTGA | 840 |
| TGGAGCCCTG | AATGTGGATG | TGACTGAGTT | CCAGACTAAC | CTGGTCCCAT | ATCCCAGGAT | 900 |
| CCACTTTATG | CTTTCTTCTT | ATGCCCCTGT | CATTTCAGCT | GAGAAGGCTT | ACCATGAGCA | 960 |
| GCTATCGGTG | GCTGAGATAA | CCAACAGTGC | TTTTGAACCC | TCTTCAATGA | TGGCCAAATG | 1020 |
| TGACCCACGA | CACGGGAAGT | ACATGGCTTG | CTGCCTTATG | TACCGAGGAG | ATGTTGTGCC | 1080 |
| CAAAGATGTG | AATGCGGCTG | TGGCCACCAT | TAAGACCAAA | CGCACAATCC | AATTTGTGGA | 1140 |
| TTGGTGCCCT | ACTGGATTCA | AGTGCGGTAT | CAACTACCAG | CCACCAACTG | TTGTTCCAGG | 1200 |
| AGGGGACCTT | GCCAAGGTTC | AGAGAGCTGT | CTGCATGATC | TCCAACTCAA | CCAGCGTTGC | 1260 |
| GGAAGTGTTT | TCCCGCATTG | ATCATAAATT | TGATCTCATG | TATGCCAAGC | GTGCATTTGT | 1320 |
| GCACTGGTAT | GTTGGTGAGG | GCATGGAGGA | AGGAGAGTTT | TCTGAGGCAC | GTGAAGATCC | 1380 |
| TCGCTGCACT | GGAAAAAGAT | TATGAAGAAG | TTGGCGCTGA | GTCTGGTGAA | GGAGACGAAG | 1440 |
| GGGATGAGGA | GGAGTATTGA | GGGATGTACC | GTTATCCGTT | TGCTACTGTG | ATGTATTTTC | 1500 |
| TTGTTGATTT | TGGATATGTG | TTTTCAGGGT | TGAATACCTC | GGATGATGTA | CTAGTTTTTG | 1560 |
| GTATTTTCTA | TGAATAAAGT | GCACGGTAAA | ATTATAAAAA | AAA | | 1603 |

( 2 ) INFORMATION FOR SEQ ID NO:20:

( i ) SEQUENCE CHARACTERISTICS:
        ( A ) LENGTH: 1647 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Gossypium barbadense
        ( B ) STRAIN: Sea Island ( v i i ) IMMEDIATE SOURCE:
        ( A ) LIBRARY: EMBL-SI
        ( B ) CLONE: E62AH3

( x i ) SEQUENCE DESCRIPTION: SEQ ID NO:20:

| ATTTAACAAA | TATATTTTGA | AAAATTGATA | AAAATACTAA | ATGAGGTTTT | GGTTGAATAG | 60 |
| TAAGATATAA | TTATTACAAA | TTATAAATAT | GTAGGTTCAA | AATCTATCAT | GTGTATATTT | 120 |
| GTACTATTAT | TCTATATAAA | TTGATAACCT | TATAAAGTA | TCTAATTTAG | TTTATGGTTG | 180 |
| ATTGATCGAT | AATACCAAAT | TTATTAAAAA | TTAATATTAG | TAAAGATATA | TAGTACAAAA | 240 |
| CTAAACATAA | AATTTTATAT | GTTAAGGAAA | TAGCGGAAAA | AATATCATAT | TTGTAGAACT | 300 |
| GTTAGCAGT | GTGGGAGAAT | GGGATCATTA | CAAGGAAAAA | TGAAATATAT | ATCATTAATA | 360 |
| CCAAACATAA | AAGAAAGCGT | CTTTTGATAA | AGTTGTTATT | GGTGTAATGT | GAAGGGACCA | 420 |
| CAATCATCAC | CATTCACCAC | TTGCTCCTAA | TTGAGTTGAA | ATCTTTTTAC | AACATAGAAA | 480 |
| ACTAGAAGAT | CGCCCTTTCT | TGCTTCATAT | ATATAGATTT | TGTATCATCG | CAATTTCACA | 540 |

```
TCACACACAC  AAGTAAAGCA  TTAGCAACCA  TAGCCATGGC  TTCCTCACCA  AAACTCTTCT   600

CTATGTCTAT  CCTCTTCCTT  TTTGCCCTCT  TCTCCATGCA  AATCCATGCT  AGAGAGTACT   660

TCAGCAAATT  CCCAAGAGTT  AACATCAATG  AGAAAGAGAC  AACAACCAGA  GAGCAAAAGC   720

ACGAGACCTT  CGTTCCCCAG  ACCACCCAAA  AGCCAGAAGA  ACAAGAGCCA  AGGTTCATTC   780

CTGAAACCCA  AAATGGTTAT  GGCCTTTACG  GCCACGAGTC  AGGCTCAGGC  TCAGGCTCAG   840

GCTCAGGCTC  AAGCCGGCCC  AGTTTCACCA  CCAAAGAAAC  CTATGAACCC  TATGTCACCC   900

CTGTTAGATT  CCACCCTGAT  GAGCCCTATA  ACAGCATCCC  CGAATCCTCC  AACAATAAAG   960

ACACTTACTA  CTACAACAAG  AATGCCTACG  AGTCCACTAA  GCAGCAAAAC  TTGGGCGAGG  1020

CCATTTTCAC  CGAGAAAGGA  TGGAGCACCA  AGGAAAACCA  GAACAACAAC  TACTACAACG  1080

GCAACAATGG  TTACAACAAT  GGCGAGAAGC  AAGGCATGAG  CGATACTAGG  TACTTGGAGA  1140

ATGGAAAGTA  CTACTATGAC  GTCAAGAGTG  AGAACAACTA  TTATCCAAAC  CGGTTCGACA  1200

ACTCAAGAGG  AGTTGCTTCG  AGGAACGAGT  TCAATGAGAA  TCGTTACAAC  AACATGGGAA  1260

GGTACCACCA  GAACCAAGAG  GAGTTCGAGG  AAAGCGAGGA  AGAGTTCGAA  CCCTGATCTC  1320

ACCTTCAGAT  GATTTCGCTG  AAGCAGATCC  AAGATGGTTT  GGCATCCTTG  TGTTTACAAG  1380

GAGCAAATCG  AAGATATAGC  TGATTTGGCT  TTCACGTGAT  TACGATGAAG  CAAATCTAAG  1440

ATGATTTGTC  GTCTCTGTAT  CGTTAGAGAA  CGAATCGAAG  TTTGGCATCT  TCACTTTGAT  1500

GGAGAGCAGA  CACATAGCAG  ATCTCACCTT  CAGATGATTT  CGCTGAAGCA  GATCCAAGAT  1560

GGTTTGGCAT  CCTTGTGTTT  ACAAGGAAAA  AATCGAAGAC  ATAGCTGATT  TGGTTCATGT  1620

GATTACGATG  AAGCAAATCT  AAGATGA                                          1647
```

( 2 ) INFORMATION FOR SEQ ID NO:21:

( i ) SEQUENCE CHARACTERISTICS:
        ( A ) LENGTH: 1668 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Gossypium barbadense
        ( B ) STRAIN: Sea Island ( v i i ) IMMEDIATE SOURCE:
        ( A ) LIBRARY: EMBL-SI
        ( B ) CLONE: E6-3B ( x i ) SEQUENCE DESCRIPTION: SEQ ID NO:21:

```
AAATTATAGC  ATACCTCACG  ATGTGGGTGA  AGTAAAATTA  TTTAACAAAT  ATATTTTGAA    60

AAATTGATAA  AAATACTAAA  TGAGGTTTTG  GTTGAATAGT  AAGATATAAT  TATTACAAAT   120

TATAAATATG  TAGGTTCAAA  ATCTATCATG  TGTATATTTG  TACTATTATT  CTATATAAAT   180

TGATAACCTT  ATAAAGTAT   CTAATTTAGT  TTATGGTTGA  TTGATCGATA  ATACCAAATT   240

TATTAAAAAT  TAATATTAGT  AAAGATATAT  AGTACAAAAC  TAAACATAAA  ATTTTATATG   300

TTAAGGAAAT  AGCGGAAAAA  ATATCATATT  TGTAGAACTG  TTTAGCAGTG  TGGGAGAATG   360

GGATCATTAC  AAGGAAAAAT  GAAATATATA  TCATTAATAC  CAAACATAAA  AGAAAGCGTC   420

TTTTGATAAA  GTTGTTATTG  GTGTAATGTG  AAGGGACCAC  AATCATCACC  ATTCACCACT   480

TGCTCCTAAT  TGAGTTGAAA  TCTTTTTACA  ACATAGAAAA  CTAGAAGATC  GCCCTTTCTT   540
```

| | | | | | |
|---|---|---|---|---|---|
| GCTTCATATA | TATAGATTTT | GTATCATCGC | AATTTCACAT | CACACACACA | AGTAAAGCAT | 600 |
| TAGCAACCAT | AGCCATGGCT | TCCTCACCAA | AACTCTTCTC | TATGTCTATC | CTCTTCCTTT | 660 |
| TTGCCCTCTT | CTCCATGCAA | ATCCATGCTA | GAGAGTACTT | CAGCAAATTC | CCAAGAGTTA | 720 |
| ACATCAATGA | GAAAGAGACA | ACAACCAGAG | AGCAAAAGCA | CGAGACCTTC | GTTCCCCAGA | 780 |
| CCACCCAAAA | GCCAGAAGAA | CAAGAGCCAA | GGTTCATTCC | TGAAACCCAA | AATGGTTATG | 840 |
| GCCTTTACGG | CCACGAGTCA | GGCTCAGGCT | CAGGCTCAGG | CTCAGGCTCA | AGCCGGCCCA | 900 |
| GTTTCACCAC | CAAAGAAACC | TATGAACCCT | ATGTCACCCC | TGTTAGATTC | CACCCTGATG | 960 |
| AGCCCTATAA | CAGCATCCCC | GAATCCTCCA | ACAATAAAGA | CACTTACTAC | TACAACAAGA | 1020 |
| ATGCCTACGA | GTCCACTAAG | CAGCAAAACT | TGGGCGAGGC | CATTTCACC | GAGAAAGGAT | 1080 |
| GGAGCACCAA | GGAAAACCAG | AACAACAACT | ACTACAACGG | CAACAATGGT | TACAACAATG | 1140 |
| GCGAGAAGCA | AGGCATGAGC | GATACTAGGT | ACTTGGAGAA | TGGAAAGTAC | TACTATGACG | 1200 |
| TCAAGAGTGA | GAACAACTAT | TATCCAAACC | GGTTCGACAA | CTCAAGAGGA | GTTGCTTCGA | 1260 |
| GGAACGAGTT | CAATGAGAAT | CGTTACAACA | ACATGGGAAG | GTACCACCAG | AACCAAGAGG | 1320 |
| AGTTCGAGGA | AAGCGAGGAA | GAGTTCGAAC | CCTGATCACC | TGTCGTACAG | TATTTCTACA | 1380 |
| TTTGATGTGT | GATTTGTGAA | GAACATCAAA | CAAACAAGC | ACTGGCTTTA | ATATGATGAT | 1440 |
| AAGTATTATG | GTAATTAATT | AATTGGCAAA | AACAACAATG | AAGCTAAAAT | TTTATTTATT | 1500 |
| GAGCCTTGCG | GTTAATTTCT | TGTGATGATC | TTTTTTTTA | TTTTCTAATT | ATATATAGTT | 1560 |
| TCCTTTGCTT | TGAAATGCTA | AAGGTTTGAG | AGAGTTATTG | CTCTTTTTT | CTTCCTCTTT | 1620 |
| CTTTTTTAAC | TTTATCATAC | AAATTTTGAA | TAAAAATGTG | AGTACATT | | 1668 |

( 2 ) INFORMATION FOR SEQ ID NO:22:

( i ) SEQUENCE CHARACTERISTICS:
        ( A ) LENGTH: 1618 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Gossypium hirsutum
        ( B ) STRAIN: Coker 312

( v i i ) IMMEDIATE SOURCE:
        ( A ) LIBRARY: Lambda DASH-CK
        ( B ) CLONE: CKE6-1A ( x i ) SEQUENCE DESCRIPTION: SEQ ID NO:22:

| | | | | | |
|---|---|---|---|---|---|
| CTCACGATGT | GGGTGAAGTA | AAATTATTTA | ACAAATATAT | TTGAAAAAT | TGATAAAAAT | 60 |
| ACTAAATGAG | GTTTTGGTTG | AATAGTAAGA | TATAATTATT | ACAATTATA | AATATGTAGG | 120 |
| TTCAAAATCT | ATCATGTGTA | TATTTGTACT | ATTATTCTAT | ATAAATTGAT | AACCTTATAA | 180 |
| AAGTATCTAA | TTTAGTTTAT | GGTTGATTGA | TCGATAATAC | CAAATTTATT | AAAAATTAAT | 240 |
| ATTAGTAAAG | ATATATAGTA | CAAAACTAAA | CATAAAATTT | TATATGTTAA | GGAAATAGCG | 300 |
| GAAAAATAT | CATATTTGTA | GAACTGTTTA | GCAGTGTGGG | AGAATGGGAT | CATTACAAGG | 360 |
| AAAAATGAAA | TATATATCAT | TAATACCAAA | CATAAAAGAA | AGCGTCTTTT | GATAAAGTTG | 420 |
| TTATTGGTGT | AATGTGAAGG | GACCACAATC | ATCACCATTC | ACCACTTGCT | CCTAATTGAG | 480 |

| | | | | | |
|---|---|---|---|---|---|
| TTGAAATCTT | TTTACAACAT | AGAAAACTAG | AAGATCGCCC | TTTCTTGCTT | CATATATATA | 540 |
| GATTTTGTAT | CATCGCAATT | TCACATCACA | CACACAAGTA | AAGCATTAGC | AACCATAGCC | 600 |
| ATGGCTTCCT | CACCAAAACT | CTTCTCTATG | TCTATCCTCT | TCCTTTTTGC | CCTCTTCTCC | 660 |
| ATGCAAATCC | ATGCTAGAGA | GTACTTCAGC | AAATTCCCAA | GAGTTAACAT | CAATGAGAAA | 720 |
| GAGACAACAA | CCAGAGAGCA | AAAGCACGAG | ACCTTCGTTC | CCCAGACCAC | CCAAAAGCCA | 780 |
| GAAGAACAAG | AGCCAAGGTT | CATTCCTGAA | ACCCAAAATG | GTTATGGCCT | TTACGGCCAC | 840 |
| GAGTCAGGCT | CAAGCCGGCC | CAGTTTCACC | ACCAAAGAAA | CCTATGAACC | CTATGTCACC | 900 |
| CCTGTTAGAT | TCCACCCTGA | TGAGCCCTAT | AACAGCATCC | CCGAATCCTC | CAACAATAAA | 960 |
| GACACTTACT | ACTACAACAA | GAATGCCTAC | GAGTCCACTA | AGCAGCAAAA | CTTGGGCGAG | 1020 |
| GCCATTTTCA | CCGAGAAAGG | ATGGAGCACC | AAGGAAAACC | AGAACAACAA | CTACTACAAC | 1080 |
| GGCAACAATG | GTTACAACAA | TGGCGAGAAG | CAAGGCATGA | GCGATACTAG | GTACTTGGAG | 1140 |
| AATGGAAAGT | ACTACTATGA | CGTCAAGAGT | GAGAACAACT | ATTATCCAAA | CCGGTTCGAC | 1200 |
| AACTCAAGAG | GAGTTGCTTC | GAGGAACGAG | TTCAATGAGA | ATCGTTACAA | CAACATGGGA | 1260 |
| AGGTACCACC | AGAACCAAGA | GGAGTTCGAG | GAAAGCGAGG | AAGAGTTCGA | ACCCTGATCA | 1320 |
| CCTGTCGTAC | AGTATTTCTA | CATTTGATGT | GTGATTTGTG | AAGAACATCA | AACAAACAA | 1380 |
| GCACTGGCTT | TAATATGATG | ATAAGTATTA | TGGTAATTAA | TTAATTGGCA | AAAACAACAA | 1440 |
| TGAAGCTAAA | ATTTTATTTA | TTGAGCCTTG | CGGTTAATTT | CTTGTGATGA | TCCGAATTCT | 1500 |
| CGCCCTATAG | TGAGTCGTAT | TAGTCGACGG | TATCGATAAG | CTTGATATCG | AATTCCTGCA | 1560 |
| GCCGGGGAT | CCACTAGTTC | TAGAGCGGCC | GCCACCGCGG | TGGAGCTCCA | GCTTTTGT | 1618 |

( 2 ) INFORMATION FOR SEQ ID NO:23:

( i ) SEQUENCE CHARACTERISTICS:
        ( A ) LENGTH: 1578 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Gossypium hirsutum
        ( B ) STRAIN: Coker 312

( v i i ) IMMEDIATE SOURCE:
        ( A ) LIBRARY: Lambda DASH-CK
        ( B ) CLONE: CKE6-4A ( x i ) SEQUENCE DESCRIPTION: SEQ ID NO:23:

| | | | | | |
|---|---|---|---|---|---|
| ATTTATATTA | AATTAATATA | GCATACTGGG | TGAGAAGTAA | AACTATTTAA | CAAATATATT | 60 |
| CTTAAAAATA | CTAAGGAGG | TTTTGGTTGA | ATAGCAAAAT | ATAAATATTA | CAAATTATAA | 120 |
| AAATGTAGGT | TCCAATATTT | TTACTATTTT | TCTATATAAA | ATGATAACCT | TAAAAAGTAG | 180 |
| TTTGTGGTTG | ATGGACTAAT | TTTTAAAAA | GAATTAATAT | TAGTAAAGAT | ATATATGGTA | 240 |
| CTAAACATAA | GGAAATAGGG | AAAACGTATC | ATATTTGTAG | TGGGAGAATG | GGATCATTAC | 300 |
| AAGGAAAAAT | GAAATACATA | TCCTTAACAA | CAAACATAAA | AGAAAGCGTC | TTTTGATAAA | 360 |
| GTTGTTATTG | GTGTAATGTG | AAGGGACCAC | AATCATCACC | ATTCACCACT | TGCTCCTAAT | 420 |
| TGAGTTGAAA | TCTTTTTACA | ACATAGAAAA | CTAGAACATC | TCCCTTTCTT | GCTTCCTATA | 480 |
| TATAGATTTT | GTATCATCGC | AATTCCACAT | CACACACGCA | AGCAAAGCAA | AGCATTAGCA | 540 |

| | | | | | |
|---|---|---|---|---|---|
| ACCATAGCCA | TGGCTTCCTC | ACCAAAACTC | TTCTCTATGT | CTATCCTCTT | CCTTTTTGCC | 600
| CTCTTCTCCA | TGCAAATCCA | TGCTAGAGAG | TACTTCAGCA | AATTCCCAAG | AGTTAACACC | 660
| AATGAGAAAG | AGACAACAAC | CAGAGAGCAA | GAGCACGAGA | CCTTCGTTCC | CCAGACCACC | 720
| CAAAAGCCAG | AAGAGCAAGA | GCCAAGGTTC | ATCCCTGAAA | CCCAAAATGG | TTATGGCCTT | 780
| TACGGCCACG | AGTCAGGCTC | AGGCTCAGGC | TCAGGCTCAA | GCCGGCCCAG | TTTCACCACC | 840
| AAAGAAACCT | ATGAACCCTA | TGTCACCCCT | GTTAGATTCC | ACCCTGATGA | ACCCTATAAC | 900
| AGCATCCCCG | AATCCTCCAA | CAATAAAGAC | ACTTACTACT | ACAACAAGAA | TGCCTACAAG | 960
| TCCACTAAGC | AGCAAAACTT | GGGCGAGGCC | ATTTTCACCG | AGAAAGGATG | GAGCACCAAG | 1020
| GAAAACCAGA | ACAACAACTA | CTACAACGGC | AACATTAATG | GCGAGAAGCA | AGGCATGAGC | 1080
| GATACTAGGT | ACTTGGAGAA | TGGAAAGTAC | TACTATGACG | TCAAGAGTGA | GAACAGCTAT | 1140
| TATCCAAACC | AGCTCGACAA | CTCAAGAGGA | GTTGCTTCCA | GGAACGAGTT | CGATGAGAAT | 1200
| CGTTACAACA | ACATGGGAAG | GTACCACCAG | AACCAAGAGG | AGTTCGAGGA | AAGCGAGGAA | 1260
| GAGTTCGAAC | CCTGATCACC | TGTCGTACAG | TATTTCTACA | TTTGATGTGT | GATTTGTGAA | 1320
| GAACATCAAA | CAAAACAAGC | ACTGGCTTTA | ATATGATGAT | AAGTATTATG | GTAATTAATT | 1380
| AATTGGCAAA | AACAACAATG | AAGCTAAAAT | TTTATTTATT | GAGCCTTGCG | GTTACTTTCT | 1440
| TGTGATGATC | TTTTTTATTT | TCTAATTATA | TATAGTTTCC | TTCGCTTTGA | AATGCTAAAG | 1500
| GTTTGAGAGA | GTTATGTTCT | TTTTCTCTTC | CTCTTTCTTT | TTTAACTTTA | TCAAACAATT | 1560
| TTTGAATAAA | AATGTGAG | | | | | 1578

( 2 ) INFORMATION FOR SEQ ID NO:24:

( i ) SEQUENCE CHARACTERISTICS:
        ( A ) LENGTH: 1618 base pairs
        ( B ) TYPE: nucleic acid
        ( C ) STRANDEDNESS: double
        ( D ) TOPOLOGY: linear ( i i ) MOLECULE TYPE: Genomic DNA ( i i i ) HYPOTHETICAL: NO ( i v ) ANTI-SENSE: NO ( v i ) ORIGINAL SOURCE:
        ( A ) ORGANISM: Ceiba pentandra ( v i i ) IMMEDIATE SOURCE:
        ( A ) LIBRARY: EMBL CP
        ( B ) CLONE: E6 R5

( x i ) SEQUENCE DESCRIPTION: SEQ ID NO:24:

| | | | | |
|---|---|---|---|---|
| TGGTATTTAG | TATATTTAAA | TTTTAAATAT | TAATATATGT | AAAATTAAAA | 50
| AAAAAAATTA | GATTAGGATT | TATTTTATAA | AAAAAATGGA | AATGAGATCA | 100
| TAAAAGAGC | ACCAAATAAT | AATAATAAAA | GAAGAAATCA | AAGTCAATCA | 150
| TTAACAACAA | ACACAAAGTG | AAGAGGCCAC | TTTTGATAAA | GTCTTATGTC | 200
| TCGTGCAAGG | GACCACACAC | ACAATCATCA | GTTTTCACAG | TCTCCCCCCC | 250
| GTCCCGTTTG | CAACTAATTG | AGTAGAAAAT | TTTACAAATT | GAGGGGAAAC | 300
| GAAAAAATTT | GCCTTTCTAT | ATAAACATTT | CCTATCATCA | CAATTTCTCA | 350
| TTAGTGTGCA | CTCTCCCACG | CAAAAAAAAA | AAAAAAAAGA | AAGAAAGCAT | 400
| TAGCTAGCCT | TCCCCTTGCC | CATGGCTTCC | TCACCGAAAC | TCGTTGCTAT | 450
| CTTCTTCCTC | TTTGCCCTCT | GCTCCATGCA | GATTGATGCT | AGAGAATTCT | 500

```
TCAGCAAAGT  CCCAAGTGTC  AACACCAATG  AGAAGGAGTC  AACAACCATT   550
CCTGAGACCT  TCATTCCCGT  GACGACCACC  CAAAGACTT   TGCTTCCCAA   600
CAAAGAAGAG  CAGAGCACTT  TCGGGAAGAA  CGAGCAAGAG  CCAAGGTTTA   650
TCCCTGAGAC  TCAAAACGGA  TATGGCCTTT  ATGGTCACGA  GTCAGGCCAG   700
CTCCCTCCCA  GCACCACCAC  CAATACCAAA  GAAACCTATG  AACCCTATGT   750
TACCCCTGTT  AGATTCCACC  CTGATGAACC  TTACAACAGC  ATTCCTGCAT   800
CCAAAACTAA  CAACAAAAAT  ACTTACTATT  ACAACAAGAA  CCGCTATGAG   850
AATACCGAGA  AACAAATCT   GGCTGAAGCC  AGCTTCACAG  AGAAAGGATG   900
GAGCACCAAG  GAAAACCAGA  ACAACAACAA  CTACTACAAC  GGCAACAATG   950
GGTACAACAA  GAATGCCTAT  GGGATACCG   AGCAGCAAAA  TTTGGGTGAG  1000
ACCATTTTCA  CAGAAAAGG   ATGGAGCACC  AAGGAAAACC  AGAACAACAA  1050
CTACTATAAT  GGCAACAATG  GATACAACAA  TGGTGAGAAG  CAAGGCATGA  1100
GCGACACTAG  ATTCTTGGAG  AATGGAAAGT  ACTACTATGA  TCTTAAGAAT  1150
GAGAACAACT  ACTATCCAAA  CCAGTTTGAG  AACTCCAGGG  GAGTTGCTTC  1200
AAGGAACGAG  TTCAATGAGA  ATCGTTACAG  CAACGTGGGA  AGGTACAACC  1250
AGAACCAAGA  GGAGTTCGAA  GAGAACGAGG  AAGAGTTCGA  GCCATGAGCT  1300
AGCTGTCTTG  TACTCTCTAC  AATGGAGTGA  AAAACATCAA  GCAAACAAG   1350
AAGTGGTTTT  AATTAGACGA  TAAGTATGCT  ATAATTAATT  AGCAAAAACA  1400
GTAAAGAGAA  AGATTTTATT  TATTGGGTCT  TGCGTTTAGT  TTGTGATCTT  1450
TTCATTTTCT  GGTTGCATA   GTATCCTTTG  CTTTGCAATG  CTCAAGATAT  1500
GAGAGTCATG  CTTTTATTT   CTTTTCTACT  TTATCAAACA  ATTTATTGAA  1550
TAACAATGTA  AGTATCTCCT  AATAATCAGT  CTTCAGTTTT  CATATTCGCC  1600
TCTCTAGCAA  ATGCACCA                                        1618
```

(2) INFORMATION FOR SEQ ID NO:25:

( i ) SEQUENCE CHARACTERISTICS:
        ( A ) LENGTH: 1984 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Gossypium barbadense
        ( B ) STRAIN: Sea Island ( v i i ) IMMEDIATE SOURCE:
        ( A ) LIBRARY: EMBL SI
        ( B ) CLONE: SIH6

( x i ) SEQUENCE DESCRIPTION: SEQ ID NO:25:

```
GTCGACCTGC  AGGTCAACGG  ATCTTTTTA   GCTGTGTTTA  TTAAAAAAA     50
TAAAAAAATA  TAAAGTAGT   TTTTTAGAG   TAAATGTAAA  ACTTTAAAAT   100
AATTGTAATA  TGTAAAATTA  AAAATATTAA  ACTATTTACA  ACCGTCGGAT   150
TAAAAATGAT  ATATTTTGA   ATGATGATGA  AGATCGATTC  CTGATGTATA   200
```

-continued

| | | | | | |
|---|---|---|---|---|---|
| TAAATACTGC | CTTCTATTCC | CTTCAGTCTT | CGCTTCACCC | ACTTTCTCAT | 250 |
| TTCACACGGG | TTGTGGCGTA | GTTTAAGCAG | AGAGGGTGCG | CAGGATAAAG | 300 |
| CTATTCACCA | TTGTTTCAAC | ATGAAGGTTT | GTAATAAAAA | TTTGTTTCTA | 350 |
| TCAGCATTGC | TTTGCATTGC | TGTTGCAGGA | GTTTTGGGTC | AAGCTCCTAG | 400 |
| TAATCCTCCT | ACGTCTACGC | CGGCGCCACC | CACACCACCG | GCTTCTACTC | 450 |
| CTCCTCCGAC | GACTCAAGCA | CCGCCTACAC | CAACCGCCAC | TCCGCCACCG | 500 |
| GTTTCTACTC | CTCCTCCCAC | TTCATCACCG | CCCCCAGTGA | CAGCTTCTCC | 550 |
| ACCCCCAGTT | TCAACTCCTC | CACCCAGTTC | TCCTCCTCCT | GCAACTCCAC | 600 |
| CACCTGCTTC | TCCTCCTCCT | GCAACTCCAC | CTCCAGCTTC | TCCACCTCCT | 650 |
| GCCACTCCTC | CACCAGCTTC | TCCACCTCCC | GCCACTCCAC | CACCTGCAAC | 700 |
| CCCACCGCCA | GCAACTCCTC | CTCCTGCTAC | CCCACCACCA | GCTCCATTGG | 750 |
| CTTCTCCTCC | AGCCACAGTC | CCAGCTATCT | CTCCAGTACA | AACACCATTG | 800 |
| ACATCGCCAC | CAGCTCCGCC | GACCGAGGCC | CCAGCACCTA | CCCTCGGGGC | 850 |
| TGCTACGCCA | GGTCCAGCTG | GAACTGACAC | GGTACATTTT | CTCTTATTCC | 900 |
| ACCATTTTAT | ATCCTTCTTC | TCCACCTACG | ATCAAGCTTT | ATTATCGGTT | 950 |
| GAAATTTAAG | CCTTTACAGC | AAGACTTAAA | ATATAATTTT | ATTAATGGTT | 1000 |
| TTATAATATT | AAATTATAAT | TTATCATTC | TTACACATTA | ATATATAATG | 1050 |
| TGATAAAATT | TTTTACTTTG | GGTACCGTGC | CAACTTCCTA | ACGTCGCCCT | 1100 |
| TAATCTTACA | TAAACAACGA | TCTGAGCTTG | TCTCGATATT | AGCTAACCCT | 1150 |
| TAAGCCATTA | GAGATGGCTA | TTGGTTCCGT | CTCGACATAC | CTTCAACATA | 1200 |
| ATCTGATTTA | AAATTAAATA | CTTATATCTA | TTTTTTAACA | CAATATTTAA | 1250 |
| AATTATCTAT | AATTTCTTCT | CAACTTATAA | TTAAAATAAC | AATACTTCAG | 1300 |
| CGTATTCAAA | TTTACGTACC | TATGTTAATC | TAATTTGACA | ATAATATTTA | 1350 |
| TGTTAATTGA | ATTAAAGCTT | GAGATATTAA | ATTTAATTAA | GACTCAACAT | 1400 |
| TGACGACAGT | ACGATTCAAC | GTATTAGATT | TAATTAATGT | TGATTTTGAA | 1450 |
| CCTATTATTG | CAGAGTGGAG | CAAATCAAAT | GTGGACCGTA | CAAAAGATGA | 1500 |
| TGGGAAGCTT | AGCCATGGGA | TGGGCTCTGC | TCAATCTGAT | GGTTTAAAAC | 1550 |
| AAAAGAGTGC | CTCACATTTG | ATGCAATAGC | TCTGTAATGT | TTCATTCATT | 1600 |
| TGCTTATTTC | GGCCTTGTTT | TTCTCGTATT | CTATGGGCTG | ATGTCTCATA | 1650 |
| TGGGACTTTT | CTACTAGAGA | GCCTACGTTA | CTTTACCATT | ATATTGTATT | 1700 |
| CTTTGAGACA | TTATTATTAT | TTTTTTACCT | TTTGAGGACA | CTCTTTTTTT | 1750 |
| GTATTTGAAG | GAATTATTG | TTTATTTGT | TTGGAATATG | TTTGGTTGGA | 1800 |
| TTTATTCGAT | TCATATATAT | TATATAAAAG | TAATTATGTT | ATTAAGAAAC | 1850 |
| GTAGTAAGAA | CTTACAAATA | TAAGGATCGA | ATCCCGAACT | TCATGCAAAT | 1900 |
| CAATTTACAA | CCCACACAAG | TTTAACATTA | AATTAACGTG | ATTGGTTAGT | 1950 |
| AAATTCATGT | TTCTCTGTTT | AATTTGTTGA | ATTC | | 1984 |

( 2 ) INFORMATION FOR SEQ ID NO:26:

( i ) SEQUENCE CHARACTERISTICS:
        ( A ) LENGTH: 2415 base pairs
        ( B ) TYPE: nucleic acid
        ( C ) STRANDEDNESS: double
        ( D ) TOPOLOGY: linear (i i) MOLECULE TYPE: DNA (genomic)

(i i i) HYPOTHETICAL: NO (i v) ANTI-SENSE: NO (v i) ORIGINAL SOURCE:
   (A) ORGANISM: Gossypium barbadense
   (B) STRAIN: Sea Island (v i i) IMMEDIATE SOURCE:
   (A) LIBRARY: EMBL SI
   (B) CLONE: SIB12

(x i) SEQUENCE DESCRIPTION: SEQ ID NO:26:

| | | | | | |
|---|---|---|---|---|---|
| CTGGCCTTTT | GCTGGCCTTT | TGCTCACATG | TTCTTTCCTG | CGTTATCCCC | 50 |
| TGATTCTGTG | GATAACCGTA | TTACCGCCTT | TGAGTGAGCT | GATACCGCTC | 100 |
| GCCGCAGCCG | AACGACCGAG | CGCACGGGNT | CAGTGAGCGA | GGAAGCGGAA | 150 |
| GAGCGAAAAA | TACGCAAACC | GCCTCTCCCC | GCGCGTTGGC | CGATTCATTA | 200 |
| ATGCAGCTGG | CACGACAGGT | TTCCCGACTG | GAAAGCGGGC | AGTGAGCGCA | 250 |
| ACGCAATTAA | TGTGAGTTAG | CTCACTCATT | AGGCACCCCA | GGCTTTACAC | 300 |
| TTTATGCTTC | CGGCTCGTAT | GTTGTGTGGA | ATTGTGAGCG | ATAACAATT | 350 |
| TCACACAGGA | AACAGCTATG | ACCATGATTA | CGCCAAGCTC | GAAATTAACC | 400 |
| CTCACTAAAG | GGAACAAAAG | CTGGAGCTCC | ACATGGTTTA | ATTAAACATT | 450 |
| ATGTTCCATC | CATCTATATT | TATATCCATT | AAAACAAGTC | GTTGAGCAAA | 500 |
| TAATGGATAC | TGGATACCAT | CATATCTATG | ATTAAAATTT | TGCATGTGCC | 550 |
| CTTTTAATGT | ATAGCTTAAT | TATCCTCCAA | ATTTGTACTC | TTTCACCACT | 600 |
| AATTAGCTAC | GTACGTTACT | TAGCTTTGCT | TGTCGTCATC | TTCTGTACTA | 650 |
| CAAACTCTTT | CTCTTTTGT | ATAAATAGCT | ATACACTTTT | TCTCTCCTCA | 700 |
| AATCAATAAG | GTTAGGTCAA | CCAATTGTTT | GAGCTAGCTA | GCTCTTACTC | 750 |
| AAATGGCAAC | CAAAACGATG | ATGTTGCAAA | TATTTTCACT | TTTCTTCTTT | 800 |
| TTGTTCAGTG | TATGCAACTC | CATTTTCCTT | GGTGCTAATG | GAGATGACAA | 850 |
| TGGTGGTTGC | AAACTGCCCA | TGCACCTTCT | ACGGTGGTGC | TGATGCTACC | 900 |
| GGCACAATGG | GTGAGTTTCA | AACTTTCAAA | CCATTACCTA | CATAAAAATC | 950 |
| TCTAGGCTAT | GTTCTTAATT | TGTGATGTTT | CTATAGGGGG | AGCTTGTGGT | 1000 |
| TATGGAAACC | TGTACAGTCA | AGGGTATGGA | ACGAGCACAG | CAGCTTTGAG | 1050 |
| CACTGCACTT | TTCAACAATG | GCTTGAGCTG | CGGTGCACTG | CTACGAGCTC | 1100 |
| CGGTGCAACA | ATGATCCTCA | ATGGTGCATT | AGTCGAACCA | TAACCGTGAC | 1150 |
| AGCCACCAAC | TTTTGTCCCC | CTAACTATGC | TTTATCTAGT | GACAATGGCG | 1200 |
| GGTGGTGCAA | TCCCCCACGA | GAACACTTTG | ATTTGGCCGA | ACCGGCATTC | 1250 |
| TTGCAGATCG | CGGAATATCG | AGCTGGAATC | GTCCCTGTTA | TGTTCAGAAG | 1300 |
| GTGGTGAATA | AAACTCAATT | CAAATCATCA | CACTCTTTAA | GGTATGTTAA | 1350 |
| ACTGTTGGGT | GTTTAACCTT | TTGCAGGGTG | TCATGTGTGA | AGAAGGAGG | 1400 |
| CATCAGGTAC | ACCATGAATG | GACATTCGTA | CTTCAACATG | GTGTTGATAA | 1450 |
| CCAACGTGGG | AGGGGCAGGG | GATATAACGT | CAGTGTCCAT | CAAGTGTTCC | 1500 |
| AAAACAGGAT | GGCTACCTAT | GTCCAGAAAT | TGGGGCCAAA | ACTGGCAGAG | 1550 |
| CAATGCTTAC | CTTAACGGCC | AAAGCCTCTC | TTTCAAAGTG | ACTGCCAGCG | 1600 |

| | | | | | |
|---|---|---|---|---|---|
| ATGGCAGGAC | TATCACAAAC | TACAATGTAG | TGCCTGCTGG | TTGGCAATTC | 1650 |
| GGACAAACTT | TTGAAGGAGG | CCAGTTTTAA | GACAATATTA | TAGTGTCTGT | 1700 |
| CTAATATTAA | AACTGGAATT | GACATATTAC | TTATATAAGG | CACATGAGCG | 1750 |
| TTTTATGCCG | AGGTAGTAAA | GTGGCGCCCG | CTGCGTTTAT | GTGTGAAATA | 1800 |
| GGCGAGCAAG | TGCCATTAGC | CTATAATATA | TACATTTCTT | ATAGTGAACC | 1850 |
| AAACTATTAA | GTTTGAACTC | TAGAGGTGAT | ATCCATAATG | TCTGAAATTT | 1900 |
| GATTGTTGAT | GATTGACCAT | GATATTTATG | GTTTTCATTA | TTGAAATACT | 1950 |
| TTTTTTTTAT | AATTTATAAA | TAATGGGTCA | TTTCTTTTTA | CAAATATTTT | 2000 |
| CGACATATTT | TATGATTTGT | CAGCTAAATA | TTATTAATCA | AAATTAGGAT | 2050 |
| GCAATATTGA | ATCAAGAATG | TATAAATGAA | TTATTGAGAC | ATCATATAAG | 2100 |
| ATATAAAGA | TGTATCATAT | TTTTTACGTT | GAGCAGTCAT | ACAATAAAAT | 2150 |
| TAATCTCCTA | ATATAAGATA | GTATTTCAGT | AGTGCATATG | TTGAATGGTA | 2200 |
| ACTTTGTTGT | GAGGCAAATA | ATTTTGCCCA | AGGTGCTATG | TAGCAGAGAG | 2250 |
| CGGGAGTTGC | ACATTTGTCA | TAATTTAGGG | AGCCAAACCA | TGCAACGGAT | 2300 |
| TTCATGGCCA | AGATAGTCAT | TGGGGTCGGG | ACTCCCAAAA | TTTTAATTAG | 2350 |
| TCCCTCCTTC | AAGTTTTTCT | AAATTTTCAA | ATATTTTAAT | TGGACTCCTC | 2400 |
| TAACTTTTCT | TTTTT | | | | 2415 |

( 2 ) INFORMATION FOR SEQ ID NO:27:

( i ) SEQUENCE CHARACTERISTICS:
        ( A ) LENGTH: 279 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Gossypium barbadense
        ( B ) STRAIN: Sea Island ( v i i ) IMMEDIATE SOURCE:
        ( A ) LIBRARY: EMBL SI
        ( B ) CLONE: SIA 11 B ( x i ) SEQUENCE DESCRIPTION: SEQ ID NO:27:

| | | | | | |
|---|---|---|---|---|---|
| CCCTTTTCCC | AACCCTTTTC | TCCTGTATCA | AAGACTTGGT | GGTGCAACAA | GCCTTGTTCT | 60 |
| CAACCTTGGA | GGATTGGCTA | GTGAAGCATC | CCAAAATCCT | CCAGTTTTCA | TGGGAAAATG | 120 |
| GCCAAACACC | AGCCTCCTCT | CACCGCTTCC | TCACCCTCAC | TGTCTTGTCT | TACATCTCTT | 180 |
| TCACATTCGT | TCTCTCCCAA | CTATCTCGCC | CTTCACTTTC | ACGTCCACTC | CTCAAATCAA | 240 |
| TCGCAGCTGT | CCACAACATC | TTCCTCCTTA | CCCTTTCTT | | | 279 |

( 2 ) INFORMATION FOR SEQ ID NO:28:

( i ) SEQUENCE CHARACTERISTICS:
        ( A ) LENGTH: 2539 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Gossypium barbadense
    ( B ) STRAIN: Sea Island ( v i i ) IMMEDIATE SOURCE:
    ( A ) LIBRARY: EMBL-SI
    ( B ) CLONE: SIB8

( x i ) SEQUENCE DESCRIPTION: SEQ ID NO:28:

```
TTTTTAATGG TGTTGGATGG TTATATTATA TCTCGATTAT ATATATTTTT TTTAAAAACC    60
GAAGTTGAAT GTCTAAATAG GAAGTAATTT TTTAATATT ATTTTTTAT AATATTTGAA   120
TCCGATATCT TATTTAAAAA CCATCGAAAT TTTTATTACT CAATCATTAC CGAAATAGAA   180
TCGGGCTAAA ATATTTCGAA AACTAAAAGT TTCACTTTTT ATATTGAAAA ACGAGGCTTT   240
GTGATTCTTA TAAATTTAAT TCATTGAAAT TTCATCAAGT AAAACAGAAG AATTATAAAT   300
CTCTAAAATG ATAGATAAAA ATGTCGCAAA TAAAGCCATT GTGACACCCA TTAAAGGAGT   360
CTTTTCCCAT CCAGGGGCTA CCTTACCATA TTCCGAATTC AATGGTTTCA AAAAATCTCC   420
TACAACAATT CGTCTTGGAC TAGATCTAGA ACTACTGTTA ACGTTTTGTG TAGCCATAAA   480
TCTTATTTTG TATTCATTGA GATTTGTTAA CTTTGTATAT CATTTCACTA TAAATAAACA   540
ATCTTATCAT AGACCCATTG TGATCATGAA ATTATATAAT AATGGAAACA AAACCTTAG   600
TTGCAATCTC TATATCTGAT TTACTTGTAA GTTTTACTAG GTACGCCTTA TATACTGCTT   660
TTGGGTAACT CTCTCAACAA TTAAGAGATC CATTCGAGGA ATACGGGAAA TAATTGAAGA   720
AACGAGCCTC CCCATATGTA TGTCTATTTG GTCACATATC CACTCCAAAA TCTACTCTGT   780
TTTCCCTGCT TTTCCAAGCA ATGTAGTTGC TCATCAATTT CTTTCCTTTC AAATAAACAT   840
CCCAACAGAG TTTGCTAAAG TTGATAAGTA TGTCTTCTAG TTAACTAAAG TAGCATATTT   900
TACCTAACTT CACCCTCCAA TATCCTAAAT AAAAAGCTCC CATTTCTTAT CCAATCAAAA   960
CATCCATAAC ATTTTTGTTC AAGGACCACT TCTTCCCTTC CATTTTACTT TGTTTTAGTT  1020
GCCATAACGT CACCTTCCAA TACAACCCAC AATGAGGCAA CAATATGTCT TCACTACTCT  1080
CACGTTGCTC ATCCTGTTTT CCCTCAGTTG TTCAACAACA TTAGCCCAAT CTCCGGCACT  1140
GGCCCCGGCA CCTTCTGGTC CGACAAACGT CACCAAGATC CTCGAAAAAG CTGGTCAATT  1200
CACCCTCTTC ATTCGTCTTC TAAAGTCCAC TCAAGTGGCC AACCAGCTGC TCGGTCAGCT  1260
CAACAATTCC AACAATGGTA TGACCGTTTT TGCACCAACG GACAATGCTT TCTCCAGCCT  1320
TAAATCGGGC ACATTGAATT CACTCACCGA TGAACAAAAA GTGCAGCTGG TGCAATTCCA  1380
CATCGTCCCA ACATACCTCA CCTCGTCTCA GTTCCAAACC ATTAGCAACC CTTTGAGAAC  1440
CCAAGCTGGT GATAGTGGCG ATGGCAAGTT CCCTCTCAAT GTCACCACTT CGGGGAACTC  1500
TGTGAATATA ACAACAGGGT TGACAAACAC CAGTGTTTCC GGCACTATTT ACACTGATGG  1560
TCAGCTTGCT GTTTATCAAA TCGATCAAGT TCTTCAACCA TTGCAAATAT TTGCACCTAG  1620
GCCTCCAGCT CCCGCACCGG CACCGGCAAA GTCGAAGAAT AAGAAGGCTA CCACTGTTGC  1680
TGATAGCCCC GATGTTACCC CAGCTGATAA CTCCAAAGCG GCCACCTTGC AAAATGCTGG  1740
TTTGTTTGGA GTTGCTGCTC TAGTTATTGC ACTTTCTTTG TGACCATGAA AATGGAGAAA  1800
AGAAGAAGAC AGTGATTTTG ATGGTGGTGA TCAAATTGGA GTAAATAGTG AAATTAAAAA  1860
TAGATATAAT TGAGTTATTT TGTAAACATA TTAAATTCCT TATTTATTAT TTATATACTT  1920
ACTTACTAAG CTATAAGCTT ACTTCTTTT CTCTCTTTTG TTTTATAGTG GCATCCAGCT  1980
```

| AGCACAGGAG | TTAGAGATCG | TTGAAGATCT | GCTCGCACTA | TCAATACTTT | TGGTATTTGA | 2040 |
| ACTCAACATT | TTGAATTATG | GCATGTATAG | TAGGCTTAGT | TATTTTGTTA | CGTGTCATAA | 2100 |
| GTGCCTAGGT | TTAAAATATC | GGTTATAGTA | TTTGACCGAT | TATTTTGTAC | AAAGCCATTG | 2160 |
| AAGTTGGCTA | ATATTGTTAA | AGGCATATGT | TATAACGATT | CATGATCTAA | TTGAATGTCT | 2220 |
| CGGTTTTATT | TAATGGTATG | TGTTATATTC | TGGTAATACC | TCGTACCCTG | TTTCAGTGTT | 2280 |
| GAATGCGAGT | AAGGGGCGTT | ACAATAGCCT | TCATAAACAA | GTTCACCAAC | GGCTTGAAAT | 2340 |
| ACTCTAAAAG | GTAAGGATAA | GAACAAGAAC | TCAATCTTTA | TTCAATACAC | TCATGGTTTT | 2400 |
| ATCAAGAAGA | TCGGTTGAAG | AGTTAGAAAG | TCCTAGTTGC | ACATCACATG | TTATTTTGTC | 2460 |
| AAACATGTTA | CTACTTTAAA | AGCCGAAAAC | ATTGACTGTC | CATGAGGTCG | AAACCTTCCA | 2520 |
| CACAGTTGAA | ACAAAAAA | | | | | 2539 |

( 2 ) INFORMATION FOR SEQ ID NO:29:

( i ) SEQUENCE CHARACTERISTICS:
        ( A ) LENGTH: 562 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Gossypium barbadense
        ( B ) STRAIN: Sea Island ( v i i ) IMMEDIATE SOURCE:
        ( A ) LIBRARY: EMBL SI
        ( B ) CLONE: SIB6

( x i ) SEQUENCE DESCRIPTION: SEQ ID NO:29:

| TTTTTCAAAT | CGAATCGAGT | TTTGCTCACC | CTAAGACAAC | CATATCTAAT | CCAATATCTG | 60 |
| GTTTTCAAAT | ATTTCTTTT | AATCATGGTT | AGTTTTTTG | TTAATTTTCT | ATACCTACTT | 120 |
| TTACCTTAA | ACTTCACATC | CATTTTGATC | ACCAACAACT | GGTACAACCC | CACACGTTGT | 180 |
| TTTTTTTCTG | TTTATATCTT | ACAACTTACA | ACCGAAACAT | CCACAGTACA | CACACATATA | 240 |
| TATATTCATC | CAATCTGCTA | AATTGGTATC | CAAAACTATT | CAACTTTCTC | TCTGAACTCC | 300 |
| TCCAAGTTAG | GTTAGTGTTT | TCCATAATTT | GCATTGTGT | TAAAAGTTGC | TTCTCTTGAG | 360 |
| AGTTCAAAGG | ATTCATTTTT | CTTTCAAGTT | ACATGCATGT | CTATGTTTTG | AAATGGGGTT | 420 |
| TACTTTTTTC | TTTTGTTCAT | AATGTAAATT | TATTGGATAT | TTTGCTGTTT | ATCTGCAAGT | 480 |
| AATTGCCAAT | GATTTGATTC | TTGTAGGAGT | TTGGAGAGTG | GTCACCGCTG | AAGCAAAGCC | 540 |
| AAATTTCTTG | GGGGAAAAGA | AA | | | | 562 |

( 2 ) INFORMATION FOR SEQ ID NO:30:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: YES ( x i ) SEQUENCE DESCRIPTION: SEQ ID NO:30:

ACCGAAATAG AATCGGGC                                                                        18

(2) INFORMATION FOR SEQ ID NO:31:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: YES (xi) SEQUENCE DESCRIPTION: SEQ ID NO:31:

CGCGGTTCGA ACCATGGTTT AGAGATTTAT AATTC                                                     35

(2) INFORMATION FOR SEQ ID NO:32:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: YES (xi) SEQUENCE DESCRIPTION: SEQ ID NO:32:

GGAGAATGCT CGGGAGGTGG T                                                                    21

(2) INFORMATION FOR SEQ ID NO:33:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: YES (xi) SEQUENCE DESCRIPTION: SEQ ID NO:33:

TAGATCTCGA GCCATGGTAA CACAACAAGC CTTTT                                                     35

GENETICALLY ENGINEERING COTTON PLANTS FOR ALTERED FIBER

CROSS REFERENCE TO RELATED APPLICATIONS

This application is a continuation-in-part of Ser. No. 07/617,239, filed Nov. 21, 1990, now abandoned which is a continuation-in-part of Ser. No. 07/253,243 filed Oct. 4, 1988, now abandoned. Both of these applications are hereby incorporated by reference.

FIELD OF THE INVENTION

The present invention relates to the general technology of plant genetic engineering and, in particular, to the identification of fiber-specific promoters and the use of these promoters to create novel genetically transformed cotton (Gossypium) plants and lines with varied cotton fiber characteristics and quality.

BACKGROUND OF THE INVENTION

Genetic Engineering of Plants

The hurdle of creating successful genetically engineered plants in major crop varieties is now being overcome sequentially on a plant-by-plant basis. While plant genetic engineering has been successfully demonstrated in several model plant species, most notably tobacco, carrot and petunia, these species are not considered agriculturally important. Therefore, researchers have now directed their efforts toward improving commercially important crop plants through the use of genetic engineering (Potrykus, I., *Annu. Rev. Plant. Physiol. Mol. Biol.* 42: 205–225, 1991).

The term "genetic engineering," as used herein, is meant to describe the manipulation of the genome of a plant, typically by the introduction of a foreign gene into the plant, or the modification of the genes of the plant, to increase or decrease the synthesis of gene products in the plant. Typically, genes are introduced into one or more plant cells which can be cultured into whole, sexually competent, viable plants which may be totally transformed or which may be chimeric, having some tissues transformed and some not. These plants can be self-pollinated or cross-pollinated with other plants of the same or compatible species so that the foreign gene or genes carried in the germ line can be bred into agriculturally useful plant varieties.

Current strategies directed toward the genetic engineering of plant lines typically involve two complementary processes. The first process involves the genetic transformation of one or more plant cells of a Specifically characterized type. The term "transformation" as used herein means that a foreign gene, typically in the form of a genetic construction, is introduced into the genome of the individual plant cells. This introduction is typically through the aid of a vector, which is integrated into the genome of the plant. The second process then involves the regeneration of the transformed plant cells into whole sexually competent plants. Neither the transformation nor regeneration process need be 100% successful, but must have a reasonable degree of reliability and reproducibility so that a reasonable percentage of the cells can be transformed and regenerated into whole plants.

Genetic Engineering of Cotton

Although successful transformation and regeneration techniques have been demonstrated in model plant species. (Barton et al., *Cell* 32:1033 (1983), wherein the transformation and regeneration of tobacco plants was reported) similar results with cotton have only been achieved relatively recently. Umbeck et al. *Bio/Technology*, 5[3] 263–266 (1987); Firoozabady et al., *Plant Mol. Bio.* 10: 105–116 (1987); Finer et al., *Plant Cell Rep.* 8: 586–589, 1990.

Successful transformation and regeneration of genetically engineered cotton plants has the potential to be of significant value to this agriculturally important crop. One of the most important benefits potentially achievable from genetically engineering cotton plants is the alteration and modification of cotton fiber quantity and quality.

Cotton Fiber

Cotton is one of the most important cash crops. Cotton fiber (seed hair) is a differentiated single epidermal cell of the ovule. At maturity the fiber cell consists of a cell lumen, primary cell-wall and secondary cell-wall. The primary cell-wall is made up of pectic compounds, cellulose, and small amounts of protein. The secondary cell-wall consists of cellulose. At maturity, the cotton fiber contains 87% cellulose.

Cotton fiber development can be divided into initiation, primary cell-wall synthesis stage, secondary cell-wall deposition stage, and maturation phases. Many hundreds of genes are required for the differentiation and development of cotton fiber. Work on in vitro translated fiber proteins (Delmer et al., *J. Cell Sci. Suppl.* 2: 33– 50, 1985), and protein isolated from fiber (Graves and Stewart, *J. Exp. Bot.* 39: 59–69, 1988) clearly suggests differential gene expression during various developmental stages of the cell. However, none of the genes involved in the biosynthesis of the large numbers of fiber-specific structural proteins, enzymes, polysaccharides, waxes or lignins have been identified. Since these genes and their interactions with environment determine the quality of fiber, their identification and characterization is considered to be an important aspect of cotton crop improvement. The current invention is designed to approach fiber modification through genetic engineering. Such an endeavor requires fiber-specific promoters, genes that will modify fiber properties, and an efficient transformation technique.

The quality of the cotton fiber is dependent on such factors as the extent of elongation and degree of secondary wall deposition. It is assumed that a number of genes as well as environmental factors regulate the physical characteristics of the fiber, such as length, thickness and micronaire value. However, the genes responsible for cellulose synthesis and fiber development in cotton plants are heretofore entirely uncharacterized at a molecular level.

The most commercially useful plant fiber is derived from cotton (*Gossypium arboreum, Gossypium herbaceum, Gossypium barbadense* and *Gossypium hirsutum*). However, there are other fiber-producing plants. These plants include the silk cotton tree (Kapok, *Ceiba pentandra*), desert willow, creosote bush, winterfat, balsa, ramie, kenaf, hemp, roselle, jute, sisal abaca and flax.

Promoters

Promoters are DNA elements that direct the transcription of RNA in cells. Together with other regulatory elements that specify tissue and temporal specificity of gene expression, promoters control the development of organisms. Thus, there has been a concerted effort in identifying and isolating promoters from a wide variety of plants and animals.

Many promoters function properly in heterologous systems. For example, plant gene promoters such as rbcS, Cab, chalcone synthase and protease inhibitor from tobacco and Arabidopsis are functional in heterologous transgenic plants. (Reviewed by Denfey, et al. *Science* 244: 174–181, 1989). Specific examples of transgenic plants include tissue-specific and developmentally regulated expression of soybean 7s seed storage protein gene in transgenic tobacco plants (Chen, et al. *EMBO J.* 7: 297–302, 1988.) and light-dependent organ-specific expression of *Arabidopsis thaliana* chlorophyll a/b binding protein gene promoter in transgenic tobacco (Ha and An, *Proc. Nat'l. Acad. Sci. USA* 85: 8017–8021, 1988). Similarly, anaerobically inducible maize sucrose synthase-1 promoter activity was demonstrated in transgenic tobacco (Yang and Russell, *Proc. Nat'l. Acad. Sci USA*, 87: 4144–4148, 1990). Tomato pollen promoters were found to direct tissue-specific and developmentally regulated gene expression in transgenic Arabidopsis and tobacco (Twell et al., *Development* 109: 705–713, 1990). Thus, some plant promoters can be utilized to express foreign proteins in plant tissues in a developmentally regulated fashion.

SUMMARY OF THE INVENTION

The present invention is a method of creating a transgenic fiber-producing plant. This method comprises the steps of constructing a plant expression vector that comprises a protein-coding sequence and a promoter DNA sequence and introducing the expression vector into a fiber-producing plant. The protein coding sequence is expressed in the fiber cells of the fiber-producing plant. By "protein coding sequence" we mean a sequence that encodes at least a portion of a protein and is in either the sense or antisense orientation. By "expressed" we mean to include sequences expressed as RNA and as protein. Preferably, the DNA sequence is homologous to a sequence selected from the group consisting of the gene E6 4.5 Kb Mbo I/Nco I fragment; the gene E6 2.7 Kb Mbo I/Nco I fragment; the gene E6 4.1 Kb Nco I fragment; the gene E6 3.9 Kb Mbo I/Nco I fragment; the gene E6 3.2 Kb Mbo I/Nco I fragment; the gene H6 321 bp Fsp I/Sal I fragment; the gene B6 2.3 Kb Bam HI/Xho I fragment; the gene E9 7.0 Kb Xho I/Nco I fragment; the gene A12 3.5 Kb Mbo I/Sma I fragment; the gene A-11 2.1 Kb Mbo I/Eco RI fragment; the gene B8 2.2 Kb Bam HI/Bst BI fragment; and the gene B12 3.1 Kb Eco RI/Sty I fragment. The homology to the sequence is sufficient to provide promoter activity.

Also preferably, the DNA sequence is homologous to a sequence selected from the group consisting of SEQ ID NOs: 20–29. The homology is sufficient to provide promoter activity.

The present invention is also a method of obtaining a DNA sequence capable of promoting gene expression in fiber cells. The method involves first obtaining a genomic library prepared from the DNA of a fiber-producing plant. This genomic library is screened with a nucleotide sequence that is homologous to an RNA sequence preferentially expressed in fiber cells or with a nucleotide sequence from a genomic clone homologous to a fiber-specific RNA. A homologous genomic sequence is selected by this screening. A promoter sequence is isolated from the genomic sequence. Preferentially, the genomic library is screened with a nucleotide sequence sufficiently homologous to a sequence selected from the group consisting of SEQ ID NOs: 2–29 to hybridize to a genomic sequence with promoter activity.

It is an object of the present invention to genetically engineer cotton plants and lines and other fiber-producing plants and lines.

It is another object of the present invention to genetically engineer fiber-producing plants in order to alter fiber quantity and quality.

It is another object of the present invention to identify promoters which regulate fiber production or fiber-specific genes in cotton or other fiber-producing plants.

It is another object of the present invention to express foreign genes in a plant in a fiber-specific manner.

It is a feature of promoter DNA sequences identified by the present invention that these promoters may be identified in one plant yet useful in another fiber-producing plant.

It is another feature of the promoter DNA sequences identified by the present invention that they contain DNA sequences sufficient to direct transcription and that they contain DNA sequences sufficient for tissue-specific transcription.

It is an advantage of the present invention that genetically-engineered cotton plants with altered fiber quantity or quality may be able to produce progeny with this trait.

Other objects, features and advantages of the present invention will become apparent upon examination of the specification, drawings, and claims.

BRIEF DESCRIPTION OF THE DRAWINGS

FIGS. 1A and 1B are a set of restriction maps of cotton genomic fragments assayed for promoter activity.

DETAILED DESCRIPTION OF THE INVENTION

Figure 1B:
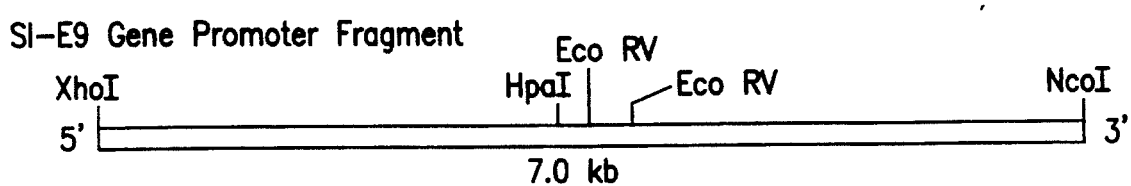
Figure 1B:
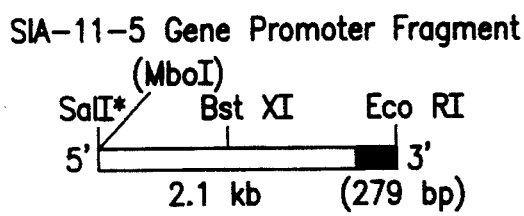
Figure 1B:
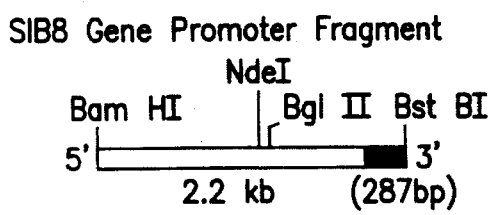
Figure 1B:
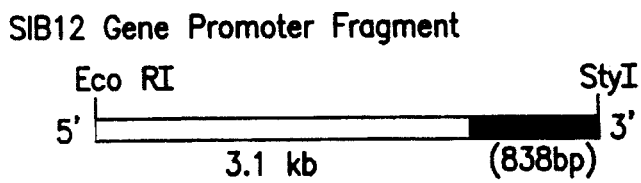
Figure 1B:
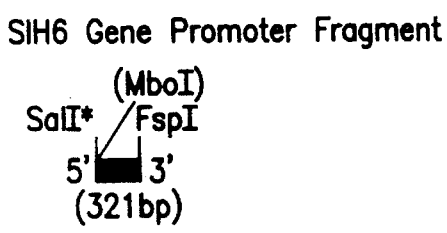
Figure 1B:
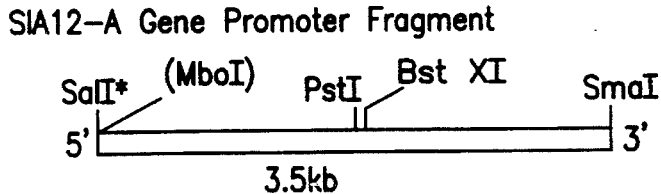

These objects and others are fulfilled by the present invention which involves a method of creating transgenic fiber-producing plants. In many instances it is desirable for the transgene to be developmentally regulated so as to be expressed only in fiber cells at a proper developmental stage. This regulation can be most expeditiously accomplished by promoters capable of preferential promotion. These promoters may be obtained by using cDNA clones from fiber-specific mRNAs to find genomic clones from a genomic library of the plant. From the genomic clone, the entire fiber-specific gene, including developmentally regulated promoter and regulatory sequences, can be isolated.

Therefore, the method first involves identifying promoters that preferentially promote gene expression in fiber cells. (By "preferentially promote" we mean that the gene is either expressed only in fiber cells or is expressed in fiber cells more actively than it is expressed in other plant tissue cells.) One way to identify suitable promoters is by isolating mRNA from fiber-producing cells, making a complementary DNA (cDNA) library of cDNA clones from the mRNA, and screening the cDNA library with cDNA generated from other tissues to identify and eliminate RNAs which are expressed in tissues other than those which produce fiber. This screening procedure will result in the identification of cDNA clones that are expressed preferentially in fiber cells.

The sequences of eighteen cDNA clones from fiber-specific mRNAs are given below at SEQ ID NOs: 2–19.

After the identification process is complete, fiber-specific cDNA clones may be used to screen genomic clones created from the DNA of fiber-producing plants. This screening process results in the selection of genomic clones with sequences homologous to the fiber-specific cDNAs. Because a fiber-specific promoter will be upstream from a sequence that is expressed specifically in a fiber cell, the promoter sequence may be identified on this genomic clone. These promoter sequences may be excised and attached to genes which if expressed in fiber cells would alter fiber quality or quantity. (Although the plant may be any of a number of varieties of fiber-producing plants, cotton (Gossypium) plants are the preferred plants for purpose of the present invention).

The present invention is preferably performed with one of twelve cotton genomic DNA fragments that we have identified as containing promoter activity. SEQ ID NOs: 20–29 represent the DNA sequences of ten of these fragments. Some of the ten fragments have only been partially sequenced. Two of the fragments, the gene E9 7.0 Kb Xho I/Nco I fragment and the gene A12 3.5 Kb Mbo I/Sma I fragment, have not been sequenced.

A sequence that is only a portion of one of these twelve identified fragments may also contain promoter activity because it is not necessary for a DNA fragment to contain an identical nucleotide sequence to be functionally identical to the promoter sequences described here. The sequence must only be sufficiently homologous to the fragment to retain promoter activity. Some nucleotide deletions, additions, and replacements, either naturally occurring or artificially induced, will have only a minor impact on gene expression.

The twelve promoter fragments may be truncated to determine the smallest fragment capable of tissue-specific expression. Methods of truncating a clone include deleting sequences and digesting the clone with a restriction enzyme or other nuclease. These methods are commonly known in the art of molecular biology. The promoter assay described below will enable one to determine whether or not a specific portion of DNA contains promoter activity. Creation of a transgenic plant enables one to determine whether a DNA fragment contains a sequence sufficient for tissue specificity.

Another way to obtain a sequence capable of preferentially promoting expression in fiber-producing plants is to probe a library of DNA obtained from a fiber-producing plant with a probe prepared from SEQ ID NOs: 2–19 (the fiber-specific cDNAs) or SEQ ID NOs: 20–29 (the genomic fragments). The DNA probe must only be of a length sufficient to hybridize specifically to a suitable clone. If a sequence from a fiber-specific cDNA clone is used, one will isolate the genomic clone homologous to that cDNA. Because promoter sequences are found upstream from the sequences homologous to the cDNA clone, one must examine these upstream sequences to find the promoter.

If one wishes to recreate the twelve fragments we have assayed for promoter activity, one would first screen a cotton genomic library with a probe prepared from SEQ ID NOs: 2–29. For example, if one wished to recreate the gene B6 2.3 Kb Bam HI/Xho I fragment, one would screen the genomic library with a probe prepared from SEQ ID NO: 29 (the genomic fragment) or SEQ ID NO: 15 (B6 cDNA). The identified genomic clone would be subjected to restriction digests with Bam H1 and Xho I to locate the 2.3 Kb fragment.

After a fiber-specific promoter has been identified and isolated, the promoter must be placed upstream of a gene whose expression is desired. Preferably, the product of this gene is capable of altering fiber quality or quantity. Conventional molecular biological techniques may be used to create suitable constructs.

These constructs must be transformed into a cotton plant or cell. Stable integration and expression of foreign genes in cotton plants has been demonstrated and repeated. Umbeck et al., *Bio/Technology*, 5[3]:263–266 (1987); Firoozabady et al., *Plant Mol. Biol.*, 10:105–116 (1987). Using the techniques taught in these papers, the transformation of cotton tissues is accomplished by Agrobacterium infection and regeneration. Although a lengthy process, the Agrobacterium-mediated transformation of cotton has also been practiced by other laboratories and can now readily be replicated by those of ordinary skill in plant genetic engineering.

It is to be understood, however, that other methods for the transformation of cotton plants and lines are being studied, and that the transgenic cotton plants and lines with fiber genes introduced into them will prove advantageous and useful regardless of the method of transformation of the original tissues. Specifically, it has now been demonstrated that higher plants can be stably genetically transformed by particle-mediated transformation techniques, which avoid many of the difficulties and delays inherent in plant regeneration required by Agrobacterium plant transformation. McCabe et al., *Bio/Technology*, 6[8]: 923–926 (1988). Recent research results suggest that routine particle-mediated transformation of cotton is to be expected shortly.

The present invention is a useful genetic engineering tool for the introduction of altered fiber-specific characteristics into cotton plants. The identification and introduction of fiber-specific promoters from one plant variety to another can be extended to include other exotic plants that produce fiber. Many of these plants will have fiber-specific promoters with one or more desirable qualities, which can be incorporated into a cotton plant.

The promoters of the present invention can be utilized in modulating the synthesis of fiber proteins or to introduce non-fiber proteins into fiber in a tissue-specific manner. To determine the sequences within a gene necessary for fiber-specific expression, nucleotide sequences of the coding region and regions flanking the coding region can be subjected to computer analysis to identify sequence patterns that correspond to consensus regulatory elements. Potential regulatory elements are usually present at the 5' flanking region of the gene, 30 to 100 bases upstream from the transcription start site in eukaryotic genes (for reviews see Breathnach and Chambon, *Annu. Rev. Biochem.* 50: 349–383, 1981; Johnson and McKnight, *Annu. Rev. Biochem.* 58: 799–839, 1989). In addition to the promoter (TATA box) other consensus sequences such as the CATC box and the CACA box, may also be present in specific groups of genes. Messing, J. et al., in *Genetic Engineering of Plants, an Agricultural Perspective,* Kosuge, et al. eds. pp 211–227 (1983); Forde, B. G. et al., *Nucl. Acid Res.* 13:7327–7339 (1985); Goldberg, R. B. *Philos. Trans. Roy Sci. B*314:343–353 (1986). A search of the 5' flanking sequences of the gene can identify these sequence patterns.

The presence of these consensus sequences in the 5' region is an indication of promoter activity, but the presence of these consensus sequences is not conclusive that the identified DNA segment is the true promoter. This is because many concensus sequences can be located in a given gene. Therefore, true identity of the promoter element requires other promoter assays.

One may use a transient reporter gene expression system to assess promoter activity. In such an assay, the fragment to be assayed would be linked to a reporter gene and used to transform a plant cell. Useful reporter genes include chloramphenicol acetyltransferase (CAT), luciferase (Lux) and β-glucuronidase (GUS). Alam and Cook, *Anal. Biochem.* 188: 245–254, 1990; Jefferson, *Plant Mol. Biol. Rep.* 5: 387–405, 1987. We have described a reporter gene assay in our examples. Further confirmation of the promoter activity and tissue-specific and developmental expression can be obtained by stably integrating a chimeric construct comprised of the DNA segment and reporter gene into plants or animals and following the reporter gene's expression through development.

Another approach to creating cotton plants with altered fiber characteristics is to create antisense genetic constructs with fiber-specific promoters to inhibit or lessen the expression of one or more fiber genes in fiber cells. The theory behind antisense genetic constructs is that the production of RNA strands in the cells of an organism which are complementary to the mRNA of an endogenous gene will result in hybridization of the antisense RNA to the native mRNA resulting in decreased expression of the mRNA gene. Smith, et al. *Nature* 334 724–726, 1988; Bird, et al. *Bio/Technology* 9: 635–639, 1991; Van der Krol, et al. *Gene* 72: 45–50, 1988. Thus, in an antisense construct, a complete coding sequence for the mRNA is not needed. All that is needed is a sequence of sufficient length to construct a selectively hybridizing antisense RNA. Thus, the cDNA clones discussed below are of particular utility for this approach.

The following is a description of the process and materials used to identify fiber-specific promoters and to transform cotton plants. Although reference to cotton is specifically made, it is within the scope of the present invention to substitute other fiber-producing plants.

EXAMPLES

1. Isolation of RNA From Fiber

Fiber cells at different stages of development from fiber-producing plants were collected and quick-frozen in liquid nitrogen. Specifically, fiber cells from 15 and 23 day-old Coker 312 or 10 day-old Sea Island bolls were collected and quick-frozen. The frozen fiber cells were then powdered in a mortar in liquid nitrogen and homogenized in a homogenization buffer for 1.5 minutes using a polytron at full speed. The homogenization buffer included the following ingredients: 5M Guanidine isothiocyanate; 0.2M Tris-acetate (pH 8.5); 0.7% Beta-mercaptoethanol; 1% polyvinyl pyrrolidone (PVP, MW 40 Kd), and 0.62% sodium lauroyl sarcosine. Beta-mercaptoethanol and PVP were added just before use. A ratio of 1:2 of tissue (weight) to buffer (volume) was used.

The homogenate was filtered through Mira cloth and layered over a 1.5 ml pad of 5.7M cesium chloride as described by Chirgwin, J. M. et al. Biochemistry, 18: 5294–5299 (1979). The homogenate was then centrifuged for 18 hours at 36,000 rpm in a SW 50.1 rotor at 20° C. After centrifugation, the RNA was collected as described by Chirgwin et al. (supra).

The RNA was then further purified by phenol:chloroform extractions and precipitations in the presence of ammonium acetate as described for DNA by Crouse, et al., *Focus*, 9[2]: 3–5 (1987). Poly(A)+RNA was obtained by oligo-(dT) chromatography as described by Maniatis, et al., in *Molecular Cloning: A Laboratory Manual*, Cold Spring Harbor Laboratory, Cold Spring Harbor, N.Y., (1982).

2. Library Construction and cDNA Clone Identification

Complementary DNA (cDNA) libraries were prepared from the mRNA according to the protocol developed by D'Alessio et al., locus, 9[1]: 1–4 (1987) with the following exceptions: The first strand of cDNA was synthesized using a primer having the following sequence dATGCTGG-TACC(T)$_{15}$ (SEQ ID NO: 1); the second strand synthesis was carried out as described by D'Alessio et al., supra, for tailing. The poly-(dC) tails were added to the double-stranded cDNA and then annealed to poly-(dG)-tailed pBR322 plasmid vector (Bethesda Research Laboratories). The recombinant plasmids were used to transform *Escherichia coli* (*E. coli*) RR1 strain as described by Hanahan in *DNA Cloning a Practical Approach*, Vol. 1 (1985) p. 109–135. The transformed cells were selected on agar plates containing the antibiotic tetracycline (12 mg/liter).

Separate cDNA libraries were constructed from the mRNAs from 10-day, 15-day, and 23-day-old fiber cells. For the 10-day fiber cell mRNAs, an oligo-(dT) primer was used for cDNA synthesis instead of the primer described above. The 10-day cells were selected to be representative of genes active during the primary cell wall stage of cell development. In the 15-day-old cell, both primary cell wall and secondary cell wall synthesis systems are active. The 23-day-old cells were selected to be representative of genes active principally during secondary wall synthesis.

The clones in the library were then transferred to nitrocellulose filters and duplicate filters were made according to Hanahan, et al., Gene, 10: 63–67 (1980). About 25,000 clones from the 15-day and 23-day libraries were screened using the following procedure. $^{32}$P-labelled single-stranded cDNA probes were prepared from poly(A)+ RNAs using $^{32}$P-dCTP and reverse transcriptase as described by Maniatis et al., supra. Probes were prepared from poly(A)+RNAs of 15-day, 23-day old fiber producing cells, and from 0-day ovule, leaf, root and flower cells. Prewashings, prehybridizations, hybridizations and washings of the filters were performed as described in detail in John et al., *Proc. Natl. Acad. Sci. USA*, 81: 5628–5632 (1984).

The autographic signals from filters hybridized with $^{32}$P-labelled cDNAs from the different tissues were then compared. The clones which hybridized to cDNAs from fiber producing cells, but not to cDNAs from other tissues, were selected. The resulting clones were then subjected to a second cycle of differential screening as described above and additional clones were eliminated as non-fiber specific. This process was continued for a third and then a fourth time. This repetitive screening was to eliminate clones which showed hybridization to other than cDNAs from fiber producing cells.

The final collection of clones were then subjected to northern analysis. For this analysis, poly(A)+RNA from different tissues were denatured in the presence of formaldehyde and size-fractionated on 1.5% agar/formaldehyde gels as described by John et al., supra. The RNAs were then blotted to nitrocellulose and probed with $^{32}$P-labelled inserts of each individual clone. The clones that showed hybridization to only RNAs from fiber cells were selected. This screen resulted in the identification of cDNAs specific to five fiber specific genes. All manipulations on plasmid DNAs such as isolation, purification on cesium chloride gradients, restriction digestion, insert purifications by gel electrophoresis and electroelutions and $^{32}$P-labelling by nick-translations have been described previously (Maniatis et al., supra and John et al., supra).

The cDNA library from the 10-day old cells was then screened using a subtractive hybridization procedure as follows. The $^{32}$P-labelled cDNA from fiber was hybridized to excess biotinylated mRNA isolated from leaf tissue. The cDNA-biotinylated mRNA hybrids and the excess biotinylated mRNAs were separated from unhybridized cDNA by extraction with avidin in phenol:chloroform. The streptavidin was partitioned into the organic phase along with any biotinylated nucleic acid while the single-stranded cDNA remained in the aqueous phase. This procedure has been described elsewhere, Duguid et al., *Proc. Natl. Acad. Sci. USA*, 85:5738–5742 (1988).

Substractive hybridization screening of 4788 clones of the 10-day cell library with leaf cDNAs resulted in 800 clones not present in the leaf. These clones were then screened by cDNAs generated from ovule, flower and root mRNAs. The results of this screening were 79 putative fiber-specific clones. The duplicate clones which hybridized to each other were detected by the procedure of polymerase chain reaction (PCR)(Saiki et al., *Science*, 239:487–491 (1988)), Southern blotting and hybridization. The PCR reaction was carried out by first mixing 10 microliters of bacterial culture of the cDNA clone added to 90 microliters of distilled water. 20 microliters of that mixture was added to a PCR reaction buffer of 50 mM KCl, 10 mM Tris-HCl pH 8.0, 2.5 mMMgCl$_2$, 0.01% gelatin, 200 μM each of dATP, dCTP, dTTP and dGTP, 12.5 picomolar each of sense and antisense primers for pBR322, and 0.5 units of Taq polymerase. The final reaction volume was 52 microliters. The PCR reactions were carried out in a Perkin-Elmer-Cetus thermocycler.

The amplified DNA from the PCR reactions was separated by agarose gel electrophoresis and blotted onto nitrocellulose by the method of Southern, *J. Mol. Biol.* 98:503–517 (1975). One or more bacterial clones from the same group was amplified by the same procedure and the products also separated on agarose gel. The amplified insert DNAs were then excised from the gel and purified by electroelution. The purified DNAs, labelled with $^{32}$P by nick-translation, were hybridized with the Southern blot. Thus, the cross-hybridizing clones were identified in this fashion. This procedure resulted in the identification of 19 putative fiber-specific clones. The clones were further analyzed by northern blots. Three of the clones were found to be fiber-specific. Another five of the clones were found to be differentially expressed to a higher degree in fiber and to a lesser degree in other tissues. Fiber-specific cDNA clones were then used as probes to screen genomic libraries and isolated cross-hybridizing genomic clones.

3. Characterization of Fiber-Specific cDNA clones

In the following sections, we describe each of the fiber cDNAs, their corresponding genes and their promoters. The nomenclature is as follows: CK=Coker, SI=Sea Island; FB15, FB10 =15 or 10 day old bolls; the last remaining letters and numbers signify the individual cDNA isolate.

a. CKFB15A1-E6 cDNA clone (E6 cDNA)

This cDNA clone for a fiber gene has an insert of 983 base pairs which hybridizes to 1.0 and 1.1 Kb RNAs. The RNA is expressed in fiber and not in root. Flower leaf and ovule RNAs show weak hybridization.

The E6 RNA was found to be developmentally regulated. Its steady-state concentration increases immediately after anthesis. Our quantification of E6 transcript in fiber using in vitro synthesized E6 RNA as a control, shows that 20 μg of RNA from 20-day-old fiber contains about 3.5 μg of E6 RNA. Thus, E6 RNA is an abundant fiber RNA.

Hybrid selection translation experiments showed that E6 codes for two polypeptides of 26 and 30 kD. The E6 clone cross-hybridizes with Pima and Naked seed cotton fiber cell RNAs. The clone also cross-hybridizes with a number of plants belonging to Gossypium species. Thus, DNAs from Pima and Sea Island (*G. barbadense*) PD3 and DP50 (*G. hirsutum*) and plants belonging to *G. longicalyx* and *G. somalense* all showed hybridization. In addition, plants belonging to another species of family Malvaceae, the Hibiscus are also found to have conserved E6 gene. DNAs of *H. sabdariffa* L. cv., Rosselle, Kapok (*Ceiba pentandra*) belonging to family Bombacaceae, Hemp (*Cannabis satira*) belonging to family Moraceae also showed hybridization to E6 gene. We also confirmed that E6 or a homologous gene is present in *Gossypium darwinii*, *Gossypium herbaceum* L. cv. Jayadhar and Tzuyung, *Gossypium anomalum*, *G. australe*, *G. nelsonii*, *G. arboreim* L., cv., Nanking and Liaochung, *G. thurberi*, *G. davidsonii*, *G. raimondii*, *G. stocksii*, *G. somalense*, *G. longicalyx*, and *F. bickii*. Thus, the E6 sequence is conserved in most of the plants belonging to family Malvaceae and also found in two other families Bombacaceae and Moraceae. Many of these plants produce seed hair or bast fiber. Interestingly, we did not detect E6 hybridization in the DNAs of soybean, corn, tobacco or the cellulose producing bacterium Acetobacter (*A. xylinum*). These studies imply that E6 gene may have functions in the formation of seed hair or bast fiber cells.

The complete nucleotide sequence of E6 insert is presented as SEQ ID NO: 2. This sequence contains a long open reading frame extendening from position 1 to position 748. On this same open reading frame, start codons appear at positions 34, 61 and 94. If the first codon is the initiation site for the protein, the 714 nucleotide reading frame would yield a 238 amino acid protein. E6 cDNA clone was deposited with ATCC at Accession Number 67809.

SEQ ID NO: 2 also contains an additional 84 residues and a stretch of poly(A) that originate from clone PCKFB15-B3. This clone is identical to pCKFB15A1-E6 except for the presence of additional residues at the 3' end.

b. CKFB15A1-H6 cDNA clone (H6 cDNA)

H6 cDNA hybridizes to a developmentally regulated RNA of 950 bases. H6 RNA was not detected in leaf, flower, ovule and root. The H6 clone cross-hybridizes to Pima, PD3 and Sea Island DNAs and is encoded by one or two genes in the cotton genome. The H6 clone had an insert of about 500 base pairs.

To obtain a full length cDNA clone, primer extension of H6 clone mRNA was conducted using an oligomer and fiber cell mRNA by the protocol described by Dean et al., *Nucleic Acid Res.* 15:4655–4668 (1987). The primer-extended product was then cloned into the Pst 1 site of dG-tailed pBR322. The complete sequence of H6 insert clone and the primer extended H6 (CKFBH6–10) were determined. Together, these two sequences make up the complete 913 base pair sequence of H6. This sequence, SEQ ID NO: 3 below, has a single long open reading frame with an initiation codon at position 71. Sequence analysis using a Genetics Computer Group software package (University of Wisconsin) for identifying protein coding sequences also suggest a single protein coding region between residue positions 71 and 710. The nucleotide-derived amino acid composition shows a proline rich peptide (35 mole % proline) of 214 amino acids. A total of five amino acids (alanine, proline, leucine, serine and valine) make up 74.3% of the protein. The sequence includes 17 pentapeptide repeats of X-Y-Pro-Pro-Pro repeat units where X and Y are serine, alanine or theronine. The H6 protein is clearly distinct from previously known proteins of plant cell walls, such as extensin. H6 cDNA clone was deposited with ATCC at Accession Number 67810.

c. CKFB15A1-C12 cDNA clone (C12 cDNA)

C12 RNA is 1.1 Kb bases long and is developmentally regulated. It is not expressed in root, leaf, ovule and flower. The C12 clone cross hybridizes with Pima, PD3 and Sea Island genomic DNAs, and is encoded by one or two genes. The C12 clone has an insert of about 659 base pairs. The sequence is presented as SEQ ID NO: 4 below. The C12 cDNA clone has been deposited with ATCC at Accession Number 67808.

d. CKFB15A1-B8 cDNA clone (B8 cDNA)

B8 RNA is 1100 bases long and is developmentally regulated. It is not expressed in leaf, root, ovule and flower. B8 cross-hybridizes to Pima, PD3 and Sea Island genomic DNAs and is encoded by one or two genes. The B8 cDNA clone has an insert of 690 bp, the sequence of which is presented at SEQ ID NO: 5 below. It has been deposited with ATCC at Accession Number 67807.

e. CKFB10-B12 cDNA clone (B12 cDNA)

B12 cDNA hybridizes only to fiber RNA in northern analysis. The transcript size is 1 Kb. The 727 base pair insert in B12 has been sequenced and is presented as SEQ ID NO: 6 below. The developmental pattern of expression of the clone showed that maximum concentration of B12 mRNA is present 10 to 20 days after anthesis. The concentration of B12 RNA in 24 day old cotton fiber cells is very low.

f. CKFB10-A11 cDNA clone (FB10-A-11 cDNA)

FB10-A-11 RNA is also fiber-specific. The cDNA insert size is 1 Kb. Two mRNA transcripts (1.1 and 0.9 Kb) from fiber cells hybridize to FB10-A-11. The sequence for FB10-A11 is presented as SEQ ID NO: 7 below.

g. CKFB10-D7 cDNA clone (D7 cDNA)

This cDNA clone hybridizes to an RNA of about 500 bases in length. It is not detected in ovule, leaf, flower or root RNA from cotton. The sequence of this cDNA clone is presented as SEQ ID NO: 8 below.

h. CKFB10-C2 cDNA clone (C2 cDNA).

This cDNA clone hybridizes to an mRNA highly expressed in cotton fiber cells but also detected as weakly present in petal tissues. The cDNA insert is 668 bp and hybridizes to an RNA of 1.1 Kb. The sequence is listed as SEQ ID NO: 9.

i. CKFB10-C12 cDNA clone (C12 cDNA)

The cDNA clone C12 has an insert size of 609 base pairs. The transcript is expressed in fiber cells, but is also expressed at low levels in petal and pollen. The cDNA hybridizes to an mRNA of 1.1 Kb. The sequence of CKFB10-C12 is shown in SEQ ID NO: 10 below.

j. CKFB10-C1 cDNA clone (C1 cDNA)

This clone hybridizes to a transcript of 450 base pairs in fiber cells. The cDNA also hybridizes very weakly to transcripts in petal and pollen. The insert size is 432 base pairs. The sequence is presented at SEQ ID NO: 11 below.

k. CKFB10-A8 cDNA clone (A8 cDNA)

This cDNA clone has an insert size of 320 base pairs and hybridizes to a 1 Kb mRNA in fiber cells. The clone also exhibits weak hybridization to leaf and to petal RNA. The sequence of the insert is presented in SEQ ID NO: 12.

l. CKFB10-A9 cDNA clone (A9 cDNA)

The cDNA clone A9 has an insert of 399 base pairs and hybridizes to an RNA of 750 bases in fiber cells. The clone exhibits weaker hybridization to RNAs from other tissues. The sequence is presented at SEQ ID NO: 13 below.

m. CKFB10-D4 cDNA clone (D4 cDNA)

Clone D4 hybridizes strongly to 10 day fiber RNA and very weakly to petal RNA. Its transcript size is 500 bases and has an insert size of 455 bp. This sequence is presented at SEQ ID NO: 14 below.

n. CKFB10-B6 cDNA clone (B6 cDNA)

B6 cDNA hybridizes to RNA of fiber. It also shows weak hybridization to leaf RNA. It has an insert size of 1.1 Kb and transcript size of 1.2 Kb. The sequence of B6 cDNA is presented at SEQ ID NO: 15.

o. CKFB10-A12 cDNA clone (A12 cDNA)

A12 cDNA hybridizes to fiber RNA only. It has an insert size of 868 bp and hybridizes to a RNA of 900 bases. The sequence of A12 cDNA is presented at SEQ ID NO: 16.

p. CKFB15-E9 cDNA clone (E9 cDNA)

This clone hybridizes strongly to fiber RNA and weakly to petal RNA. It has an insert size of 1283 bp. The sequence is presented at SEQ ID NO: 17 below.

q. SIFB-H8 cDNA clone (H8 cDNA)

H8 cDNA hybridized to fiber RNA, but not to cotton leaf, root or ovule. The H8 sequence is presented at SEQ ID NO: 18 and contains an 878 bp insert.

r. SIFB-H4 cDNA clone (H4 cDNA)

mRNA hybridizing to H4 cDNA is expressed in fiber and to a much lesser extent in petals. The sequence of H4 cDNA is presented at SEQ ID NO: 19.

As will become apparent from the following, these cDNA clones can be used to obtain genomic clones containing fiber-specific promoters. Plant transformation vectors can therefore be constructed to transfer genes connected to these promoters into fiber-producing plants and express the gene in a fiber-specific manner.

Some of the RNA species represented by the above-identified cDNA clones are partially expressed in other tissues, such as petal or leaf. If a promoter is desired that directs expression in fiber and another plant tissue, one of these cDNA clones might be preferentially selected to search for this promoter. For example, E9 and H4 cDNAs hybridize weakly with petal RNA. If one wished to obtain a promoter that preferentially promotes expression of genes in fiber, but also promotes expression to a lesser extent in petal, one would use the E9 sequence or the H4 sequence as probes.

4. preparation of Genomic DNA and Genomic Clones

Genomic DNAs from Sea Island cotton, Coker 312 cotton and Kapok were prepared according to the methods described in *Current Protocols in Molecular Biology*, (Eds. Ausbel, F. M. et al.) Wiley, (1987), pp. 2.3.1–2.3.3, with the following modification: The frozen plant material was homogenized in extraction buffer containing 1% polyvinyl pyrrolidone. The purified genomic DNA was digested with restriction endonucleases and transferred to nitrocellulose filters by the Southern blotting technique. Southern, (supra).

The filters were then probed with nick-translated inserts of the fiber-specific cDNA clones previously identified. The hybridization and blot washing conditions are described in John et al. (supra). The Southern hybridization results showed that each of the cDNA clones hybridized to only a few (one or two) bands in the genomic DNA. This result indicates that there are only one or two genes corresponding to these cDNAs in the cotton genome.

Sea Island cotton, Coker 312 cotton and Kapok genomic libraries were prepared by Clonetec, Inc., of California, in EMBL-3 or lambda DASH vectors. For the preparation of the library, the DNA was partially digested with Mbo I. 8–22 Kb DNA fragments were cloned into the Bam HI site of the vector. Inserts 10–15 Kb were present in the phages. The inserts were excised by either Sal I for EMBL-3 and lambda DASH or Eco R1 for lambda DASH. The genomic libraries were plated on *E. coli* NM 538 as described in *Current Protocols in Molecular Biology*, (supra.) The genomic library was screened with $^{32}$P-labelled inserts of the fiber-specific cDNA clones after transferring the library to nitrocellulose filters according to the methods described in *Current Protocols*, (supra) and John et al., (supra). By this method, genomic clones containing sequences homologous to the fiber-specific cDNA clones were isolated.

Subcloning of these genomic DNA inserts into plasmid or phagemid vectors was done using standard protocols. Ligated DNAs were transformed in *Escherichia coli* strain XL-1 Blue (Stratagene). Recombinant clones were selected on the basis of blue/white selection on X-gal, IPTG (5-bromo- 4-chloro-3-indoyl-beta-D-galactophyranoside; isopropyl-beta-thio-galactophyranoside) plates. The plasmid sizes of the recombinant clones were then analyzed by SDS-agarose gell electrophoresis (Sekar, V., *Biotechniques*, 5: 11–13, (1987)). The inserts of the clones were further characterized by restriction mapping and Southern analysis. *Current Protocols in Molecular Biology*, (supra). If necessary, further subcloning of smaller restriction fragments that contain the cDNA hybridizing regions was also undertaken. The above protocols enable one to determine the approximate boundaries of a given gene.

The nucleotide sequence of the gene and the corresponding cDNAs were analyzed by computer programs to determine, among other things, the tentative coding region, presence of introns and exons, 5' and 3' non-coding regions and putative protomer regions. The software that we have used for this purpose is that of Genetics Computer Group (GCG), Madison. Once the detailed sequence analysis was performed and various putative structural components of the gene were identified, we were able to confirm these findings by various experiments. For example, we used a chimeric marker gene construct that includes the promoter fragment to transform a test cell. By observing the presence or absence of the marker gene activity, one can analyze the promoter function of that DNA fragment.

5. Characterization of genomic clones

Once the genomic clones were identified, they were subcloned into plasmid or phagemid vectors for easy manipulation, as discussed above. A schematic representation of the promoter fragments that we characterized is given in FIG. 1.

The nomenclature is as follows: EMBL and DASH= Lambda vector; SI=Sea Island, CK=Coker; CP=*Ceiba pentandra*; next to last two characters=the cDNA clone that hybridized to the genomic clone; the last numbers or characters correspond to different genomic clones from a given library. The following fragment sizes are approximate.

The genomic clones we obtained and assayed are described below in Table 1. When the fragments were initially cloned, a Sal I site was added to the fragment by the cloning vector. The designation "Sal I (Mbo I)" in the following table is to emphasize that a naturally occurring Mbo I site exists adjacent to the artificial Sal I site. (The genomic fragments were originally created by a partial Mbo I digest.) All other restriction sites in Table 1 and in FIG. 1 are naturally occurring genomic sites.

| GENOMIC CLONE (Insert Size) | SUB CLONE (Insert Size) | FRAGMENT ASSAYED FOR PROMOTER ACTIVITY | SEQUENCE ID NO: AND DESCRIPTION |
|---|---|---|---|
| EMBL-SI-E6-2A 14.2 Kb Sal I (Mbo I) | SKSIE6-2AH3 6.4 Kb Sal I/Hind III | Sal I (Mbo I)/Nco I 4.5 Kb | SEQ ID NO: 20 contains 541 bp of promoter, 33 bp of 5' noncoding, 741 bp of coding and 332 bp of 3' noncoding. |
| EMBL-SI-E6-3B 15.0 Kb Sal I (Mbo I) | SKSIE6-3B 5.1 Kb Sal I | Sal I (Mbo I)/Nco I 2.7 Kb | SEQ ID NO: 21 contains 581 bp of promoter, 33 bp of 5' noncoding region, 741 bp of coding region, and 313 bp of 3' noncoding region. |
| DASH-CK-E6-1A 12 Kb Sal I (Mbo I) | SKCKE6-1A 12 Kb Sal I | 4.1 Kb Nco I | SEQ ID NO: 22 contains 567 bp of promoter, 33 bp of 5' noncoding region, 717 bp of coding region, and 301 bp of 3' noncoding region. |
| DASH-CK-E6-4A 12.2 Kb Sal I (Mbo I) | SKCKE6-4A 8.0 Kb Sal I | 3.9 Kb Sal I (Mbo I)/Nco I | SEQ ID NO: 23 contains 512 bp of promoter, 37 bp of 5' noncoding region, 726 bp of coding region, and 303 bp of 3' noncoding region. |
| EMBL-CP-E6-3A 15.3 Kb Sal I (Mbo I) | SKCPE6-3A-RV 4.8 Kb Sal I/EcoRV | 3.2 Kb Sal I (Mbo I)/ Nco I | SEQ ID NO: 24 contains 421 bp of promoter including the 5' untranslated mRNA leader, 873 bp of coding region and 324 bp of 3' untranslated region. |
| EMBL-SI-H6-4 13 Kb Sal I (Mbo I) | SKSIE6-H6-RI 1.9 Kb Sal I/ Eco RI | 321 bp Fsp I/Sal I (Mbo I) | SEQ ID NO: 25 contains 250 bp of promoter, 71 bp 5' untranslated mRNA leader, 1226 bp of coding region including a 583 bp intron and 437 bp of 3' untranslated region. |
| EMB2-SI-B12 15 Kb Sal I (Mbo I) | SKSI-B12-H3 73 Kb Hind III | 3.1 Kb Eco RI/Sty I | SEQ ID NO: 26 contains 699 bp of promoter, 139 bp of 5' untranslated mRNA leader, 841 bp of coding region which includes two introns (76 bp and 82 bp each) and 735 bp of 3' untranslated region. |
| EMBL-SI-A11-B 17.0 Eb Sal I (Mbo I) | SKSIA11-B 4.9 Kb Sal I | 2.1 Kb Sal I (Mbo I)/ Eco RI | SEQ ID NO: 27 contains 279 bp of promoter |
| EMBL-SI-B8 19.0 Kb Sal I (Mbo I) | SKSIB8-HI 9.5 Kb SRI I/ Bam HI | 2.2 Kb Bam HI/BstBI | SEQ ID NO: 28 includes 287 bp of promoter including mRNA 5' leader, 1473 bp of coding region (which includes a 510 bp intron), and a 758 bp 3' region. |
| EML-SI-B6-1A of 12.3 Kb Sal I (Mbo I) | SKSIB6-1A 123 Kb Sal I | 23 Kb Bam HI/Xho I | SEQ ID NO: 29 contains 562 bp of promoter. |
| EMBL-SI-E9 12.4 Kb Sal I (Mbo I) | SKSI-E9 12.4 Kb Sal I | 7.0 Eb Xho I/ Nco I | |
| EMBL-SI-A12-A 11.5 Kb Sal I (Mbo I) | SKSIA12-A 6.7 Kb Sal I | 3.5 Kb Sal I (Mbo I)/ Sma I | |

6. Characterization of Promoter Activity (In General)

Once the DNA was purified from the phage genomic clones (Ausubel et al., pp. 1.10.1 to 1.13.6) the insert DNAs (10 to 15 Kb) were characterized in terms of their restriction maps (supra, pp. 3.1.1 to 3.3.2). The different restriction fragments were separated on agarose gels and Southern blotted. The blots were then be hybridized to cDNA probes.

This procedure enabled us to identify smaller fragments (about 1 to 10 Kb) that contained the homologous cDNA sequence. The fragment was then subcloned (supra., pp. 3.16.1 to 3.16.11) into plasmid vectors such as pGEM5zf (Promega, Madison) or Bluescript SK, KS (Stratagene, California). All further manipulations, such as promoter identifications, transcription maps and gene size determinations were done using the subclones.

Mapping the gene transcripts by nuclease protection may also be done. Single-stranded DNA probes may be generated from the Bluescript subclones and hybridized to poly(A)+ RNA from fiber cells. The hybridized portions that are protected from nuclease action will be determined as described by Calzone et al. in *Methods in Enzymology*, Vol. 152 (Eds. Berger, S. L. and Kimmel, A. R.), 1987, pp. 611–632. Furthermore, mapping the 5' termini by cDNA primer extension is also described (supra, pp. 629–632). These strategies will determine the size of the gene, as well as precise boundaries of the gene transcript, or coding region for the fiber gene, in the subclone. Portions of the DNA may then be sequenced if desired.

It was necessary to determine whether the isolated DNA fragments had promoter activity. The genomic fragments we assayed are described in FIG. 1.

A GUS fusion construct was used to identify the cotton promoters. First, the transcription start site of the mRNA was determined by primer extension method, as described by Calzone et al. (supra). The subcloned gene fragment and a short restriction fragment or an oligomer at the 5' end was used in the primer extension. A beta-glucuronidase (GUS) coding sequence along with necessary termination signals, as well a 5' leader sequences, was used with an upstream 2–3 Kb DNA fragment from the transcription or translation start site. The GUS sequence is already readily publicly available (ATCC 67641).

Figure 2:
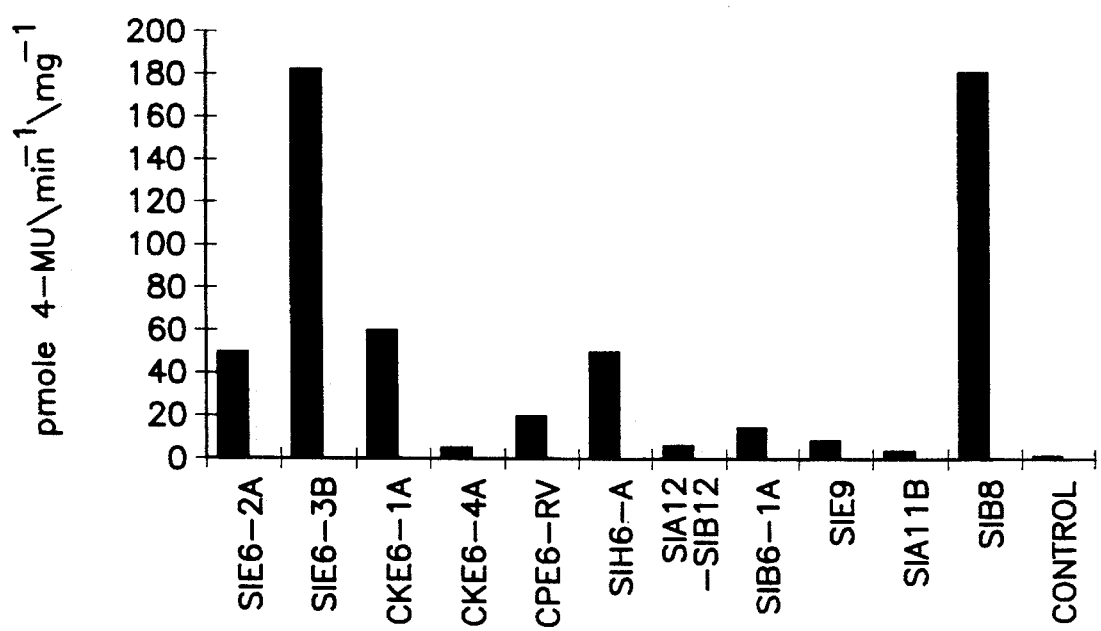
FIG. 2 is a bar graph describing the levels of promoter activity obtained in a fluorogenic assay with the fragments of FIG. 1.

It has been demonstrated that a GUS gene construct with a cauliflower mosaic virus 35 promoter (CaMV35s) promoter is functional in plant cells. Thus, when this construct was introduced through particle bombardment (described by McCabe, D. et al., *Bio/Technology*, 6: 923–926, 1988) into a plant, GUS activity was observed. If the construct containing an unknown DNA is found to be active in expressing GUS, then it can be concluded that the DNA fragment contains a promoter that directs the expression of GUS gene. Using the GUS assay, we determined that the sequences identified in Table 1 had promoter activity. FIG. 2 describes the various levels of promoter activity we found.

Using the Bluescript subclone and exonuclease/mung bean deletion procedure in which a series of clones with differing lengths of the 5' fragment are generated, one can identify minimum lengths of 5' DNA necessary to express the gene in fiber cells. These types of procedures will enable one to identify promoters from all genomic clones. Based on this knowledge, one can construct various developmentally regulated expression vectors containing fiber genes of interest and introduce them into plants.

7. Determination of Promoter Activity

A chimeric gene construct was made using the putative promoter and the reporter gene beta-glucuronidase (GUS) of *E. coli*. GUS catalyzes the cleavage of 5-bromo-4-chloro-3-indoyl glucuronide (X-Gluc). The indole derivative produced by this cleavage undergoes oxidative dimerization to form a blue dye. Cells that produce this blue dye can be detected easily. The GUS marker system has been described in detail by Jefferson, et al., in *Proc. Natl. Acad. Sci. USA* 83: 8447–8451 (1986) and in *Plant Mol. Biol. Rep.* 5:387–405 (1987). The GUS gene is publicly available (ATCC Accession No. 67641).

Chimeric plasmids were constructed by litigating a promoter-less GUS coding region along with a transcription termination signal Nos(A) at the 3' end into a vector cassette as a Nco I/Sal I fragment. An AMV 5' untranslated leader is added to the 5' end of the GUS gene as a Nco I/Xho I fragment. This construct (p2117, FIG. 3) contains unique Xho I and Nco I sites for introducing putative promoters. For example, if a cauliflower mosaic virus 35s (CaMV 35s) promoter is ligated into Xho I or Nco I site and the resulting plasmid (p2119) is introduced into plant cells by particle acceleration, GUS expression can be detected. Ellis et al., *Plant. Mol. Biol.* 17: 19–27, 1991. We have tested GUS expression by histochemical staining as well as quantitative measurements (Jefferson, R. A., supra).

The assay involves transforming a test cotton tissue, such as hypocotyl, with different plasmids. We transformed the hypocotyl tissue via a particle-mediated transformation method disclosed in U.S. Pat. No. 5,015,580, hereby incorporated by reference.

We analyzed our reporter gene constructs in two ways, through histochemical staining and through fluorogenic analysis. The histochemical staining gave a quick "yes or no" answer while the fluorogenic analysis provided quantitative data.

(a) Histochemical Staining

Histochemical localization of beta-glucuronidase activity in plant tissues is achieved by incubating freshly cut, transformed tissue sections in a solution containing 5-bromo-4-chloro-3-indoyl glucuronide (X-Gluc). X-Gluc is prepared by dissolving 5 mg of X-Gluc in 50 µl of dimethyl formamide and diluting it to 10ml with 50mM sodium phosphate buffer pH 7.0. After staining (1–3 hours at 37° C.), the tissue sections were rinsed off with 70% ethanol. Cells containing an active GUS gene turn blue.

(b) Fluorogenic Assay

The quantitative assay for GUS activity depends on the cleavage of 4-methyl umbelliferyl glucuronide (MUG) by the GUS enzyme into a fluorogenic product 4-methyl umbelliferone (MU). MU is fluorescent when its hydroxyl group is ionized. (Jefferson, R. A. supra). The fluorogenic assay is carried out as follows. Plant tissue was homogenized in extraction buffer (50 mMNaH$_2$PO$_4$, pH 7.0, 10 mM EDTA 0.1% Triton X-100, 0.1% sodium lauroyl sarcosine, 10mM β-mercaptoethanol). We included proteinase inhibitor PMSF at a final concentration of 20 µg/ml and 1% insoluble PVP. The extract, after centrifugation (300 µl) was added to 1 ml of MUG buffer. The MUG buffer is made up of 1 mM MUG in the above extraction buffer. The mixture is incubated at 37° C. and at time points 0, 20, 40, and 60 min. an aliquote (100 µl) is withdrawn and added to 1 ml stop solution (0.2M Na$_2$CO$_3$). The fluorescence at each time point is measured in a fluorocalorimeter (excitation at 365 nm, emission at 455 nm) Protein concentration of the plant extract is determined by Bradford assay using a test kit from Bio-Rad Laboratories (M. Bradford, *Anal. Biochem.* 72: 248–254, 1976). The fluorimeter is calibrated with freshly prepared MU standards. The results are given as pmole MU/mg/min. FIG. 2 describes the various results with our twelve promoter fragments.

The above system for the detection of promoters, namely transient expression of chimeric GUS plasmids introduced into hypocotyl tissues through particle bombardment, appears to be limited in that no tissue specificity of expression is observed for any of the promoters tested. Thus, promoters (LAT 52, Cab) that were proven to be tissue specific in heterologous stable transgenic plants (Twell, et al., *Mol. Gen. Genet.* 217: 240–245 (1989); Ha and An,

*Proc. Natl. Acad Sci. USA* 85:8017–8021 (1988)) are found to express GUS transiently when introduced into cotton hypocotyls by particle bombardment.

The following control experiments were conducted along with each of the promoter assays.

Figure 3:
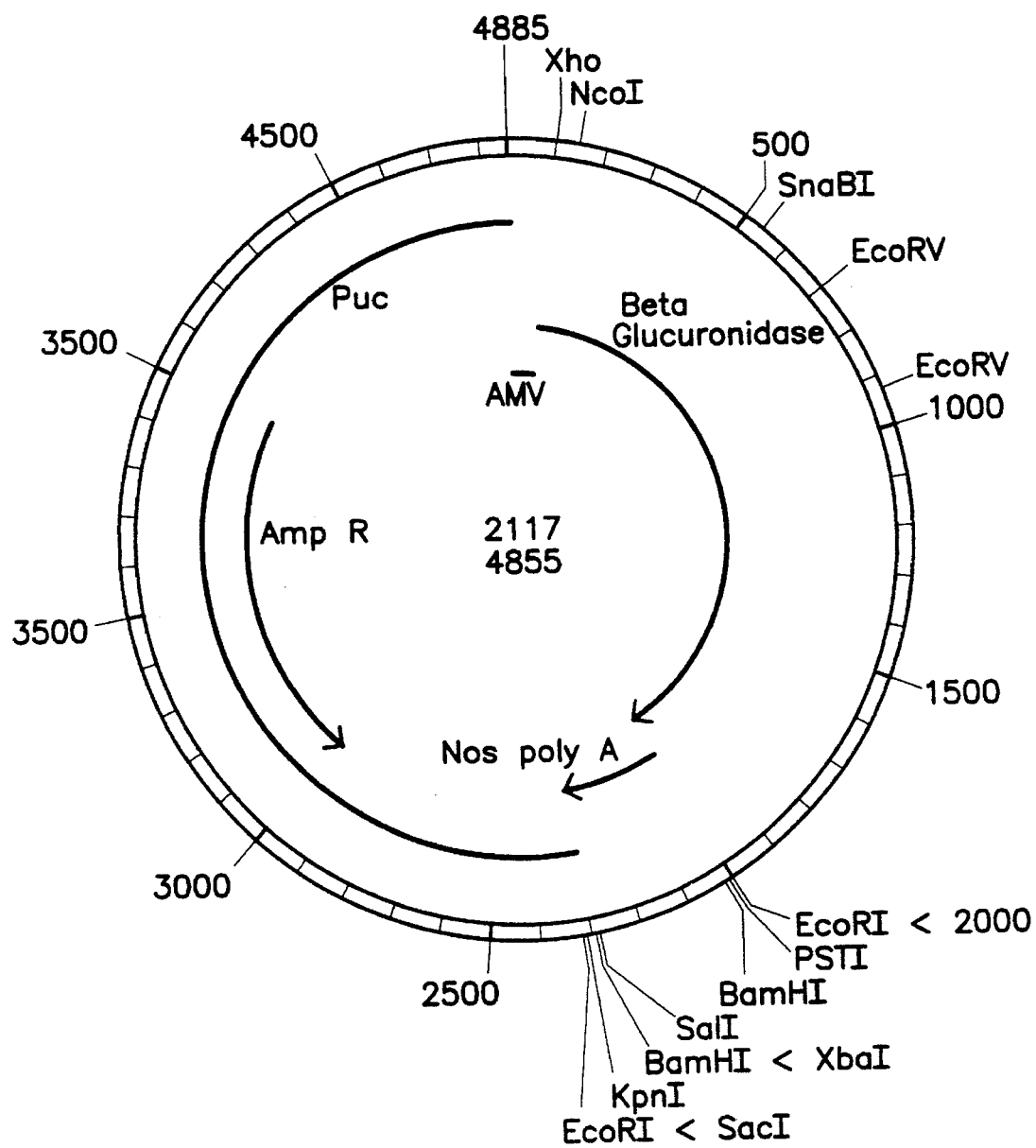
FIG. 3 is a diagram of plasmid p2117.

1. Plasmid p2117 was introduced into cotton or soybean hypocotyl tissues as a negative control. Because p2117 contains a promoter-less GUS gene, no GUS activity should be detected. FIG. 3 describes p2117.
2. The tissue was bombarded with p2119. p2119 contains a GUS gene driven by 35s promoter. This is a positive control, for GUS should always be expressed.
3. The DNA fragment being tested for activity is introduced into hypocotyl tissue. This is to demonstrate that the fragment in question has no GUS-like activity.

Using the above procedures and protocols, we have demonstrated promoter activity in the twelve promoter fragments listed in FIG. 1. The promoters exhibited different levels of expression, as FIG. 2 indicates. If one wished to create a transgenic plant with high or low expression of a certain transgene, FIG. 2 would allow one to select the appropriate promoter.

8. Transformation of plants The most common methodology used for the transformation of cells of dicot plant species involves the use of the plant pathogen *Agrobacterium tumefaciens*. *A. tumefaciens* harbors a plasmid, referred to as the tumor-inducing or Ti plasmid, which has the natural ability to transfer a segment of itself, referred to as the T-DNA (transfer-DNA), into the genome of infected plant cells. Wild-type *A. tumefaciens* use this ability to genetically transform infected cells of plants so that the plant cells become tumorous, and synthesize one of a series of compounds, known as opines, which can be metabolized by the infecting *A. tumefaciens*. Several investigators have found that by removing the bulk of the T-DNA from the Ti plasmid harbored by *A. tumefaciens,* and by replacing that T-DNA with a foreign gene construction, the Agrobacterium can transform infected plant cells with the foreign gene in such a fashion that the resultant cells are not tumorous, as plant cells infected with wild-type *A. tumefaciens* normally are. The foreign gene construction is then included in the cells of a whole plant regenerated from the transformed cells and is then inherited in a simple Mendelian manner. The construction can thus be treated as any inheritable trait for crop breeding purposes. The transformation and regeneration of cotton plants by Agrobacterium transformation has been achieved and reported. Umbeck et al. (supra) and Firoozabady et al. (supra).

Other methods of plant transformation, such as transformation by accelerated particle carried DNA, are now available (McCabe et al. supra). An apparatus capable of performing particle-mediated transformation is commercially available from BioRad. In any event, once the creation and assembly of plant expression vectors including fiber specific gene sequences is accomplished, the transformation and regeneration of cotton plants with these expression vectors is within the ability of one of ordinary skill in plant genetic engineering, and is not dependent on the method of transformation.

9. Characterization of Cotton Genes

As a specific Example of our characterization of fiber-specific promoters, our characterization of the E6 genes is disclosed in detail. Brief descriptions of other genes and promoters follow.

Two E6 genes from cultivar Sea Island (*G. barbadense*) and two genes from Coker 312 (*G. hirsutum*) were isolated and examined. These four genes have homology to each other. Detailed structural characterization of these genes is presented below.

a. Sea Island E6-2A Gene and Promoter.

The phage EMBLSIE6-2 contains a 14.2 Kb insert. Restriction mapping followed by Southern analysis showed that a 9.5 Kb Sal I fragment hybridized to E6 cDNA. The 9.5 Kb Sal I fragment was subcloned into $Sk^+$ vector (pSkSIE6-2A). Further subcloning resulted in a shorter clone (6.4 Kb) pSKSIE6-2AH3. About 541 bp of promoter region, 33 bp of 5' noncoding region, 741 bp of coding region, and 332 bp of 3' noncoding region have been sequenced and is described in SEQ ID NO: 20. In order to identify the promoter region, plasmid pSKSIE6-2AH3 was digested with Nco I and Bam HI to liberate three fragments. The vector and upstream 5' noncoding fragment of the gene (4.5 Kb insert and 3 Kb vector) was gel purified and subjected to Elutip-d column elution.

Figure 4:
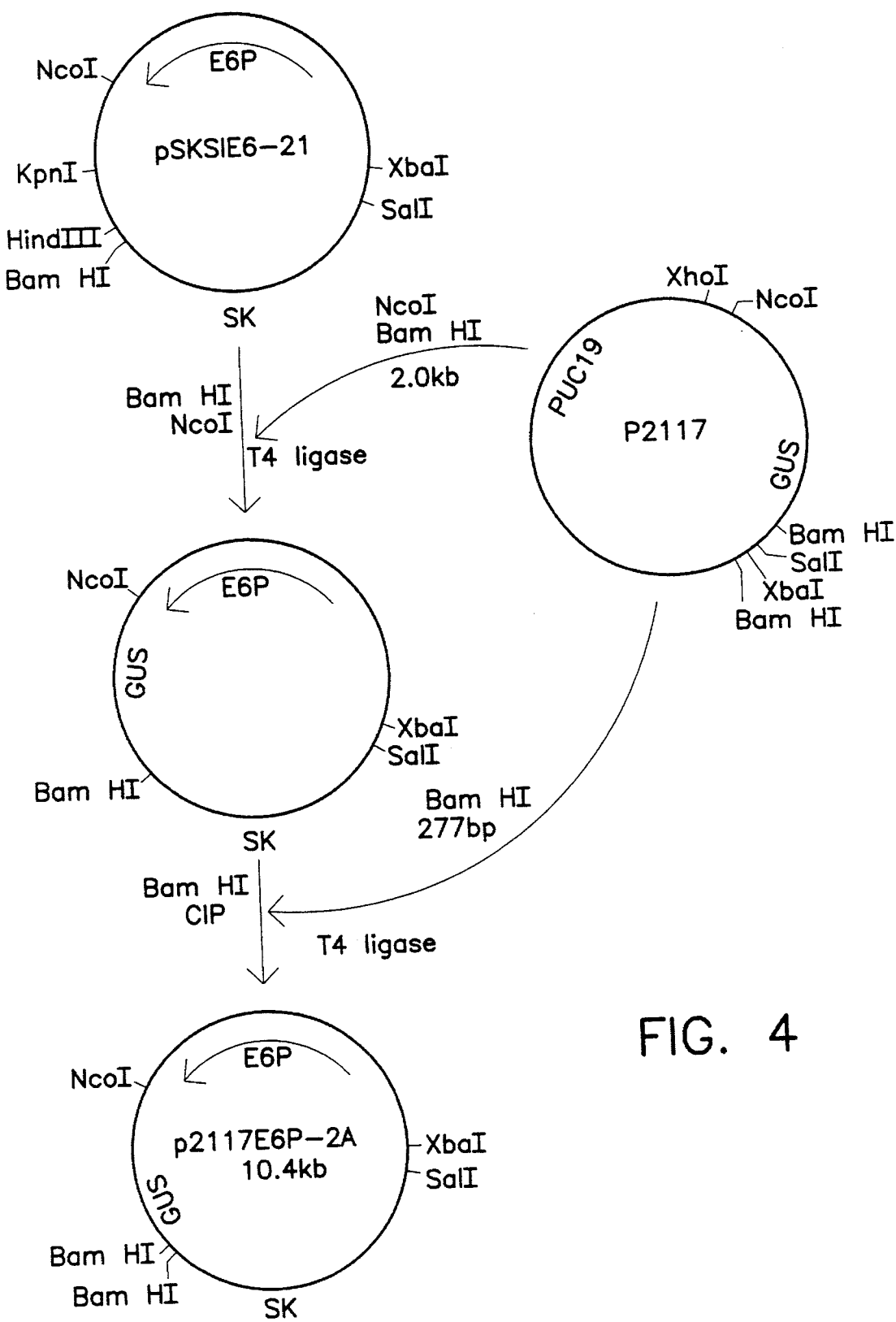
FIG. 4 is a diagram of the construction of plasmid p2117E6P-2A.

Plasmid 2117 is a promoter-less GUS marker gene cassette. A circular map of the plasmid is shown in FIG. 3. When a 35s promoter is added to p2117, the marker gene is able to express GUS in plant tissue. Plasmid 2117 was digested with Nco I and Bam HI and gel purified. The 2 Kb Nco I/Bam HI fragment containing the GUS gene was ligated to the 7.5 Kb E6 genomic fragment and transformed into XL-1 Blue cells. Recombinant clones (p2117-E6) were identified by SDS-agarose gels. However, this construct lacks a poly(A)-addition signal. Therefore, a 277 bp Bam HI fragment of p2117, which contains the poly(A)-addition signal, was ligated into the Bam HI site of p2117-E6. The orientation of the poly(A) addition signal in p2117E6P-2A was then determined by restriction digestion analysis and the chimeric plasmid containing the correct orientation was selected. The construction of the plasmid is shown in FIG. 4.

Plasmid p2117E6P-2A was then introduced into cotton hypocotyls through particle acceleration method (McCabe, D., et al., *Bio/Technology,* 6:923–926 (1988)). As mentioned above, control experiments used plasmids p2119, p2117, and pSKSIE6-2AH3. Plasmid p2119, a GUS construct with the 35s promoter gave positive GUS activity as expected. Plasmid 2117 (no plant promoter) and plasmid SKSIE6-2AH3 (no GUS gene) gave no GUS activity. Plasmid p2117E6P-2A which contains the region 5' to the E6 gene and the GUS gene, showed GUS activity. This result suggests that an active promoter element is located in the 4.5 Kb Nco I/Sal I DNA fragment.

b. Sea Island E6-3B Gene and Promoter.

Figure 5:
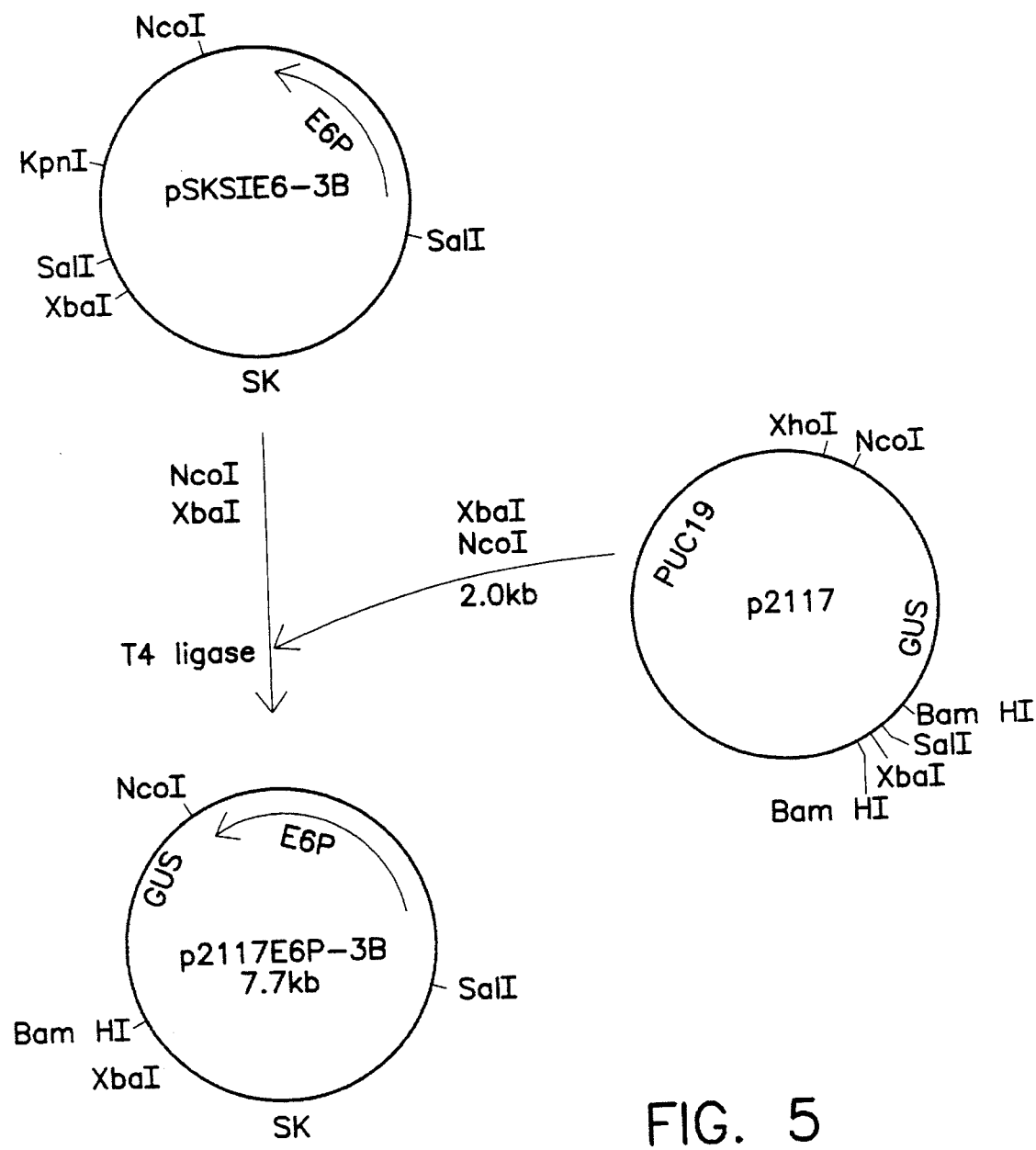
FIG. 5 is a diagram of the construction of plasmid p2117E6P-3B.

A second phage (insert 15 Kb) hybridizing to E6 cDNA contains a Sal I fragment (5.1 Kb). This fragment was subcloned into $SK^+$ vector. This plasmid (pSKSIE6-3B) was characterized in terms of the region to which E6 cDNA hybridize. 581 bp of promoter region, 33 bp of 5' noncoding region, 741 bp of coding region, and 313 bp of 3' noncoding region are shown in SEQ ID NO: 21. Promoter fragment identification of pEKSIE6-3B gene was carried out as follows. After determining the coding region and the putative promoter region in pSKSIE6-3B it was digested with Nco I and Xba I and the resulting plasmid (approximately 5.7 Kb) gel purified. Similarly the promoter-less GUS gene cassette was digested with NCO I/Xba I and gel purified. The GUS gene was then ligated to plasmid pSKSIE6-3B. Construction of p2117 E6P-3B is shown in FIG. 5. As described for p2117E6P-2A, various control plasmids along with p2117E6P-3B were introduced into hypocotyl to test promoter activity. p2117E6P-3B showed GUS expression indicating that the 2.7 Kb Nco I/Sal I E6-3B fragment contains the promoter of E6-3B gene. Relative expression level of E6-3B promoter is shown in FIG. 2.

c. Coker E6 Gene pSKCKE6-1A and Promoter.

The screening of a Coker 312 genomic library with pCKFb15A1-E6 cDNA resulted in the identification of two phages, DASHCKE6-1A and DASHCKE6-4A. Inserts from these two phages were subcloned into SK+ vector.

A 12 Kb insert from phage DASHCKE6-1A was subcloned into SK+ vector to give pSKCKE6-1A plasmid. A detailed restriction map of the insert was prepared and its comparison with the map of pCKFb15A1-E6 enabled us to locate the coding region of Coker E6 gene in pSKCKE6-1A. About 567 bp of promoter, 33 bp of 5' noncoding region, 717 bp of coding region, and 301 bp of 3' noncoding region are included in the sequence and is shown in SEQ ID NO: 22. A 4.1 Kb Nco I fragment upstream of the coding region most likely contains the promoter of this gene. To confirm this, the Nco I fragment was ligated into the Nco I site of p2117 and the construct was tested for GUS activity as described earlier. The results demonstrated that the 4.1 Kb fragment contains a promoter.

d. Coker E6 Gene pSKCKE6-4A and Promoter.

An 8.0 Kb Sal I fragment from a second phage (12.2 Kb insert) hybridized to E6 cDNA. This fragment was subcloned into SK+ vector (pSKCKE6-4A). 512 bp of promoter region, 37 bp of 5' noncoding region, 726 bp of coding region, and 303 bp of 3' noncoding region have been sequenced and is shown in SEQ ID NO: 23. In a manner similar to our work with pSKCKE6-1A, we determined the location of the promoter of this gene and subcloned a 3.9 Kb Nco I/Sal I fragment into p2117 at the Xho I/Nco I sites. The resulting plasmid was then tested for GUS activity and was found to be able to direct synthesis of GUS enzyme in plant tissue.

e. Characterization of Cebia pentandra (Kapok E6 Gene and Promoter.

An EMBL-3 genomic library of *Cebia pentandra* (Kapok) was screened with E6 cDNA. Four hybridizing phages were identified. One of the phage inserts was subcloned into Sal I site of Bluescript vector SK+. The resulting clone, pSKCPE6-3A (15.3 Kb insert) was characterized by restriction analysis and Southern blotting. We identified a Sal I - Eco RV fragment (4.8 Kb) that hybridizes to CKFB15A1-E6. This fragment was subcloned into the Sal I - Eco RV site of Bluescript vector resulting in clone pSKCPE6-3A-RV. A 1.6 Kb stretch of DNA was sequenced and is shown in SEQ ID NO: 24. Comparison of cotton E6 cDNA sequence and Kapok E6 gene sequence revel 84.3% homology.

Figure 6:
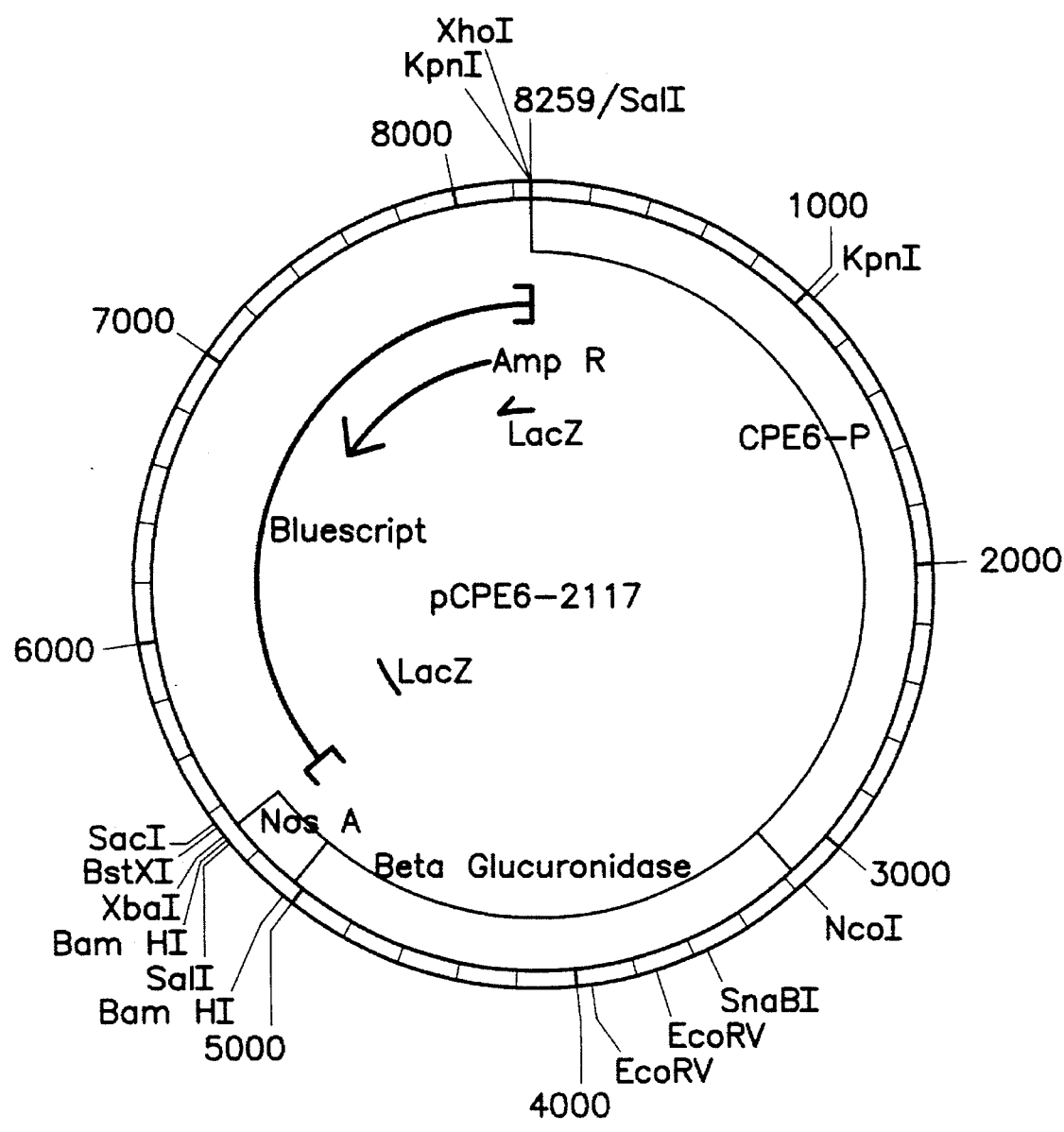
FIG. 6 is a diagram of plasmid pCPE6-2117.

Plasmid SKCPE6-3A-RV was digested with Nco I and Bam HI and the fragments separated on agarose gels. The larger of the DNA fragments (6.2 Kb, a 3.2 Kb insert and a 3 Kb vector) was electroeluted and purified. Similarly, GUS gene containing p2117 was digested with Nco I and Bam HI and the 1.8 Kb GUS fragment isolated and purified. The two DNA fragments were then ligated and transformed into X1-1 Blue cells. Recombinant clones were identified by DNA analysis on SDS-agarose gels (Sekar, et al., supra). A Nos poly(A) signal region from p2117 was isolated by Bam HI digestion. This fragment was ligated into the Bam HI site of the above Kapok E6-GUS plasmid after linearization with Bam HI. The resulting clones was analyzed for correct orientation of the Nos poly(A) addition signal by restriction digestion analysis. A circular map of pCPE6-2117 is shown in FIG. 6.

Plasmid CPE6-2117 was introduced into cotton hypocotyls through particle acceleration method (McCabe et al., supra). In duplicate experiments, pSKCPE6-RV, p2117 and p2119 were introduced into hypocotyls. As described earlier, GUS activity was assayed. As expected, pSKCPE6-RV and p2117 showed no GUS activity while p2119 gave positive results. The plasmid CPE6-2117 showed GUS activity, confirming that the 3.2 Kb Sal I/Nco I fragment contains the promoter for CPE6 gene.

f. Characterization of Sea Island H6 Gene and Its Promoter

Figure 7:
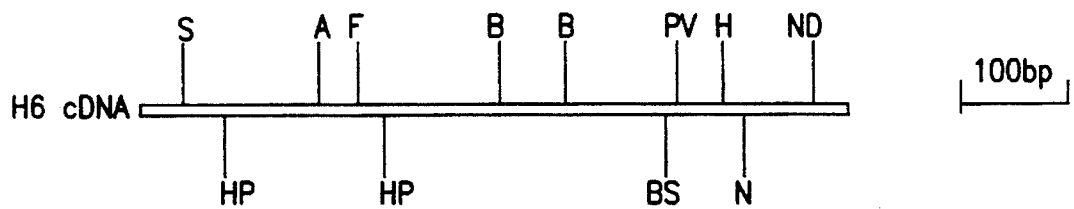
FIG. 7 is a diagram of H6 cDNA.
Figure 8:
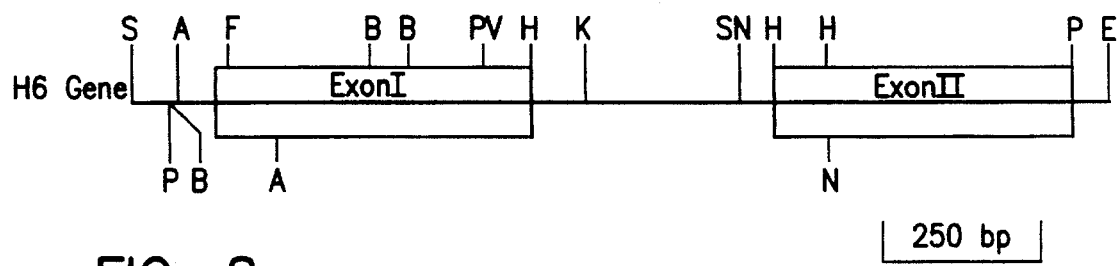
FIG. 8 is a diagram of the H6 gene.
Figure 9:
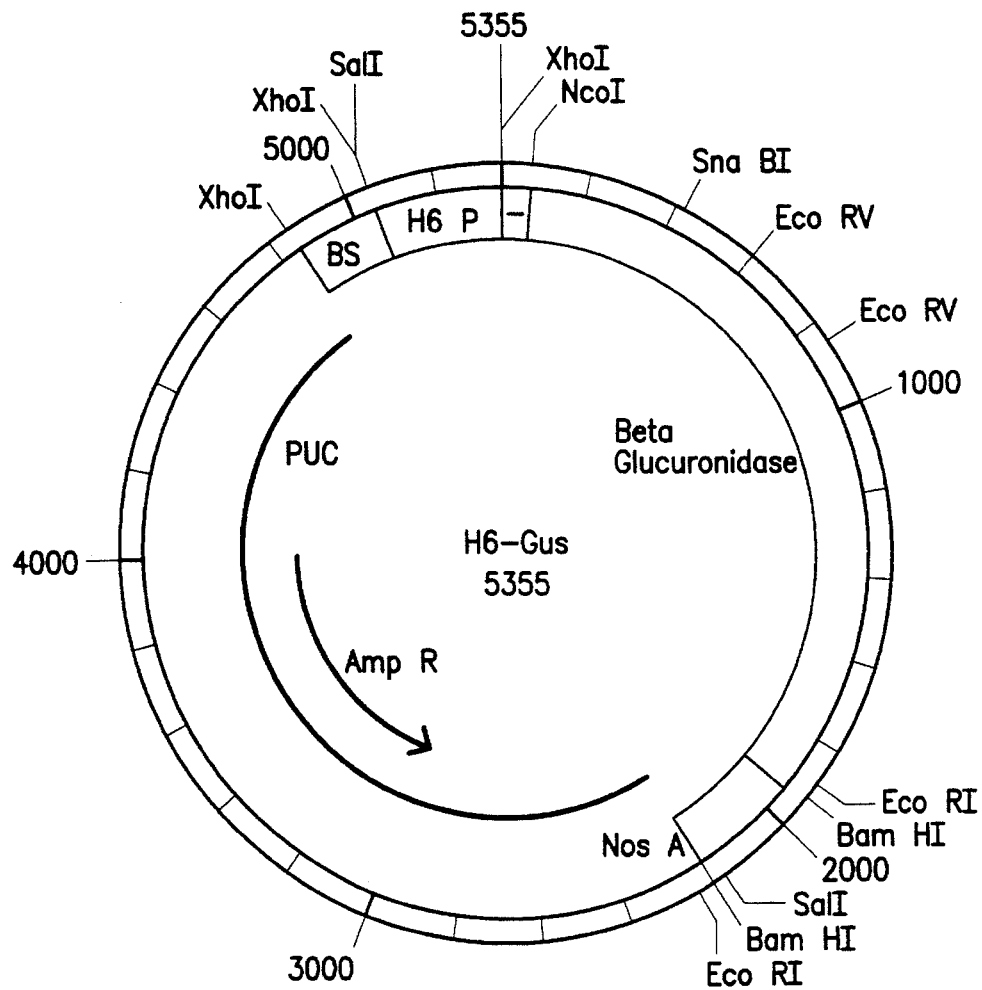
FIG. 9 is a diagram of plasmid pH6-2117.

A 13 Kb Sal I fragment from the H6 genomic clone, EMBLSIH6-4, was subcloned into Bluescript SK+ vector and designated pSKSIH6-4. After identifying the cDNA hybridizing region in pSKSIH6-4, the H6 gene was further subcloned by digesting the plasmid with Eco RI, purifying the fragments, and ligating them to SK+ vector. One of the resulting plasmids, designated pSIH6-4R1, contains the H6 gene. The complete sequence of the H6 coding region as well as the 300 bases upstream from the initiation codon were determined. These sequences are presented at SEQ ID NO: 25. Digestion with the enzyme Fsp I releases this 300 bp region, together with 250 bp of vector sequence. The 550 bp fragment was tested for promoter function in a similar fashion described for E6 genes, and is found to be active. FIG. 7 is a diagram of H6 cDNA. FIG. 8 is a diagram of the H6 gene. FIG. 9 describes the plasmid pH6-2117.

g. Characterization of B12 Gene and Its Promoter

A genomic clone corresponding to pCKFB10-B12 was isolated from the Sea Island genomic library. The 15 Kb insert from the phage, EMBLSI-B12, was subcloned into an SK+ vector as a Sal I fragment. Further subcloning of the insert as a Hind III fragment (7.3 Kb) into SK+ vector resulted in plasmid pSKSI-B12H3. The sequence of B12 gene and 5' flanking promoter region is shown in SEQ ID NO: 26.

The promoter fragment of the gene was identified as follows. The fragment corresponding to the 5' end of the cDNA in the B12 gene was excised as an EcoR1/Sty I fragment (3.1Kb) and gel purified. After T4 DNA polymerase treatment, Nco I linkers were added and then ligated to the Nco I site of p2117. Orientations of the fragment in relation to GUS gene was determined by restriction mapping and clones with the correct orientation was selected. pB12-2117 was introduced into hypocotyl tissue through particle bombardment for GUS activity measurements.

h. Characterization of Sea Island A-11 Gene and Its Promoter

The fiber cDNA A-11 was used to screen a Sea Island genomic library and isolate phage EMBLSI-A11A and EMBLSI-A11B. The insert of the phage EMBLSI-A11B (17 Kb) was subcloned into SK+ vector and subjected to restriction mapping and Southern analysis. A 4.9 Kb Sal I fragment that hybridized to pCKFB10-A11 cDNA was then subcloned into SK+ vector (pSKSIA11-B) and the cDNA hybridizing region determined by further restriction mapping and Southern analysis. Sequence analysis of the cDNA had determined that is contains an open reading frame of 552 bases. Presumably the promoter of the gene is located in a Sal I/Eco RI fragment (2.1 Kb). To test this, a chimeric construct was made as follows. ASK+ vector was modified to include a unique Nco I site in the poly linker. The Sal I/Eco R1 fragment (2.1 Kb) was cloned into Sal I/Eco RI site of Nco-SK+ vector followed by an Nco I/Xho I GUS fragment from the p2117 plasmid. The resulting plasmid pA11B-2117 was then tested for GUS activity in hypocotyl tissue. It is found that pA11B-2117 expressed GUS. From these results we conclude that A11-B promoter is located in the Sal I/Eco R1 fragment. Sequence of the A-11 gene promoter is given in SEQ ID NO: 27.

i. Characterization of B8 Gene and Its Promoter

The insert of B8 cDNA clone was used to isolate a phage from Sea Island genomic library (19 Kb insert). A Sal I/Bam HI fragment from the phage DNA that hybridized BH8 cDNA insert was subcloned into SK$^+$ vector. This generated a 9.5 Kb fragment that contained the B8 gene. A 2.5 Kb DNA part was then sequenced and was shown to contain homologous sequences to B8. SEQ. ID NO: 28 is the B8 gene. Based on the sequence comparison of the cDNA and gene, we determined that a 2.1 Kb Bam HI/BstB1 fragment would contain the B8 promoter. In order to create an Nco I site at the 3' end of the promoter fragment for convenient cloning of genes, we modified the B8 promoter by PCR. Two PCR primers MEJ117 and MEJ118, (SEQ ID NO: 30 and SEQ ID NO: 31) were used to amplify a 120 bp fragment. MEJ118 contained a BstBI and an Nco I site. The PCR product was digested with BstBI and purified. Similarly the B8 vector, pSKSIB8 clone was also digested with BstBI and a 7 Kb fragment was gel purified and ligated to the PCR product. Recombinant clones containing the B8 vector were then screened and the orientation of the 120 bp insert in B8 was determined by PCR. Now the plasmid was ready for determination of B8 promoter activity. The above plasmid was digested with Nco I and Sal I and gel purified. A GUS-containing clone pSIB8GUS was then introduced into cotton hypocotyl tissue through particle bombardment. Appropriate control experiments were included. These studies show that B8 fragment contains promoter activity.

j. Characterization of Sea Island B6 Gene and Its Promoter

A phage, EMBLSIB6-1A, was identified from the screening of the genomic library. A 12.3 Kb Sal I fragment of EMBLSIB6-1A was subcloned into SK$^+$ vector. After determining that B6 cDNA hybridizes to a 4.3 Kb Xho I/Sal I fragment, we isolated the 5' end of the B6 gene as a Bam HI/Xho I fragment (2.3 Kb) and ligated it into Xho I/Bam HI sites of SK$^+$ vector. Subsequently, a 2.0 Kb Xho I/Sal I GUS fragment of p2117 was ligated into the B6 vector at the Xho I site. This plasmid pB6-2117 was then introduced into hypocotyl tissue along with control plasmids by particle bombardment. GUS activity was detected after 24 hours of bombardment indicating that the Xho I/Bam HI fragment contains a functional promoter. Sequence of this 5' flanking region containing B6 promoter is given in SEQ ID NO: 29.

k. Characterization of Sea Island E9 Gene and Its Promoter cDNA pCKFb23-E9 was used to isolate a phage EMBLSI-E9 from Sea Island library. The 12.4 Kb Sal I insert from EMBLSI-E9 was subcloned into Sk$^+$ vector (pSKSI-E9). We determined the DNA fragment that hybridizes to E9 cDNA, by restriction mapping and Southern hybridization. The cDNA and the gene contains an Nco I site at the 5' end. DNA fragment 5' to the unique Nco I site (an Nco I/Xho I fragment of 7.0 Kb) was used to generate a chimeric GUS plasmid to test promoter function of the Nco I/Xho I fragment. In particle bombardment experiments the pE9-2117 construct was found to be active in expressing GUS enzyme.

l. Characterization of Sea Island A12 Gene and Its Promoter

The cDNA was used to isolate two genomic clones, EMBLSI-A12A and EMBLSI-A12B from Sea Island library. The inserts of the phages were subcloned into SK$^+$ vectors. The subclone of EMBLSI-A12A was further characterized in terms of restriction map and Southern analysis. From these studies we concluded that a Sal I fragment (6.7 Kb) contains the A12 gene.

10. Tissue-Specific Expression of Fiber Gene Promoters in Transgenic Plants

In order to demonstrate that various fiber gene promoters can be used to express foreign proteins in cotton fiber in a tissue-specific manner, the following experiments were carried out. The coding region of a carrot extensin gene was fused to the E6 promoter (restriction fragment Sal I/Nco I, SEQ ID NO: 21). Extensin is a hydroxyproline rich glycoprotein found in the cell-walls of a number of plants. Chem and Varner. *EMBO J.* 4:2145–2151 (1985). We have ascertained that extensin cDNA did not hybridize to control cotton tissue RNAs, including fiber. Thus, extensin is not expressed in cotton plants.

A chimeric extensin gene with a fiber-specific promoter was constructed as follows. A 1.34 Kb Eco RI/Dra I fragment containing the extensin gene was excised from plasmid pDC5A1 (a generous gift from J. Varner's lab), and subcloned into Sma I/Eco RI sites of SK+ vector to generate plasmid SK-Extensin. In order to facilitate further cloning, a Nco I site was introduced into the 5' noncoding region of PCR as follows. Two PCR primers MEJ15 and MEJ16 were used to amplify a 166 bp fragment from the carrot extensin gene. MEJ16 contained an Nco I and Xho I sites. The primer sequences are shown in SEQ ID NO: 32 and 33.

Plasmid SK-Extensin was digested with Xho I/Ava I and the large plasmid fragment purified by gel electrophoresis. The PCR product was digested with Xho I/Ava I, gel purified, and subsequently ligated into SK-Extensin. The coding region and the 5' and 3' noncoding regions of extensin can be excised as a Nco I/Bst XI (1.51 Kb) fragment from the resulting plasmid. This fragment is ligated into a Nco I/Bst XI digested E6 promoter vector pSKSIE6-3B (supra). The new plasmid was called pE6-3B-Ext.

Figure 10:
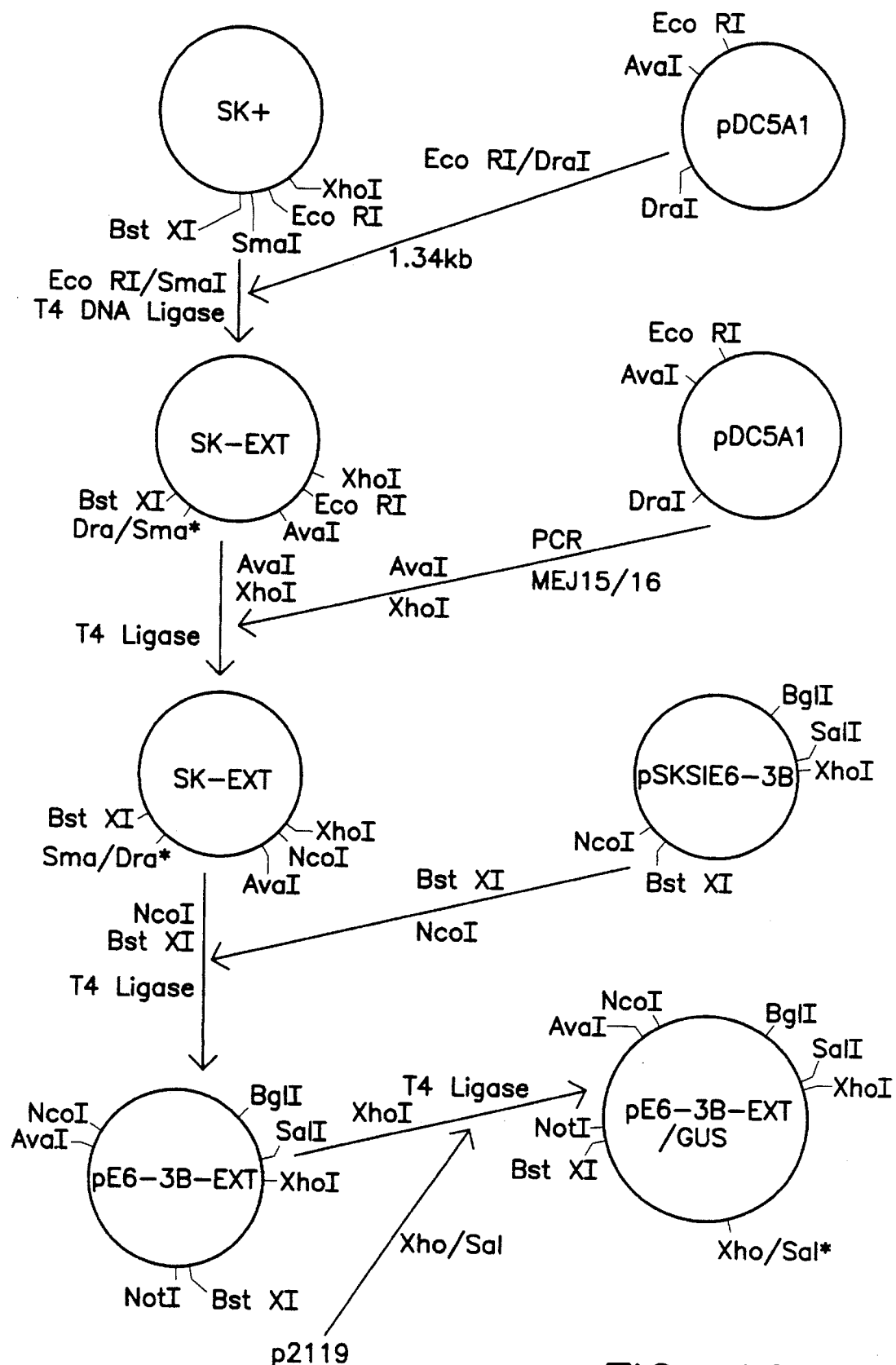
FIG. 10 is a diagram of the construction of plasmid pE6-3B-Ext.

A GUS marker gene was added to the above construct as follows: A 35s viral promoter-driven GUS marker gene was excised from plasmid p2119 (supra) as a Xho I/Sal I fragment and was cloned into the Xho I site of pE6-3B-Ext. The construction of pE6-3B-Ext/GUS is shown in FIG. 10. The construct was ready for transformation into cotton.

More than 30 transgenic cotton plants containing E6-3B-Ext gene were generated. A number of these plants were then tested for expression of extensin in various tissues. By northern analysis we observed expression of extensin in 10 and 15 day fiber, but not in leaf, ovule, stem, or root. This result indicates that E6 promoters can be utilized to express proteins in fiber in a tissue-specific manner. Moreover, the introduced gene is developmentally regulated.

11. Transgenic Cotton Plants Containing H6 Promoter

We have demonstrated that the H6 promoter can be utilized to express proteins in fiber. An Agrobacterium tumefaciens hormone gene, tryptophan mono-oxygenase (TMO) that takes part in the synthesis of hormone indole acetic acid (IAA) was fused to H6 promoter and incorporated into cotton genome through particle bombardment (McCabe et al., supra). Examination of the IAA content from transgenic cotton fiber provides evidence that the gene is active in fiber.

12. Assessing Fiber Quality

When the transgenic cotton is able to produce mature fiber, the fiber must be examined in order to determine whether advantageous alterations have occurred. Cotton fiber length is genetically determined and therefore varies from cultivar to cultivar. Commercially, American upland cottons are classified as either short staple (up to 1 inch; 2.5 cm), medium staple (1-1/32 to 1-3/32 inch; 2.63– 2.78 cm), or long staple (over 1-⅛ inch; over 2.86 cm). Instruments such as a fibrograph and HVI (high volume instrumentation) systems are used to measure the length of the fiber. HVI instruments compute length in terms of "mean" and "upper half mean" (UHM) length. The mean is the average length of all the fibers while UHM is the average length of the longer half of the fiber distribution.

Fiber strength is usually defined as the force required to break a bundle of fibers or a single fiber. In HVI testing the breaking force is converted to "grams force per tex unit." This is the force required to break a bundle of fibers that is one tex unit in size. In HVI testing the strength is given in grams per tex units (grams/tex). Fibers can be classified as (1) low strength, 19–22 gms/tex, (2) average strength, 23–25 gms/tex, (3) high strength, 26–28 gms/tex, and (4) very high strength, 29–36 gms/tex.

The micronaire reading of fiber is obtained from a porous air flow test. The test is conducted as follows. A weighed sample of cotton is compressed to a given volume and controlled air flow is passed through the sample. The resistance to the air flow is read as micronaire units. The micronaire readings reflects a combination of maturity and fineness. Since the fiber diameter of fibers within a given variety of cotton is fairly consistent, the micronaire index will more likely indicate maturity variation rather than variations in fineness. A micronaire reading of 2.6–2.9 is low while 3.0–3.4 is below average, 3.5–4.9 is average and 5.0 and up are high. For most textile applications a micronaire of 3.5–4.9 is used. Anything higher than this is not desirable. Of course, different applications require different fiber properties. A fiber property that is disadvantageous in one application might be advantageous in another.

It is to be understood that all nucleotide sequence and size data presented herein is approximate and, although presented as best understood at the present time, may be subject to some variation.

It is to be understood that the present invention is not confined to the particular construction and arrangement herein illustrated and described, but embraces such modified forms thereof as come within the scope of the following claims.

I claim:

1. A method of expressing foreign genes in a fiber-producing plant comprising the steps of:

a) constructing a plant expression vector that comprises a protein coding sequence operably linked to a DNA sequence which promotes preferential gene expression in fiber cells, wherein the DNA sequence is not naturally associated with said protein coding sequence and is selected from the group consisting of the gene E6 4.5 Kb Mbo I/Nco I fragment which contains the first 541 bD of SEQ ID NO:20; the gene E6 2.7 Kb Mbo I/Nco I fragment which contains the first 581 bD of SEQ ID NO:21; the gene E6 4.1Kb Nco I fragment which contains the first 567 bp SEQ ID NO:22; the gene E6 3.9 Kb Mbo I/Nco I fragment which contains the first 512 bp of SEQ ID NO:23; the gene E6 3.2 Kb Mbo I/Nco I fragment which contains the first 421 bp of SEQ ID NO:24; the gene H6 321 bp Fsp I/Mbo I fragment which contains the first 250 bp of SEQ ID NO:25; the gene A-11 2.1 Kb Mbo I/Eco RI fragment which contains the first 279 bp of SEQ ID NO:27; the gene B8 2.2 Kb Bam HI/Bst BI fragment which contains the first 287 bp of SEQ ID NO:28; and b) introducing the expression vector into a fiber-producing plant cell, which is regenerated into a fiber-producing plant, wherein the protein coding sequence is expressed in the fiber cells of the fiber-producing plant.

2. A method of expressing foreign genes in a fiber-producing plant comprising the steps of:

a) constructing a plant expression vector that comprises a protein coding sequence operably linked to a DNA sequence which promotes preferential gene expression in fiber cells, wherein the DNA sequence is not naturally associated with said protein coding sequence and is selected from the group consisting of the first 541 bp of SEQ ID NO:20; the first 581 bp of SEQ ID NO:21, the first 567 bp of SEQ ID NO:22, the first 512 bp of SEQ ID NO:23; the first 421 bp of SEQ ID NO:24; the first 250 bp of SEQ ID NO:25; the first 279 bp of SEQ ID NO:27; and the first 287 bp of SEQ ID NO:28; and b) introducing the expression vector into a fiber-producing plant cell, which is regenerated into a fiber-producing plant, wherein the protein coding sequence is expressed preferentially in the fiber cells of the fiber-producing plant.

3. A DNA construction comprising a sequence capable of promoting preferential expression of a protein coding sequence in fiber cells selected from the group consisting of the first 541 bp of SEQ ID NO:20; the first 581 bp of SEQ ID NO:21, the first 567 bp of SEQ ID NO:22, the first 512 bp of SEQ ID NO:23; the first 421 bp of SEQ ID NO:24; the first 250 bp of SEQ ID NO:25; the first 279 bp of SEQ ID NO:27; and the first 287 bp of SEQ ID NO:28, a protein coding sequence not naturally associated with said sequence that promotes preferential expression in fiber cells, and a 3' termination sequence, operably joined in a 5' to 3' direction.

4. A fiber producing plant comprising in its genome the DNA construction of claim 3.

5. A fiber producing plant produced by the method of claim 2.

* * * * *